United States Patent
Bhagirath et al.

(10) Patent No.: US 9,988,378 B2
(45) Date of Patent: Jun. 5, 2018

(54) 1 H-PYRAZOLE AND 4,5-DISUBSTITUTED THIAZOLE INHIBITORS OF SYK

(71) Applicant: Hoffmann-La Roche Inc., Nutley, NJ (US)

(72) Inventors: Niala Bhagirath, Bloomfield, NJ (US); Joshua Kennedy-Smith, New York, NY (US); Matthew C. Lucas, Lexington, MA (US); Fernando Padilla, Verona, NJ (US)

(73) Assignee: Hoffmann-La Roche Inc., Basle (CH)

( * ) Notice: Subject to any disclaimer, the term of this patent is extended or adjusted under 35 U.S.C. 154(b) by 0 days. days.

(21) Appl. No.: 14/437,307

(22) PCT Filed: Oct. 23, 2013

(86) PCT No.: PCT/EP2013/072132
§ 371 (c)(1),
(2) Date: Apr. 21, 2015

(87) PCT Pub. No.: WO2014/064134
PCT Pub. Date: May 1, 2014

(65) Prior Publication Data
US 2015/0266874 A1 Sep. 24, 2015

Related U.S. Application Data

(60) Provisional application No. 61/718,740, filed on Oct. 26, 2012.

(51) Int. Cl.
| | | |
|---|---|---|
| *C07D 403/04* | (2006.01) | |
| *C07D 471/04* | (2006.01) | |
| *C07D 401/04* | (2006.01) | |
| *C07D 403/14* | (2006.01) | |
| *C07D 409/04* | (2006.01) | |
| *C07D 417/04* | (2006.01) | |
| *C07D 417/14* | (2006.01) | |
| *A61K 31/415* | (2006.01) | |
| *A61K 31/4155* | (2006.01) | |
| *A61K 31/427* | (2006.01) | |
| *A61K 31/428* | (2006.01) | |
| *A61K 31/437* | (2006.01) | |
| *A61K 31/4439* | (2006.01) | |
| *A61K 31/454* | (2006.01) | |
| *A61K 45/06* | (2006.01) | |

(52) U.S. Cl.
CPC .......... *C07D 471/04* (2013.01); *A61K 31/415* (2013.01); *A61K 31/4155* (2013.01); *A61K 31/427* (2013.01); *A61K 31/428* (2013.01); *A61K 31/437* (2013.01); *A61K 31/4439* (2013.01); *A61K 31/454* (2013.01); *A61K 45/06* (2013.01); *C07D 401/04* (2013.01); *C07D 403/04* (2013.01); *C07D 403/14* (2013.01); *C07D 409/04* (2013.01); *C07D 417/04* (2013.01); *C07D 417/14* (2013.01)

(58) Field of Classification Search
CPC .................................................... C07D 403/04
USPC ........................................ 548/306.1; 514/394
See application file for complete search history.

(56) References Cited

U.S. PATENT DOCUMENTS

| | | | | |
|---|---|---|---|---|
| 6,897,208 | B2 * | 5/2005 | Edwards | .............. C07D 231/12 514/183 |
| 7,179,823 | B1 | 2/2007 | Momose et al. | |
| 7,977,477 | B2 * | 7/2011 | Berdini | .................. A61K 31/00 544/140 |
| 8,399,442 | B2 | 3/2013 | Berdini et al. | |
| 2009/0131470 | A1 | 5/2009 | Walmsley et al. | |
| 2010/0160324 | A1 | 6/2010 | Berdini et al. | |

FOREIGN PATENT DOCUMENTS

| | | |
|---|---|---|
| JP | 2002161084 | 6/2002 |
| JP | 2002161084 A | 6/2002 |
| JP | 2007119484 A | 5/2007 |
| WO | 03066629 A2 | 8/2003 |
| WO | 2005002576 A2 | 1/2005 |
| WO | 2005005414 | 1/2005 |
| WO | 2006070192 | 7/2006 |
| WO | 2006091592 A1 | 8/2006 |
| WO | 2008129054 A2 | 10/2008 |
| WO | 2009027393 | 3/2009 |
| WO | 2010091310 A1 | 8/2010 |
| WO | 2011003065 A2 | 1/2011 |
| WO | 2011150457 A2 | 12/2011 |

(Continued)

OTHER PUBLICATIONS

The International Search Report and Written Opinion, issued on Nov. 15, 2013, in the corresponding PCT Application No. PCT/EP2013/072132.

(Continued)

*Primary Examiner* — Patricia L Morris

(57) ABSTRACT

The present invention relates to the use of novel compounds of formula (I), wherein all variable substituents are defined as described herein, which are SYK inhibitors and are useful for the treatment of auto-immune and inflammatory diseases.

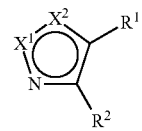

1 Claim, No Drawings

(56) References Cited

FOREIGN PATENT DOCUMENTS

| WO | 2012025186 | 3/2012 |
|---|---|---|
| WO | 2013124025 | 8/2013 |
| WO | 2014041175 A1 | 3/2014 |

OTHER PUBLICATIONS

Ribecai et al., "Identification of a Manufacturing Route of Novel CRF-1 Antagonists Containing a 2,3-Dihydro-1H-pyrrolo[2,3-b]pyridine Moiety," Org. Process Res. Dev., 2010, 14 (4), pp. 895-901.

Howard et al., "Fragment-based discovery of the pyrazol-4-yl urea (AT9283), a multitargeted kinase inhibitor with potent aurora kinase activity," J Med Chem. Jan. 22, 2009;52(2):379-88.

Schiffmann et al., "Metal-mediated inhibition of *Escherichia coli* methionine aminopeptidase: structure-activity relationships and development of a novel scoring function for metal-ligand interactions," J Med Chem. Jan. 26, 2006;49 (2):511-22.

Tocco et al.,"The Metabolic Fate of Thiabendazole in Sheep," J Med Chem. Jul. 1964;7:399-405.

Amoroso et al., "Synthesis of the new tripodal ligand tris-[3-(2'-pyridyl)pyrazol-1-yl]hydroborate, and the crystal structure of its europium(III) complex," J Chem Soc, Chem Commun, 1994, p. 2751-2752.

Plate et al., "Synthesis and muscarinic activities of 3-(pyrazolyl)-1,2,5,6-tetrahydropyridine derivatives," Bioorg Med Chem. Feb. 1996;4(2):227-37.

Hayat et al., "Synthesis, characterization, antiamoebic activity and cytotoxicity of novel 2-(quinolin-8-yloxy) acetohydrazones and their cyclized products (1,2,3-thiadiazole and 1,2,3-selenadiazole derivatives)," Eur J Med Chem. Dec. 2010;45(12):6127-34.

Feiyue et al., "Bidentate Ligands That Contain Pyrrole in Place of Pyridine," Inorg. Chem., 2000, 39 (3), pp. 584-590.

The English translation of the Chinese Office Action, dated Apr. 8, 2016, in the corresponding Chinese Application No. 201380042831.9.

Hohwy et al., "Novel Prostaglandin D Synthase Inhibitors Generated by Fragment-Based Drug Design," J. Med. Chem. 2008, 51, 2178-2186.

The English translation of the Taiwanese Search Report, dated Mar. 23, 2017, in the corresponding Taiwanese Application No. 102138784.

The English translation of the Chinese Office Action, dated Mar. 21, 2017, in the related Chinese Application No. 01380042831.9.

The English translation of the Japanese Office Action, dated Jul. 25, 2017, in the related Japanese Application No. 2015-538425.

The English translation of the Russian Office Action, dated Aug. 13, 2017, in the related Russian Application No. 2015117950.

Isaburo et al., "The Paal-Knorr Conden6ation of Acetonyincetone with 5-Amin opyrazoles," Bull. Chem. Soc. Jpn. 1971, vol. 44, pp. 2856-2858.

\* cited by examiner

1 H-PYRAZOLE AND 4,5-DISUBSTITUTED THIAZOLE INHIBITORS OF SYK

This application is a National Stage Application of PCT/EP2013/072132 filed Oct. 23, 2013, which claims priority from U.S. Provisional Patent Application No. 61/718,740, filed on Oct. 26, 2012. The priority of both said PCT and U.S. Provisional Patent Application are claimed. Each of the prior mentioned applications is hereby incorporated by reference herein in its entirety.

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

SYK (Spleen Tyrosine Kinase) is a non-receptor tyrosine kinase that is essential for B-cell activation through BCR signaling. SYK becomes activated upon binding to phosphorylated BCR and thus initiates the early signaling events following BCR activation. Mice deficient in SYK exhibit an early block in B-cell development. Therefore inhibition of SYK enzymatic activity in cells is proposed as a treatment for autoimmune disease through its effects on autoantibody production.

In addition to the role of SYK in BCR signaling and B-cell activation, it also plays a key role in FcεRI mediated mast cell degranulation and eosinophil activation. Thus, SYK is implicated in allergic disorders including asthma. SYK binds to the phosphorylated gamma chain of FcγRI via its SH2 domains and is essential for downstream signaling. SYK deficient mast cells demonstrate defective degranulation, arachidonic acid and cytokine secretion. This also has been shown for pharmacologic agents that inhibit SYK activity in mast cells. Treatment with SYK antisense oligonucleotides inhibits antigen-induced infiltration of eosinophils and neutrophils in an animal model of asthma. SYK deficient eosinophils also show impaired activation in response to FcεR stimulation. Therefore, small molecule inhibitors of SYK will be useful for treatment of allergy-induced inflammatory diseases including asthma.

In view of the numerous conditions that are contemplated to benefit by treatment involving modulation of the SYK pathway it is immediately apparent that new compounds that modulate the SYK pathway and methods of using these compounds should provide substantial therapeutic benefits to a wide variety of patients. Provided herein are novel compounds for use in the therapeutic treatment of autoimmune and inflammatory diseases by targeting the SYK pathway or by inhibition of SYK kinase . . .

The application provides a compound of Formula I wherein:

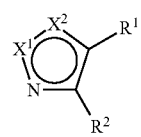

$R^1$ is H, C(=O)OR$^{1'}$, NHC(=O)(CR$^{1''}_2$)$_n$R$^{1'}$, C(=O)NH(CR$^{1''}_2$)$_n$R$^{1'}$, or NHR$^{1'}$;
  $R^{1'}$ is lower alkyl, cycloalkyl, heterocycloalkyl, lower alkyl heterocycloalkyl, O(=O)R$^{1''}$, OH, or heteroaryl;
  each $R^{1''}$ is independently H or lower alkyl;
  n is 0, 1 or 2;
$R^2$ is monocyclic or bicyclic unsaturated or partially saturated heteroaryl, optionally substituted with one or more $R^{2'}$;
  each $R^{2'}$ is independently lower alkyl, lower alkoxy, or phenyl;
$X^1$ is NH or CH; and
$X^2$ is CH or S;
or a pharmaceutically acceptable salt thereof.

The application provides a method for treating an inflammatory or autoimmune condition comprising administering to a patient in need thereof a therapeutically effective amount of the compound of Formula I.

The application provides a pharmaceutical composition comprising the compound of Formula I, admixed with at least one pharmaceutically acceptable carrier, excipient or diluent.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

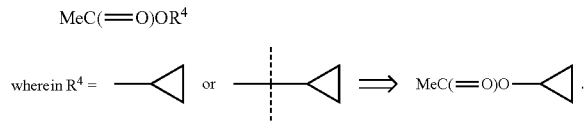

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH-Δ-C(—OH)=CH—), amide/imidic acid (—C(=O)—NH-Δ-C(—OH)=N—) and amidine (—C(=NR)—NH-Δ-C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term—(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro [3.3]heptane. The term spiroheterocycloalkyl, as used herein, means a spirocyclic heterocycloalkyl, such as, for example, 2,6-diaza spiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term C$_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "C$_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe— or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethylethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "carboxy-alkyl" as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —CO$_2$H moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N,O or S(O)$_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

The application provides a compound of Formula I wherein:

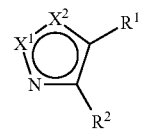

I

R$^1$ is H, C(=O)OR$^{1'}$, NHC(=O)(CR$^{1''}_2$)$_n$R$^{1'}$, C(=O)NH(CR$^{1''}_2$)$_n$R$^{1'}$, or NHR$^{1'}$;
R$^{1'}$ is lower alkyl, cycloalkyl, heterocycloalkyl, lower alkyl heterocycloalkyl, O(=O)R$^{1'''}$, OH, or heteroaryl;
each R$^{1''}$ is independently H or lower alkyl;
n is 0, 1 or 2;
R$^2$ is monocyclic or bicyclic unsaturated or partially saturated heteroaryl, optionally substituted with one or more R$^{2'}$;
each R$^{2'}$ is independently lower alkyl, lower alkoxy, or phenyl;
X$^1$ is NH or CH; and
X$^2$ is CH or S;
or a pharmaceutically acceptable salt thereof.

The application provides a compound of Formula I wherein:

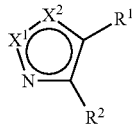

R¹ is H, C(=O)OR¹', NHC(=O)(CR¹"₂)ₙR¹', C(=O)NH(CR¹"₂)ₙR¹', or NHR¹';
R¹' is lower alkyl, cycloalkyl, heterocycloalkyl, lower alkyl heterocycloalkyl, O(=O)R¹", OH, or heteroaryl;
each R¹" is independently H or lower alkyl;
n is 0, 1 or 2;
R² is monocyclic or bicyclic unsaturated or partially saturated heteroaryl, optionally substituted with one or more R²';
each R²' is independently lower alkyl, lower alkoxy, or phenyl;
X¹ is NH or CH; and
X² is CH or S;
or a pharmaceutically acceptable salt thereof The application provides a compound of Formula I, wherein R² is bicyclic unsaturated or partially saturated heteroaryl, optionally substituted with one or more R²'.

The application provides a compound of Formula I, wherein R² is thiazolyl, triazolopyridinyl, benzothiazolyl, benzothiophenyl, benzoimidazolyl, cyclopentathiazolyl, imidazopyridinyl, pyridinyl, tetrahydrobenzothiazolyl, triazolopyridinyl optionally substituted with one or more R²'.

The application provides a compound of Formula I, wherein X¹ is NH and X² is CH.

The application provides a compound of Formula I, wherein X¹ is CH and X² is S.

The application provides a compound of Formula I, wherein X¹ is NH, X² is CH and R² is bicyclic unsaturated or partially saturated heteroaryl, optionally substituted with one or more R²'.

The application provides a compound of Formula I, wherein X¹ is CH, X² is S, and R² is bicyclic unsaturated or partially saturated heteroaryl, optionally substituted with one or more R²'.

The application provides a compound of Formula I, wherein R¹ is C(=O)NH(CR¹"₂)ₙR¹'.

The application provides a compound of Formula I, wherein R¹ is H.

The application provides a compound of Formula I, wherein R¹ is NHC(=O)(CR"₂)ₙR¹'.

The application provides a compound of Formula I, wherein R¹ is NHR¹'.

The application provides a compound of Formula I, wherein R¹ is C(=O)OR¹'.

The application provides a compound of Formula I, wherein R¹ is C(=O)NH(CR¹"₂)ₙR¹' and R² is bicyclic unsaturated or partially saturated heteroaryl, optionally substituted with one or more R²'.

The application provides a compound of Formula I, wherein R¹ is H and R² is bicyclic unsaturated or partially saturated heteroaryl, optionally substituted with one or more R²'.

The application provides a compound of Formula I, wherein R¹ is NHC(=O)(CR"₂)ₙR¹' and R² is bicyclic unsaturated or partially saturated heteroaryl, optionally substituted with one or more R²'.

The application provides a compound of Formula I, wherein R¹ is NHR¹' and R² is bicyclic unsaturated or partially saturated heteroaryl, optionally substituted with one or more R²'.

The application provides a compound of Formula I, wherein R¹ is C(=O)OR¹' and R² is bicyclic unsaturated or partially saturated heteroaryl, optionally substituted with one or more R²'.

The application provides a compound of Formula I, wherein R² is monocyclic unsaturated heteroaryl, optionally substituted with one or more R²'.

The application provides a compound of Formula I, wherein R² is monocyclic unsaturated heteroaryl, optionally substituted with one or more R²' and R¹ is C(=O)NH(CR¹"₂)ₙR¹'.

The application provides a compound selected from the group consisting of:
2-Phenyl-5-(1H-pyrazol-3-yl)-thiazole;
3-[1,2,4]Triazolo[1,5-a]pyridin-2-yl-1H-pyrazol-4-carboxylic acid ethyl ester;
N-(3-Benzothiazol-2-yl-1H-pyrazol-4-yl)-isobutyramide;
N-(3-Benzothiazol-2-yl-1H-pyrazol-4-yl)-2,2-dimethyl-propionamide;
Cyclopentanecarboxylic acid (3-benzothiazol-2-yl-1H-pyrazol-4-yl)-amide;
Cyclopropanecarboxylic acid (3-benzothiazol-2-yl-1H-pyrazol-4-yl)-amide;
3-(benzo[d]thiazol-2-yl)-N-(1-hydroxy-2-methylpropan-2-yl)-1H-pyrazole-4-carboxamide;
3-(benzo[d]thiazol-2-yl)-N-tert-butyl-1H-pyrazole-4-carboxamide;
N-(1-hydroxy-2-methylpropan-2-yl)-3-(5-methylbenzo[b]thiophen-2-yl)-1H-pyrazole-4-carboxamide;
N-tert-butyl-3-(5-methylbenzo[b]thiophen-2-yl)-1H-pyrazole-4-carboxamide;
N-tert-butyl-3-(6-methoxypyridin-2-yl)-1H-pyrazole-4-carboxamide;
(S)-3-(benzo[d]thiazol-2-yl)-N-(1-hydroxypropan-2-yl)-1H-pyrazole-4-carboxamide;
ethyl 3-(4-phenylthiazol-2-yl)-1H-pyrazole-4-carboxylate;
ethyl 3-(4,5,6,7-tetrahydrobenzo[d]thiazol-2-yl)-1H-pyrazole-4-carboxylate;
ethyl 3-(5,6-dihydro-4H-cyclopenta[d]thiazol-2-yl)-1H-pyrazole-4-carboxylate;
N-tert-butyl-3-(4-phenylthiazol-2-yl)-1H-pyrazole-4-carboxamide;
N-isopropyl-3-(4-phenylthiazol-2-yl)-1H-pyrazole-4-carboxamide;
N-tert-butyl-3-(5,6-dihydro-4H-cyclopenta[d]thiazol-2-yl)-1H-pyrazole-4-carboxamide;
N-tert-butyl-3-(4,5,6,7-tetrahydrobenzo[d]thiazol-2-yl)-1H-pyrazole-4-carboxamide;
N-cyclopentyl-3-(4-phenylthiazol-2-yl)-1H-pyrazole-4-carboxamide;
3-(4-phenylthiazol-2-yl)-N-(tetrahydro-2H-pyran-4-yl)-1H-pyrazole-4-carboxamide;
3-(5,6-dihydro-4H-cyclopenta[d]thiazol-2-yl)-N-(tetrahydro-2H-pyran-4-yl)-1H-pyrazole-4-carboxamide;
N-(tetrahydro-2H-pyran-4-yl)-3-(4,5,6,7-tetrahydrobenzo[d]thiazol-2-yl)-1H-pyrazole-4-carboxamide;
N-(1-methylpiperidin-4-yl)-3-(4,5,6,7-tetrahydrobenzo[d]thiazol-2-yl)-1H-pyrazole-4-carboxamide;
Tetrahydro-pyran-4-carboxylic acid (3-benzothiazol-2-yl-1H-pyrazol-4-yl)-amide;
Cyclobutanecarboxylic acid (3-benzothiazol-2-yl-1H-pyrazol-4-yl)-amide;

Acetic acid 2-(3-benzothiazol-2-yl-1H-pyrazol-4-ylcarbamoyl)-2-methyl-propyl ester;
N-(3-Benzothiazol-2-yl-1H-pyrazol-4-yl)-3-hydroxy-2,2-dimethyl-propionamide;
4-(5-Methyl-1H-benzoimidazol-2-yl)-thiazole-5-carboxylic acid tert-butylamide;
N-[3-(1H-Benzoimidazol-2-yl)-1H-pyrazol-4-yl]-isobutyramide;
N-[3-(1H-Benzoimidazol-2-yl)-1H-pyrazol-4-yl]-2,2-dimethyl-propionamide;
Cyclopentanecarboxylic acid [3-(1H-benzoimidazol-2-yl)-1H-pyrazol-4-yl]-amide;
Tetrahydro-pyran-4-carboxylic acid [3-(1H-benzoimidazol-2-yl)-1H-pyrazol-4-yl]-amide;
Acetic acid 2-[3-(1H-benzoimidazol-2-yl)-1H-pyrazol-4-yl-carbamoyl]-2-methyl-propyl ester;
N-[3-(1H-Benzoimidazol-2-yl)-1H-pyrazol-4-yl]-3-hydroxy-2,2-dimethyl-propionamide;
3-(1H-Benzoimidazol-2-yl)-1H-pyrazole-4-carboxylic acid isopropylamide;—12—case 31176

Inhibitors of SYK 3-(1H-Benzoimidazol-2-yl)-1H-pyrazole-4-carboxylic acid tert-butylamide;
3-(1H-Benzoimidazol-2-yl)-1H-pyrazole-4-carboxylic acid (tetrahydro-pyran-4-yl)-amide;
3-(1H-Benzoimidazol-2-yl)-1H-pyrazole-4-carboxylic acid (2-hydroxy-1,1-dimethyl-ethyl)-amide;
4-(4-methyl-1H-benzo[d]imidazol-2-yl)-N-(pyridin-3-yl)thiazol-5-amine;
4-(1H-imidazo[4,5-c]pyridin-2-yl)-N-(pyridin-3-yl)thiazol-5-amine;
4-(5-methyl-1H-benzo[d]imidazol-2-yl)-N-tert-pentylthiazol-5-amine;
N-cyclopentyl-4-(5-methyl-1H-benzo[d]imidazol-2-yl)thiazol-5-amine; and
N-isobutyl-4-(5-methyl-1H-benzo[d]imidazol-2-yl)thiazol-5-amine.

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

The application provides a pharmaceutical composition comprising the compound of Formula I, admixed with at least one pharmaceutically acceptable carrier, excipient or diluent.

The application provides the above pharmaceutical composition, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The application provides the use of the compound of formula I for the manufacture of a medicament useful for the treatment of disorders associated with Syk.

The application provides the use of the compound of formula I for the manufacture of a medicament useful for the treatment of rheumatoid arthritis.

A compound, method, or composition as described herein.

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system or Struct=Name, a CambridgeSoft® application, for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of compounds according to generic Formula I.

TABLE I

| Compound | Nomenclature | Structure |
| --- | --- | --- |
| I-1 | 2-Phenyl-5-(1H-pyrazol-3-yl)-thiazole | 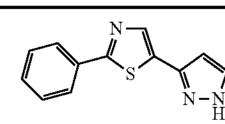 |

TABLE I-continued

| Compound | Nomenclature | Structure |
|---|---|---|
| I-2 | 3-[1,2,4]Triazolo[1,5-a]pyridin-2-yl-1H-pyrazole-4-carboxylic acid ethyl ester | 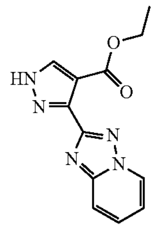 [SMILES: CCOC(=O)c1c[nH]nc1-c1nc2ccccn2n1] |
| I-3 | N-(3-Benzothiazol-2-yl-1H-pyrazol-4-yl)-isobutyramide | 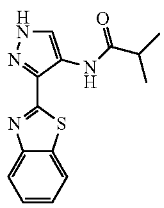 [SMILES: CC(C)C(=O)Nc1c[nH]nc1-c1nc2ccccc2s1] |
| I-4 | N-(3-Benzothiazol-2-yl-1H-pyrazol-4-yl)-2,2-dimethyl-propionamide | 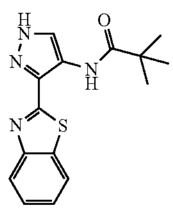 [SMILES: CC(C)(C)C(=O)Nc1c[nH]nc1-c1nc2ccccc2s1] |
| I-5 | Cyclopenanecarboxylic acid (3-benzothiazol-2-yl-1H-pyrazol-4-yl)-amide | 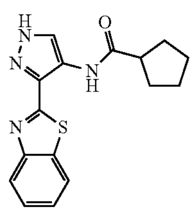 [SMILES: O=C(Nc1c[nH]nc1-c1nc2ccccc2s1)C1CCCC1] |
| I-6 | Cyclopropanecarboxylic acid (3-benzothiazol-2-yl-1H-pyrazol-4-yl)-amide | 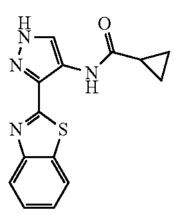 [SMILES: O=C(Nc1c[nH]nc1-c1nc2ccccc2s1)C1CC1] |
| I-7 | 3-(benzo[d]thiazol-2-yl)-N-(1-hydroxy-2-methylpropan-2-yl)-1H-pyrazole-4-carboxamide | 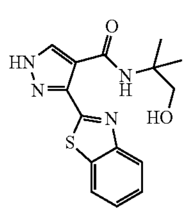 [SMILES: CC(C)(CO)NC(=O)c1c[nH]nc1-c1nc2ccccc2s1] |
| I-8 | 3-(benzo[d]thiazol-2-yl)-N-tert-butyl-1H-pyrazole-4-carboxamide | 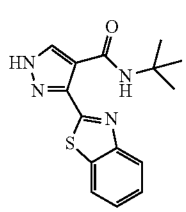 [SMILES: CC(C)(C)NC(=O)c1c[nH]nc1-c1nc2ccccc2s1] |
| I-9 | N-(1-hydroxy-2-methylpropan-2-yl)-3-(5-methylbenzo[b]thiophen-2-yl)-1H-pyrazole-4-carboxamide | |
| I-10 | N-tert-butyl-3-(5-methylbenzo[b]thiophen-2-yl)-1H-pyrazole-4-carboxamide | |
| I-11 | N-tert-butyl-3-(6-methoxypyridin-2-yl)-1H-pyrazole-4-carboxamide | |
| I-12 | (S)-3-(benzo[d]thiazol-2-yl)-N-(1-hydroxypropan-2-yl)-1H-pyrazole-4-carboxamide | |
| I-13 | ethyl 3-(4-phenylthiazol-2-yl)-1H-pyrazole-4-carboxylate | |
| I-14 | ethyl 3-(4,5,6,7-tetrahydrobenzo[d]thiazol-2-yl)-1H-pyrazole-4-carboxylate | |
| I-15 | ethyl 3-(5,6-dihydro-4H-cyclopenta[d]thiazol-2-yl)-1H-pyrazole-4-carboxylate | |

TABLE I-continued

| Compound | Nomenclature |
|---|---|
| I-16 | N-tert-butyl-3-(4-phenylthiazol-2-yl)-1H-pyrazole-4-carboxamide |
| I-17 | N-isopropyl-3-(4-phenylthiazol-2-yl)-1H-pyrazole-4-carboxamide |
| I-18 | N-tert-butyl-3-(5,6-dihydro-4H-cyclopenta[d]thiazol-2-yl)-1H-pyrazole-4-carboxamide |
| I-19 | N-tert-butyl-3-(4,5,6,7-tetrahydrobenzo[d]thiazol-2-yl)-1H-pyrazole-4-carboxamide |
| I-20 | N-cyclopentyl-3-(4-phenylthiazol-2-yl)-1H-pyrazole-4-carboxamide |
| I-21 | 3-(4-phenylthiazol-2-yl)-N-(tetrahydro-2H-pyran-4-yl)-1H-pyrazole-4-carboxamide |
| I-22 | 3-(5,6-dihydro-4H-cyclopenta[d]thiazol-2-yl)-N-(tetrahydro-2H-pyran-4-yl)-1H-pyrazole-4-carboxamide |
| I-23 | N-(tetrahydro-2H-pyran-4-yl)-3-(4,5,6,7-tetrahydrobenzo[d]thiazol-2-yl)-1H-pyrazole-4-carboxamide |
| I-24 | N-(1-methylpiperidin-4-yl)-3-(4,5,6,7-tetrahydrobenzo[d]thiazol-2-yl)-1H-pyrazole-4-carboxamide |
| I-25 | Tetrahydro-pyran-4-carboxylic acid (3-benzothiazol-2-yl-1H-pyrazol-4-yl)-amide |
| I-26 | Cyclobutanecarboxylic acid (3-benzothiazol-2-yl-1H-pyrazol-4-yl)-amide |
| I-27 | Acetic acid 2-(3-benzothiazol-2-yl-1H-pyrazol-4-ylcarbamoyl)-2-methyl-propyl ester |
| I-28 | N-(3-Benzothiazol-2-yl-1H-pyrazol-4-yl)-3-hydroxy-2,2-dimethyl-propionamide |
| I-29 | 4-(5-Methyl-1H-benzoimidazol-2-yl)-thiazole-5-carboxylic acid tert-butylamide |

TABLE I-continued

| Compound | Nomenclature | Structure |
|---|---|---|
| I-30 | N-[3-(1H-Benzoimidazol-2-yl)-1H-pyrazoll-4-yl]-isobutyramide | 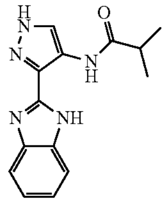 [SMILES: CC(C)C(=O)Nc1c[nH]nc1-c1nc2ccccc2[nH]1] |
| I-31 | N-[3-(1H-Benzoimidazol-2-yl)-1H-pyrazol-4-yl]-2,2-dimethyl-propionamide | 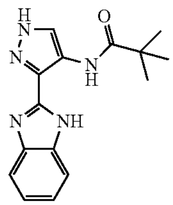 [SMILES: CC(C)(C)C(=O)Nc1c[nH]nc1-c1nc2ccccc2[nH]1] |
| I-32 | Cyclopentanecarboxylic acid [3-(1H-benzoimidazol-2-yl)-1H-pyrazol-4-yl]-amide | 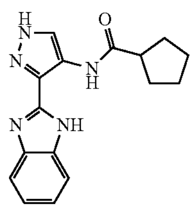 [SMILES: O=C(Nc1c[nH]nc1-c1nc2ccccc2[nH]1)C1CCCC1] |
| I-33 | Tetrahydro-pyran-4-carboxylic acid [3-(1H-benzoimidazol-2-yl)-1H-pyrazol-4-yl]-amide | 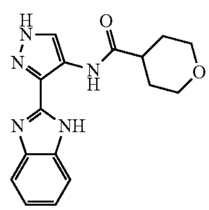 [SMILES: O=C(Nc1c[nH]nc1-c1nc2ccccc2[nH]1)C1CCOCC1] |
| I-34 | Acetic acid 2-[3-(1H-benzoimidazol-2-yl)-1H-pyrazol-4-ylcarbamoyl]-2-methyl-propyl ester | 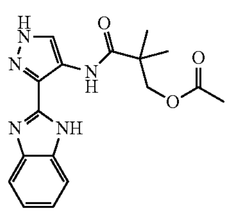 [SMILES: CC(=O)OCC(C)(C)C(=O)Nc1c[nH]nc1-c1nc2ccccc2[nH]1] |
| I-35 | N-[3-(1H-Benzoimidazol-2-yl)-1H-pyrazol-4-yl]-3-hydroxy-2,2-dimethyl-propionamide | 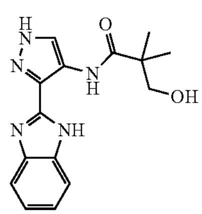 [SMILES: CC(C)(CO)C(=O)Nc1c[nH]nc1-c1nc2ccccc2[nH]1] |
| I-36 | 3-(1H-Benzoimidazol-2-yl)-1H-pyrazole-4-carboxylic acid isopropylamide | 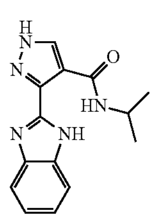 [SMILES: CC(C)NC(=O)c1c[nH]nc1-c1nc2ccccc2[nH]1] |
| I-37 | 3-(1H-Benzoimidazol-2-yl)-1H-pyrazole-4-carboxylic acid tert-butylamide | |
| I-38 | 3-(1H-Benzoimidazol-2-yl)-1H-pyrazole-4-carboxylic acid (tetrahydro-pyran-4-yl)-amide | |
| I-39 | 3-(1H-Benzoimidazol-2-yl)-1H-pyrazole-4-carboxylic acid (2-hydroxy-1,1-dimethyl-ethyl)-amide | |
| I-40 | 4-(4-methyl-1H-benzo[d]imidazol-2-yl)-N-(pyridin-3-yl)thiazol-5-amine | |
| I-41 | 4-(1H-imidazo[4,5-c]pyridin-2-yl)-N-(pyridin-3-yl)thiazol-5-amide | |
| I-42 | 4-(5-methyl-1H-benzo[d]imidazol-2-yl)-N-tert-pentylthiazol-5-amine | |
| I-43 | N-cyclopentyl-4-(5-methyl-1H-benzo[d]imidazol-2-yl)thiazol-5-amine | |

TABLE I-continued
| Compound | Nomenclature | Structure |
|---|---|---|
| I-44 | N-isobutyl-4-(5-methyl-1H-benzo[d]imidazol-2-yl)thiazol-5-amine | 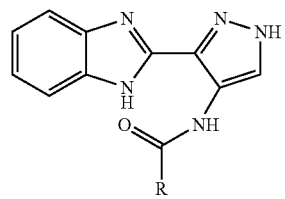 |
Synthesis
General Schemes
Scheme 1
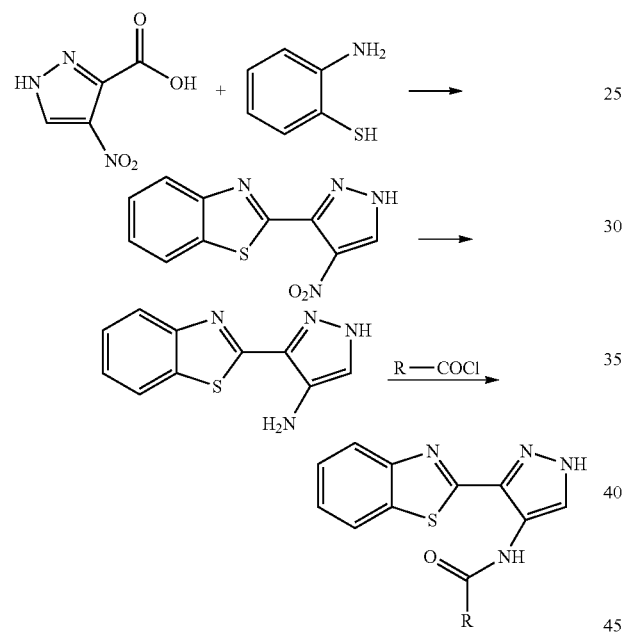
Scheme 2
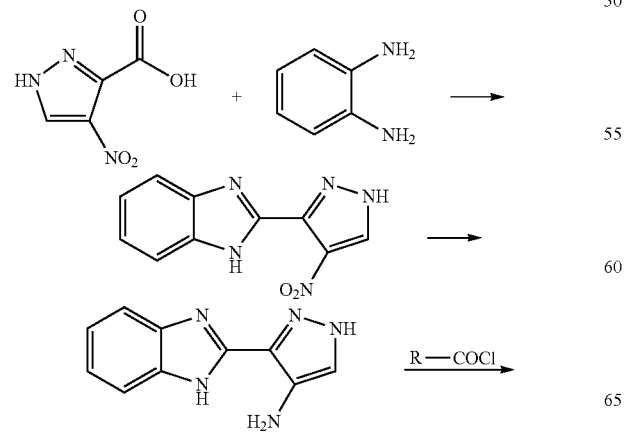
Scheme 3
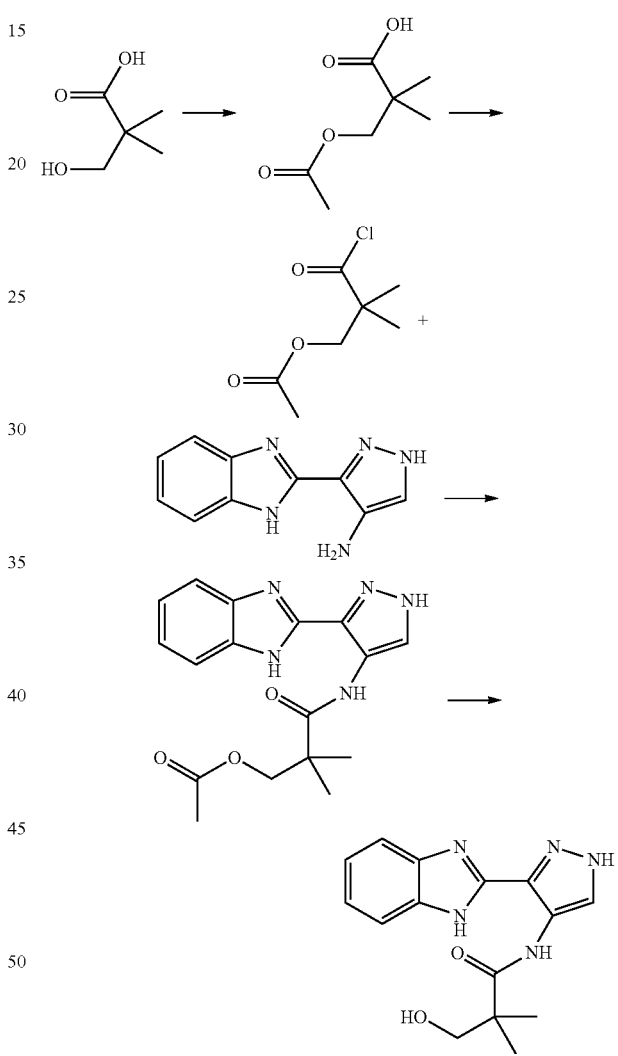
Scheme 4
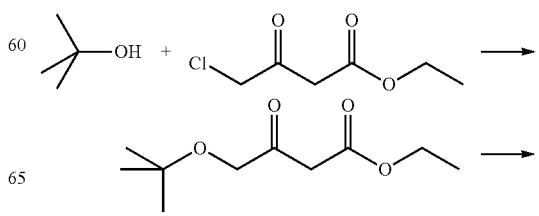

-continued

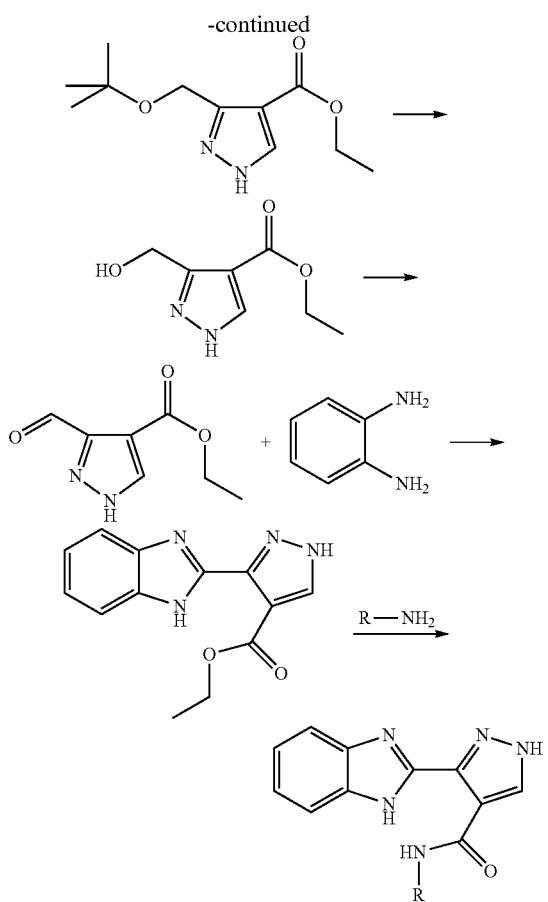

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day.

Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
| --- | --- |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | Grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 h.

Indications and Methods of Treatment

The compounds described herein are kinase inhibitors, in particular SYK inhibitors. These inhibitors can be useful for treating one or more diseases responsive to kinase inhibition, including diseases responsive to SYK inhibition and/or inhibition of B-cell proliferation, in mammals. Without wishing to be bound to any particular theory, it is believed that the interaction of the compounds of the invention with SYK results in the inhibition of SYK activity and thus in the pharmaceutical utility of these compounds. Accordingly, the invention includes a method of treating a mammal, for instance a human, having a disease responsive to inhibition of SYK activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to SYK include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

EXAMPLES

Abbreviations

Commonly used abbreviations include: acetyl (Ac), azo-bis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether (Et$_2$O), ethyl isopropyl ether (EtOiPr), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl) palladium(II) (Pd(dppf)Cl$_2$), palladium(II) acetate (Pd(OAc)$_2$), tris(dibenzylideneacetone)dipalladium(0) (Pd$_2$(dba)$_3$), pyridinium dichromate (PDC), phenyl (Ph), propyl (Pr), iso-propyl (i-Pr), pounds per square inch (psi), pyridine (pyr), 1,2,3,4,5-Pentaphenyl-1'(di-tert-butylphosphino)ferrocene (Q-Phos), room temperature (ambient temperature, rt or RT), sec-Butyllithium (sBuLi), tert-butyldimethylsilyl or t-BuMe$_2$Si (TBDMS), tetra-n-butylammonium fluoride (TBAF), triethylamine (TEA or Et$_3$N), 2,2,6,6-tetramethyl-piperidine 1-oxyl (TEMPO), triflate or CF$_3$SO$_2$-(Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

General Conditions.

Unless otherwise stated, all temperatures including melting points (i.e., MP) are in degrees Celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The preceding abbreviations may be used in the Preparations and Examples. All names were generated using Autonom or ChemDraw.

The following preparations and examples are given to enable those skilled in the art to more clearly understand and to practice the present invention. They should not be considered as limiting the scope of the invention, but merely as being illustrative and representative thereof.

Preparative Examples

Example 1

Ethyl 3-([1,2,4]triazolo[1,5-a]pyridin-2-yl)-1H-pyrazole-4-carboxylate

Step 1

Ethyl [1,2,4]triazolo[1,5-a]pyridine-2-carboxylate

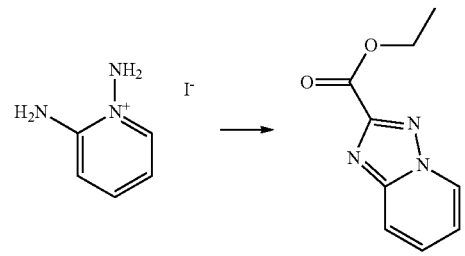

To solution of ethyl 2-ethoxy-2-iminoacete (1.91 g, 13.2 mmol) in ethanol (66.1 mL) was added 1,2-diaminopyridinium iodide (2.35 g, 9.91 mmol) followed by potassium hydroxide (556 mg, 9.91 mmol) and stirred at r.t. for 16 h. Water was then added, the mixture extracted with EtOAc, the organic layer was separated, and concentrated in vacuo. Purification by chromatography (silica, 60-100% ethyl acetate in hexanes) gave ethyl [1,2,4]triazolo[1,5-a]pyridine-2-carboxylate (570 mg, 30%). $^1$H NMR (400 MHz, CHLOROFORM-d) δ ppm 8.67 (dt, J=6.9, 1.2 Hz, 1 H), 7.86 (dt, J=9.1, 1.2 Hz, 1 H), 7.62 (m, 1 H), 7.17 (td, J=7.0, 1.3 Hz, 1 H), 4.56 (q, J=7.2 Hz, 2 H), 1.48 (t, J=7.1 Hz, 3 H).

Step 2

Ethyl 3-([1,2,4]triazolo[1,5-a]pyridin-2-yl)-3-oxo-propanoate

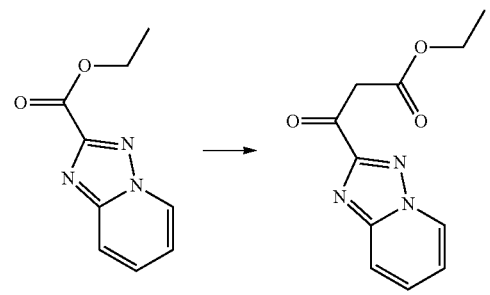 [SMILES: CCOC(=O)c1nc2ccccn2n1 ; CCOC(=O)CC(=O)c1nc2ccccn2n1]

To a mixture of ethyl [1,2,4]triazolo[1,5-a]pyridine-2-carboxylate (590 mg, 3.09 mmol) and ethyl acetate (1.81 mL, 18.5 mmol) in THF (6 mL) at −50° C. was quickly added lithium bis(trimethylsilyl)amide (1 M in toluene, 9.26 mL, 9.26 mmol). The mixture was stirred for 30 min, and then quenched with acetic acid, washed with water, sodium bicarbonate, and brine. Purification by chromatography (silica, 50-100% ethyl acetate in hexanes) gave ethyl 3-([1,2,4]triazolo[1,5-a]pyridin-2-yl)-3-oxopropanoate (350 mg, 49%) as a clear oil.

Step 3

(E)-Ethyl 2-([1,2,4]triazolo[1,5-a]pyridine-2-carbonyl)-3-(dimethylamino)acrylate

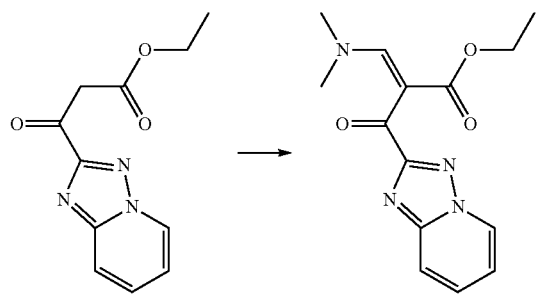 [SMILES: CCOC(=O)CC(=O)c1nc2ccccn2n1 ; CCOC(=O)/C(=C/N(C)C)C(=O)c1nc2ccccn2n1]

To a solution of ethyl 3-([1,2,4]triazolo[1,5-a]pyridin-2-yl)-3-oxopropanoate (350 mg, 1.5 mmol) in ethanol (4.3 mL) was added dimethylformamide dimethyl acetal (1.97 mg, 1.65 mmol) and the mixture heated to 80° C. for 3 h. The mixture was concentrated in vacuo, adsorbed onto silica, and purified by chromatography (silica, 1-9% methanol in dichloromethane) to give (E)-ethyl 2-([1,2,4]triazolo[1,5-a]pyridine-2-carbonyl)-3-(dimethylamino)acrylate (250 mg, 58%). $^1$H NMR (400 MHz, CHLOROFORM-d) δ ppm 8.61 (d, J=6.9 Hz, 1 H), 7.81 (s, 1 H), 7.79 (d, J=8.9 Hz, 1 H), 7.55 (t, J=7.7 Hz, 1 H), 7.08 (t, J=6.9 Hz, 1 H), 4.01 (q, J=7.3 Hz, 2 H), 3.31 (br. s, 3 H), 2.93 (br. s, 3 H), 0.88 (t, J=7.1 Hz, 3 H).

Step 4

Ethyl 3-([1,2,4]triazolo[1,5-a]pyridin-2-yl)-1H-pyrazole-4-carboxylate

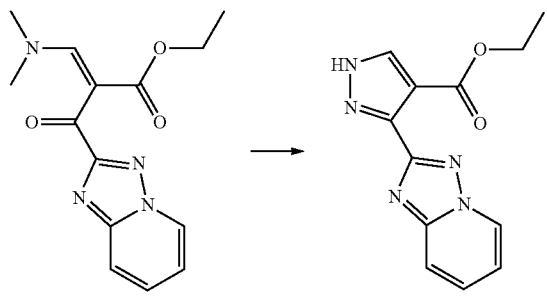 [SMILES: CCOC(=O)/C(=C/N(C)C)C(=O)c1nc2ccccn2n1 ; CCOC(=O)c1c[nH]nc1-c1nc2ccccn2n1]

To a solution of (E)-ethyl 2-([1,2,4]triazolo[1,5-a]pyridine-2-carbonyl)-3-(dimethylamino)acrylate (250 mg, 0.867 mmol) in ethanol (8.7 mL) was added hydrazine hydrate (47.3 mg, 0.954 mmol) and the resultant mixture stirred at r.t. for 2 h. The mixture was concentrated in vacuo then purified by chromatography (silica, 1-10% methanol in dichloromethane) to give ethyl 3-([1,2,4]triazolo[1,5-a]pyridin-2-yl)-1H-pyrazole-4-carboxylate (170 mg, 76%) as an off-white solid. $^1$H NMR (400 MHz, CHLOROFORM-d) δ ppm 8.76 (d, J=7.0 Hz, 1 H), 8.24 (s, 1 H), 7.90 (d, J=9.1 Hz, 1 H), 7.61 (t, J=7.9 Hz, 1 H), 7.12 (t, J=6.9 Hz, 1 H), 4.40 (q, J=7.2 Hz, 2 H), 1.39 (t, J=7.2 Hz, 3 H); MS (EI/CI) m/z: 257.9 [M+H].

Example 2

N-(3-Benzothiazol-2-yl-1H-pyrazol-4-yl)-isobutyramide

Step 1

2-(4-Nitro-1H-pyrazol-3-yl)-benzothiazole

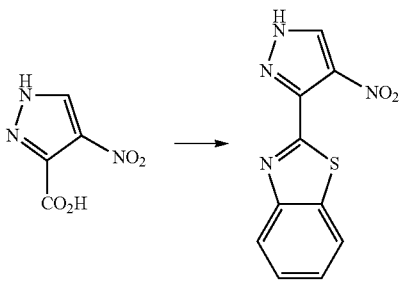 [SMILES: O=C(O)c1n[nH]cc1[N+](=O)[O-] ; O=[N+]([O-])c1c[nH]nc1-c1nc2ccccc2s1]

To a solution of 4-nitro-1H-pyrazole-3-carboxylic acid (5 g, 31.8 mmol) in THF (40 mL) was added DMF (0.25 mL, 3.19 mmol) and oxalyl chloride (4.1 mL, 47.8 mmol). The mixture was stirred at room temperature for 1 h and then concentrated under reduced pressure. The crude material was redissolved in NMP (40 mL) and 2-amino-benzenethiol (4.0 mL, 31.8 mmol) was added. This mixture was heated at 100° C. for 1 h, at which point water (100 mL) was added and the aqueous phase extracted with ethyl acetate (3×25 mL). The combined organic layers were dried (Na$_2$SO$_4$), concentrated under reduced pressure, and purified by chromatography (silica, EtOAc/hexanes) to give 2-(4-nitro-1H-pyrazol-3-yl)-benzothiazole as a light yellow solid (4.8 g, 61%). MS (EI/CI) m/z: 245.0 [M−H].

Step 2

3-Benzothiazol-2-yl-1H-pyrazol-4-ylamine

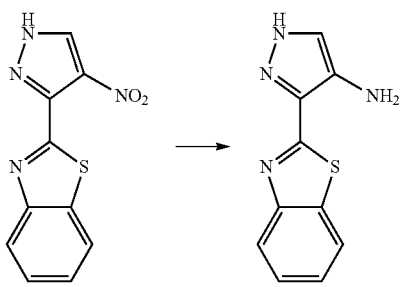 [SMILES: O=[N+]([O-])c1c[nH]nc1-c1nc2ccccc2s1 ; Nc1c[nH]nc1-c1nc2ccccc2s1]

A mixture of 2-(4-nitro-1H-pyrazol-3-yl)-benzothiazole (1.2 g, 4.87 mmol) and 10% Pd—C(50% moist) (1.7 g) in DMF (10 mL) was stirred vigorously under an atmosphere of hydrogen (balloon pressure) at room temperature for 20 h. The reaction mixture was passed through celite and the filtrate concentrated under reduced pressure. The remaining residue was partitioned between ethyl acetate and water, the organic layer separated, dried over anhydrous Na$_2$SO$_4$, and concentrated under reduced pressure to give 3-benzothiazol-2-yl-1H-pyrazol-4-ylamine as brown solid (0.76 g, 72%), which was used directly in the next step without further purification. MS (EI/CI) m/z: 217.2 [M+H].

Step 3

N-(3-Benzothiazol-2-yl-1H-pyrazol-4-yl)-isobutyramide

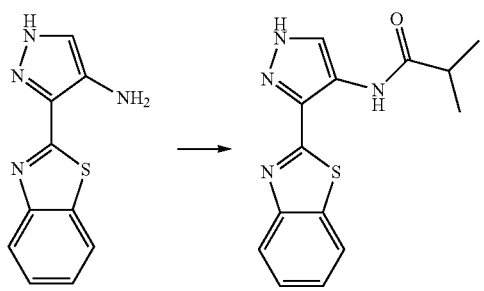 [SMILES: Nc1c[nH]nc1-c1nc2ccccc2s1 ; CC(C)C(=O)Nc1c[nH]nc1-c1nc2ccccc2s1]

N-(3-benzothiazol-2-yl-1H-pyrazol-4-yl)-isobutyramide (148.0 mg, 56%) was synthesized as light yellow solid from 3-benzothiazol-2-yl-1H-pyrazol-4-ylamine (200 mg, 0.926 mmol) and isobutyryl chloride (0.32 mL, 3.06 mmol) following the procedure described for N-[3-(1H-benzoimidazol-2-yl)-1H-pyrazol-4-yl]-isobutyramide (Example 29). MS (EI/CI) m/z: 287.1 [M+H].

Example 3

N-(3-Benzothiazol-2-yl-1H-pyrazol-4-yl)-2,2-dimethyl-propionamide

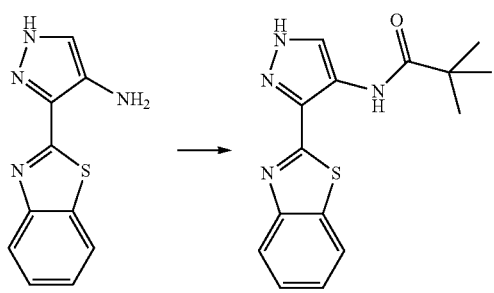 [SMILES: Nc1c[nH]nc1-c1nc2ccccc2s1 ; CC(C)(C)C(=O)Nc1c[nH]nc1-c1nc2ccccc2s1]

N-(3-benzothiazol-2-yl-1H-pyrazol-4-yl)-2,2-dimethyl-propionamide (115 mg, 41%) was synthesized as off white solid from 3-benzothiazol-2-yl-1H-pyrazol-4-ylamine (200 mg, 0.926 mmol) and pivaloyl chloride (0.38 mL, 3.056 mmol) following the procedure described for N-[3-(1H-benzoimidazol-2-yl)-1H-pyrazol-4-yl]-isobutyramide (Example 29). MS (EI/CI) m/z: 301.2 [M+H].

Example 4

Cyclopentanecarboxylic acid (3-benzothiazol-2-yl-1H-pyrazol-4-yl)-amide

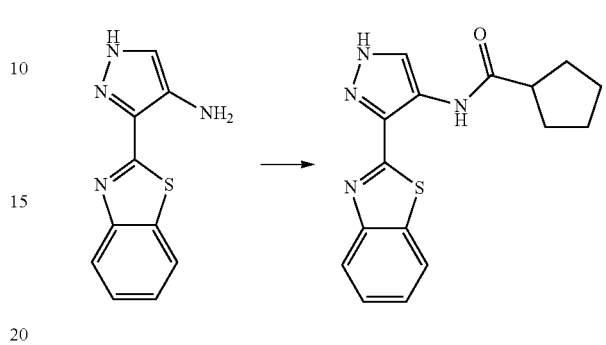

Cyclopentanecarboxylic acid (3-benzothiazol-2-yl-1H-pyrazol-4-yl)-amide (124.0 mg, 43%) was synthesized as off white solid from 3-benzothiazol-2-yl-1H-pyrazol-4-ylamine (200 mg, 0.926 mmol) and cyclopentanecarbonyl chloride (0.37 mL, 3.06 mmol) following the procedure described for N-[3-(1H-benzoimidazol-2-yl)-1H-pyrazol-4-yl]-isobutyramide (Example 29). MS (EI/CI) m/z: 313.1 [M+H].

Example 5

Cyclopropanecarboxylic acid (3-benzothiazol-2-yl-1H-pyrazol-4-yl)-amide

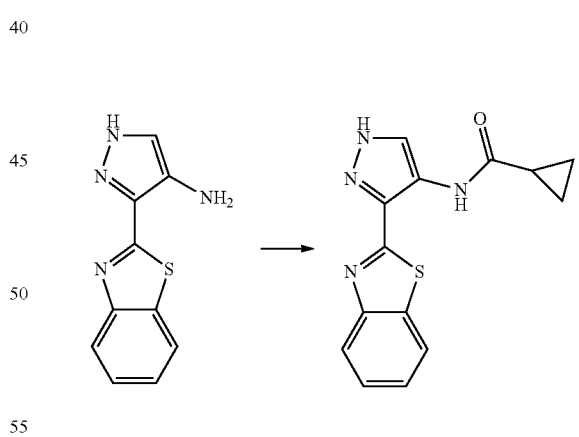

Cyclopropanecarboxylic acid (3-benzothiazol-2-yl-1H-pyrazol-4-yl)-amide (131 mg, 50%) was synthesized as an off white solid from 3-benzothiazol-2-yl-1H-pyrazol-4-ylamine (200 mg, 0.93 mmol) and cyclopropanecarbonyl chloride (0.28 mL, 3.06 mmol) following the procedure described for N-[3-(1H-benzoimidazol-2-yl)-1H-pyrazol-4-yl]-isobutyramide (Example 29). MS (EI/CI) m/z: 285.2 [M+H].

Example 6

3-(Benzo[d]thiazol-2-yl)-N-(1-hydroxy-2-methylpropan-2-yl)-1H-pyrazole-4-carboxamide

Step 1

Ethyl 3-iodo-1H-pyrazole-4-carboxylate

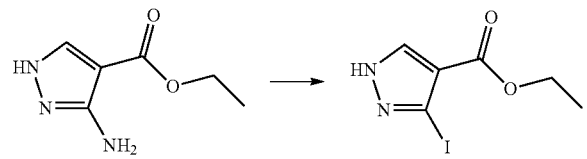

To a solution of ethyl 3-amino-1H-pyrazole-4-carboxylate (1 g, 6.45 mmol) in diiodomethane (25.9 g, 7.8 mL, 97 mmol) at −10° C. was added isoamyl nitrite (3.4 g, 3.91 mL, 29.0 mmol) dropwise over 5 min. The reaction was heated to 100° C. for 2 h, then cooled and directly purified by chromatography (silica, 0-5% methanol in dichloromethane) to give ethyl 3-iodo-1H-pyrazole-4-carboxylate (1.20 g, 4.51 mmol, 70%) as an orange solid. MS (EI/CI) m/z: 266.6 [M+H].

Step 2

Ethyl 3-iodo-1-((2-(trimethylsilyl)ethoxy)methyl)-1H-pyrazole-4-carboxylate

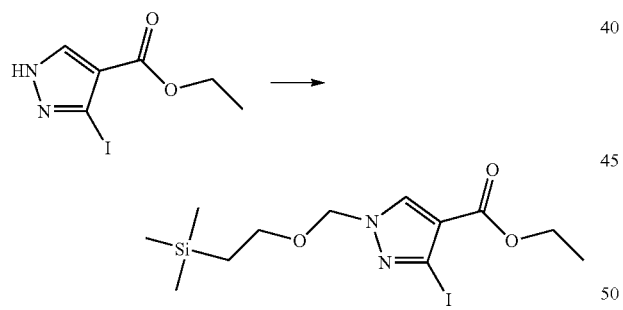

To a 0° C. solution of ethyl 3-iodo-1H-pyrazole-4-carboxylate (1.2 g, 4.51 mmol) in THF (22.4 mL) was added sodium hydride (361 mg, 9.02 mmol) and the mixture stirred for 30 min. (2-(Chloromethoxy)ethyl)trimethylsilane (902 mg, 5.41 mmol) was then added and the reaction mixture was stirred at r.t. for 16 h, quenched with sodium bicarbonate (aqueous, saturated) and extracted into ether. The combined organic solvents were concentrated in vacuo then purified by chromatography (silica, 0-15% ethyl acetate in hexanes) to give ethyl 3-iodo-1-((2-(trimethylsilyl)ethoxy)methyl)-1H-pyrazole-4-carboxylate (366 mg, 924 μmol, 21%) as a colorless liquid. $^1$H NMR (400 MHz,CHLOROFORM-d) δ ppm 7.99 (s, 1 H), 5.42 (s, 2 H), 4.34 (q, J=7.0 Hz, 2 H), 3.61 (t, J=8.5 Hz, 2 H), 1.38 (t, J=7.2 Hz, 3 H), 0.92 (t, J=8.1 Hz, 2 H), 0.01 (s, 9 H).

Step 3

Ethyl 3-(benzo[d]thiazol-2-yl)-1-((2-(trimethylsilyl)ethoxy)methyl)-1H-pyrazole-4-carboxylate

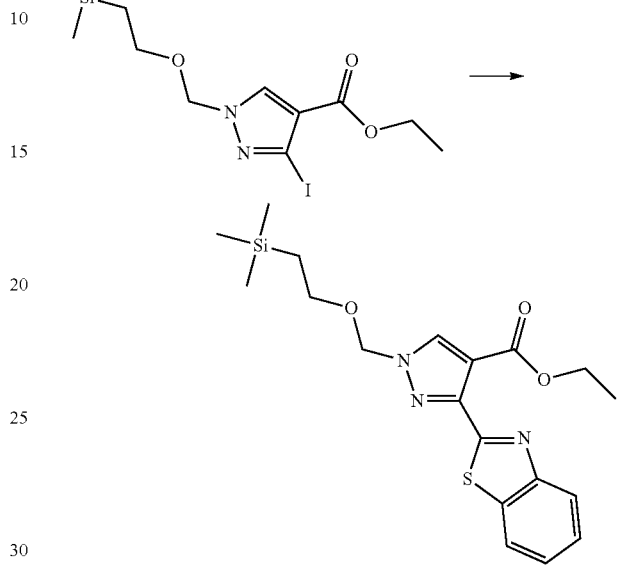

Ethyl 3-iodo-1-((2-(trimethylsilyl)ethoxy)methyl)-1H-pyrazole-4-carboxylate (239 mg, 603 μmol), 2-(tributylstannyl)benzo[d]thiazole (384 mg, 905 μmol), tetrakis(triphenylphosphine)palladium (0) (70 mg, 60 μmol) and copper (I) iodide (17 mg, 91 μmol) in dioxane (2.4 mL) and DMF (398 μL) were heated to 95° C. for 16 h. After which the mixture was cooled, concentrated in vacuo, and purified by chromatography (silica, 10-40% ethyl acetate in hexanes) to give ethyl 3-(benzo[d]thiazol-2-yl)-1-((2-(trimethylsilyl)ethoxy)methyl)-1H-pyrazole-4-carboxylate (100 mg, 248 μmol, 41%) as an off-white solid. MS (EI/CI) m/z: 404.4 [M+H].

Step 4

3-(Benzo[d]thiazol-2-yl)-1-((2-(trimethylsilyl)ethoxy)methyl)-1H-pyrazole-4-carboxylic acid

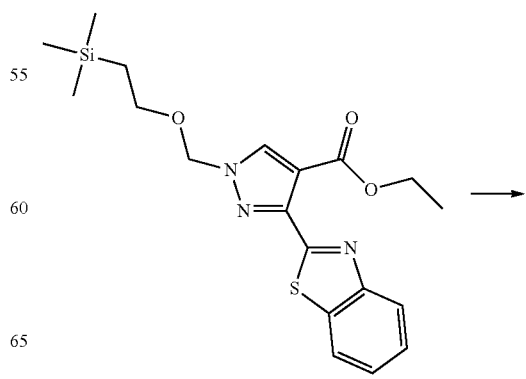

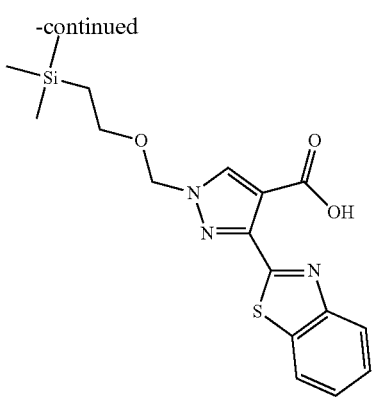

To a solution of ethyl 3-(benzo[d]thiazol-2-yl)-1-((2-(trimethylsilyl)ethoxy)methyl)-1H-pyrazole-4-carboxylate (144 mg, 357 µmol) in dioxane (5 mL) was added sodium hydroxide (1N, 1.78 mL, 1.78 mmol). The mixture was stirred at r.t. for 16 h and then quenched with 10% HCl (~pH 6), diluted with ethyl acetate and washed with water (2×). The organic layer was dried (MgSO$_4$), filtered, and concentrated in vacuo to give 3-(benzo[d]thiazol-2-yl)-1-((2-(trimethylsilyl)ethoxy)methyl)-1H-pyrazole-4-carboxylic acid (115 mg, 306 µmol, 86%) as an off white solid. MS (EI/CI) m/z: 376.1 [M+H].

Step 5

3-(Benzo[d]thiazol-2-yl)-N-(1-hydroxy-2-methyl-propan-2-yl)-1-((2-(trimethylsilyl)ethoxy)methyl)-1H-pyrazole-4-carboxamide

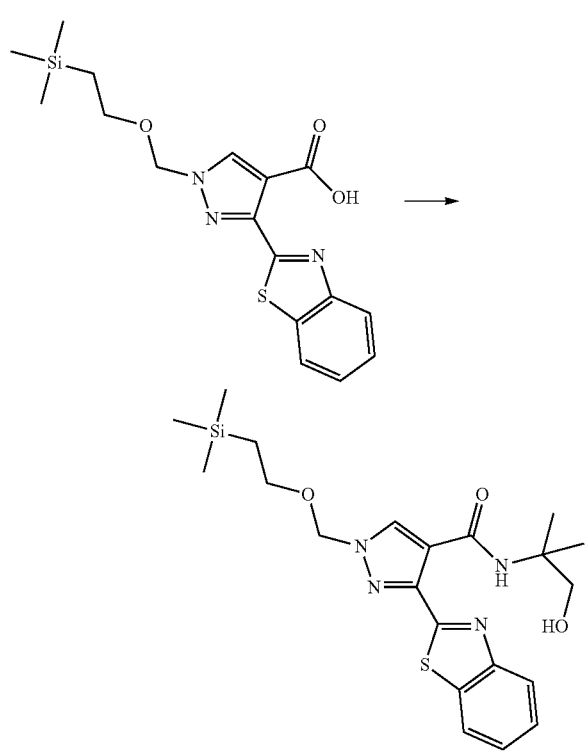

3-(Benzo[d]thiazol-2-yl)-1-((2-(trimethylsilyl)ethoxy)methyl)-1H-pyrazole-4-carboxylic acid (55 mg, 146 µmol), 2-amino-2-methylpropan-1-ol (26.1 mg, 293 µmol), HATU (66.8 mg, 176 µmol) and DIPEA (56.8 mg, 77 µL, 439 µmol) in DMF (1 mL) were stirred at r.t. for 16 h. The mixture was quenched with 10% citric acid, diluted with ethyl acetate, and the phases separated. The organic phase was washed with sodium bicarbonate and brine, then purified by chromatography (silica, 25-55% ethyl acetate in hexanes) to give 3-(benzo[d]thiazol-2-yl)-N-(1-hydroxy-2-methylpropan-2-yl)-1-((2-(trimethylsilyl)ethoxy)methyl)-1H-pyrazole-4-carboxamide (50 mg, 112 µmol, 76%) as a white solid. MS (EI/CI) m/z: 477.1 [M+H].

Step 6

3-(Benzo[d]thiazol-2-yl)-N-(1-hydroxy-2-methyl-propan-2-yl)-1H-pyrazole-4-carboxamide

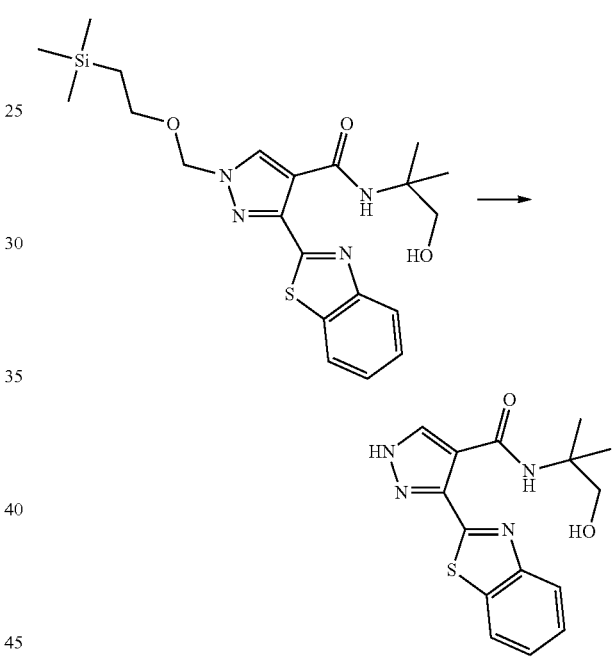

To a solution of 3-(benzo[d]thiazol-2-yl)-N-(1-hydroxy-2-methylpropan-2-yl)-1-((2-(trimethylsilyl)ethoxy)methyl)-1H-pyrazole-4-carboxamide (50 mg, 112 µmol) in dichloromethane (2 mL) was added trifluoroacetic acid (255 mg, 172 µL, 2.24 mmol). The mixture was stirred at r.t. for 16 h, and then concentrated in vacuo. To this residue was added dichloromethane (2 mL), methanol (1 mL) and ammonium hydroxide (300 µL). This mixture was stirred for an additional 2 h at r.t. and then concentrated in vacuo. The resulting residue was triturated with water, and filtered. This solid was purified by chromatography (silica, 3-7% methanol in dichloromethane) to give 3-(benzo[d]thiazol-2-yl)-N-(1-hydroxy-2-methylpropan-2-yl)-1H-pyrazole-4-carboxamide (21 mg, 66.4 µmol, 59%) as a white solid. $^1$H NMR (400 MHz, DMSO-d) δ ppm 10.61 (s, 1 H), 8.40 (s, 1 H), 8.19 (d, J=8.2 Hz, 1 H), 8.08 (d, J=8.0 Hz, 1 H), 7.62 (t, J=7.4 Hz, 1 H), 7.55 (t, J=7.5 Hz, 1 H), 5.02 (t, J=5.6 Hz, 1 H), 3.65 (d, J=8.8 Hz, 2 H), 1.46 (s, 6 H); MS (EI/CI) m/z: 317.0 [M+H].

Example 7

3-(Benzo[d]thiazol-2-yl)-N-tert-butyl-1H-pyrazole-4-carboxamide

Step 1

3-(Benzo[d]thiazol-2-yl)-1-((2-(trimethylsilyl)ethoxy)methyl)-1H-pyrazole-4-carboxylic acid

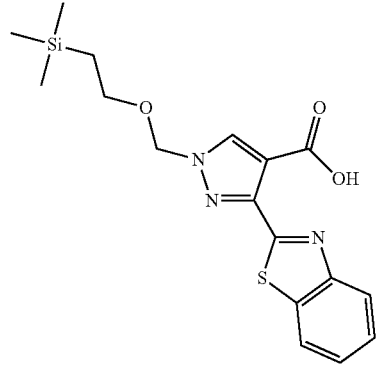

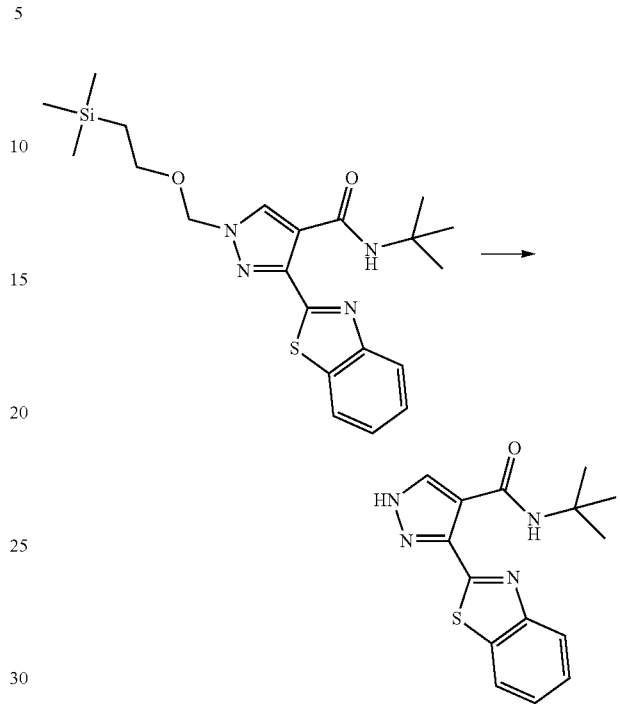

3-(Benzo[d]thiazol-2-yl)-1-((2-(trimethylsilyl)ethoxy)methyl)-1H-pyrazole-4-carboxylic acid (55 mg, 146 μmol), 2-methylpropan-2-amine (42.8 mg, 61.6 μL, 586 μmol), N1-((ethylimino)methylene)-N3,N3-dimethylpropane-1,3-diamine hydrochloride (64.6 mg, 337 μmol) and HOBT (51.6 mg, 337 μmol) were dissolved in DMF (1 mL) and stirred at r.t. for 16 h. The reaction mixture was quenched with 10% citric acid, diluted with ethyl acetate, and the phases separated. The organic phase was washed with sodium bicarbonate and brine, dried (MgSO$_4$) and evaporated. Purification by chromatography (silica, 5-30% ethyl acetate in hexanes) gave 3-(benzo[d]thiazol-2-yl)-N-tert-butyl-1-((2-(trimethylsilyl)ethoxy)methyl)-1H-pyrazole-4-carboxamide (12 mg, 27.9 μmol, 19%). $^1$H NMR (400 MHz, CHLOROFORM-d) δ ppm 10.90 (s, 1 H), 8.37 (s, 1 H), 7.98 (d, J=7.0 Hz, 1 H), 7.94 (d, J=7.6 Hz, 1 H), 7.52 (t, J=7.0 Hz, 1 H), 7.46 (t, J=7.6 Hz, 1 H), 5.48 (s, 2 H), 3.65 (t, J=8.3 Hz, 2 H), 1.61 (s, 9 H), 0.96 (t, J=8.8 Hz, 2 H), 0.01 (s, 9 H).

Step 2

3-(Benzo[d]thiazol-2-yl)-N-tert-butyl-1H-pyrazole-4-carboxamide

To a solution of 3-(benzo[d]thiazol-2-yl)-N-tert-butyl-1-((2-(trimethylsilyl)ethoxy)methyl)-1H-pyrazole-4-carboxamide (12 mg, 27.9 μmol) in dichloromethane (0.4 mL) was added trifluoroacetic acid (63.5 mg, 42.9 μL, 557 μmol). The mixture was stirred at r.t. for 16 h then concentrated in vacuo. Dichloromethane (0.5 mL), methanol (0.25 mL) and ammonium hydroxide (0.1 mL) were then added and the mixture was stirred at r.t for an additional 2 h. The mixture was concentrated in vacuo then purified by chromatography (silica, 2.5-5% methanol in dichloromethane) to give 3-(benzo[d]thiazol-2-yl)-N-tert-butyl-1H-pyrazole-4-carboxamide (6 mg, 20.0 μmol, 72%) as a white solid. $^1$H NMR (400 MHz, CHLOROFORM-d) δ ppm 11.07 (s, 1 H), 8.20 (s, 1 H), 7.94 (d, J=8.4 Hz, 1 H), 7.91 (d, J=7.4 Hz, 1 H), 7.48 (t, J=7.1 Hz, 1 H), 7.42 (t, J=7.4 Hz, 1 H), 1.56 (s, 9 H); MS (EI/CI) m/z: 300.8 [M+H].

Example 8

N-(1-Hydroxy-2-methylpropan-2-yl)-3-(5-methylbenzo[b]thiophen-2-yl)-1H-pyrazole-4-carboxamide

Step 1

Ethyl 3-(5-methylbenzo[b]thiophen-2-yl)-1-((2-(trimethylsilyl)ethoxy)methyl)-1H-pyrazole-4-carboxylate

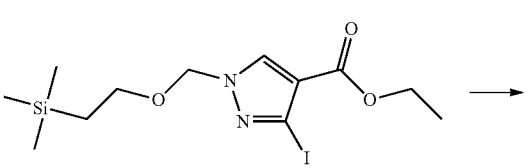

-continued

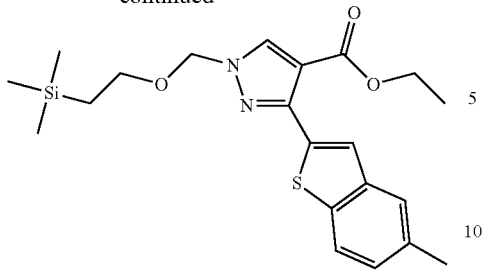

Ethyl 3-iodo-1-((2-(trimethylsilyl)ethoxy)methyl)-1H-pyrazole-4-carboxylate (366 mg, 924 μmol), 5-methylbenzo[b]thiophen-2-ylboronic acid (231 mg, 1.2 mmol), tetrakis(triphenylphosphine)palladium (0) (107 mg, 92.4 μmol) and potassium carbonate (383 mg, 2.77 mmol) in dioxane (16.4 mL) and water (4.1 mL) were heated to 90° C. for 16 h under nitrogen. The mixture was cooled and then concentrated in vacuo. Purification by chromatography (silica, 5-25% ethyl acetate in hexanes) gave ethyl 3-(5-methylbenzo[b]thiophen-2-yl)-1-((2-(trimethylsilyl)ethoxy)methyl)-1H-pyrazole-4-carboxylate (325 mg, 624 μmol, 68%) as an off-white solid. $^1$H NMR (400 MHz, CHLOROFORM-d) δ ppm 8.38 (s, 1 H), 8.16 (s, 1 H), 7.70 (d, J=8.5 Hz, 1 H), 7.61 (s, 1 H), 7.16 (dd, J=8.0, 1.1 Hz, 1 H), 5.45 (s, 2 H), 4.35 (q, J=7.0 Hz, 2 H), 3.68 (t, J=8.3 Hz, 2 H), 2.45 (s, 3 H), 1.39 (t, J=6.8 Hz, 3 H), 0.95 (t, J=8.2 Hz, 2 H), 0.01 (s, 9 H).

Step 2

3-(5-Methylbenzo[b]thiophen-2-yl)-1-((2-(trimethylsilyl)ethoxy)methyl)-1H-pyrazole-4-carboxylic acid

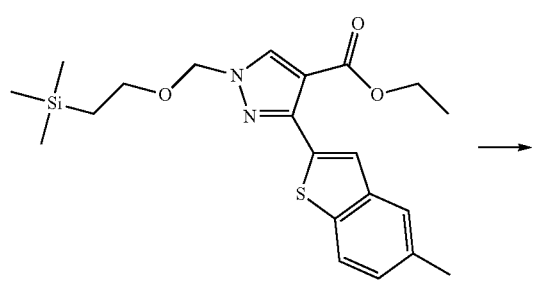

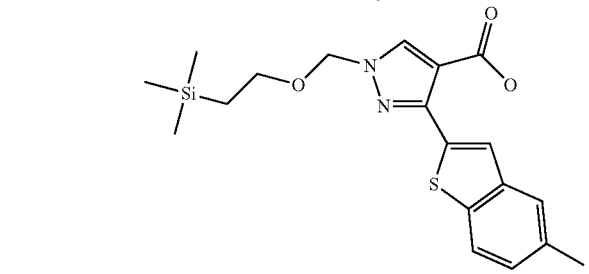

To a solution of ethyl 3-(5-methylbenzo[b]thiophen-2-yl)-1-((2-(trimethylsilyl)ethoxy)methyl)-1H-pyrazole-4-carboxylate (325 mg, 780 μmol) in dioxane (11.1 mL) was added sodium hydroxide (1N, 3.9 mL, 3.9 mmol). The mixture was stirred at r.t. for 16 h, then quenched with 10% HCl (~pH 6) and diluted with ethyl acetate and water. The organic phase was separated washed with water (2×), then concentrated in vacuo. Purification by chromatography (silica, 20-50% ethyl acetate in hexanes) gave 3-(5-methylbenzo[b]thiophen-2-yl)-1-((2-(trimethylsilyl)ethoxy)methyl)-1H-pyrazole-4-carboxylic acid (185 mg, 476 μmol, 61%) as a white solid. MS (EI/CI) m/z: 389.0 [M+H].

Step 3

N-(1-Hydroxy-2-methylpropan-2-yl)-3-(5-methylbenzo[b]thiophen-2-yl)-1-((2 (trimethylsilyl)ethoxy)methyl)-1H-pyrazole-4-carboxamide

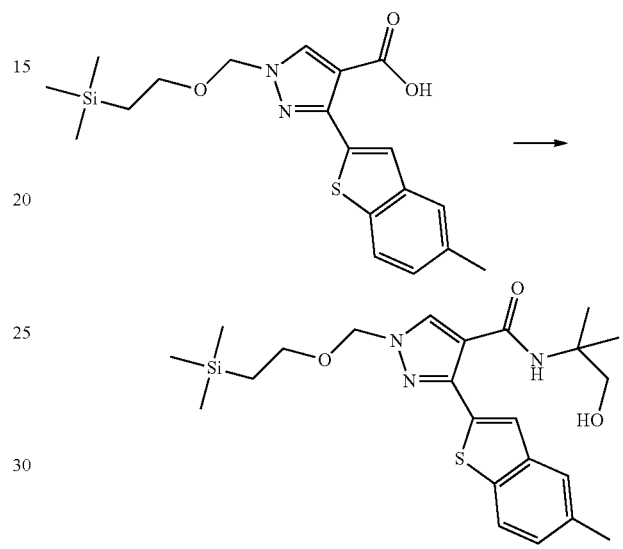

3-(5-Methylbenzo[b]thiophen-2-yl)-1-((2-(trimethylsilyl)ethoxy)methyl)-1H-pyrazole-4-carboxylic acid (90 mg, 232 μmol, 2-amino-2-methylpropan-1-ol (41.3 mg, 463 μmol), HATU (106 mg, 278 μmol) and DIPEA (89.8 mg, 121 μL, 695 μmol) in DMF (1.5 mL) were stirred at r.t. for 16 h. The reaction mixture was then quenched with 10% citric acid and diluted with ethyl acetate. The organic phase was separated, washed with sodium bicarbonate and brine, concentrated in vacuo, and then purified by chromatography (silica, 25-90% ethyl acetate in hexanes) to give N-(1-hydroxy-2-methylpropan-2-yl)-3-(5-methylbenzo[b]thiophen-2-yl)-1-((2-(trimethylsilyl)ethoxy)methyl)-1H-pyrazole-4-carboxamide (83 mg, 181 μmol, 78%) as a white solid. MS (EI/CI) m/z: 460.1 [M+H].

Step 4

N-(1-Hydroxy-2-methylpropan-2-yl)-3-(5-methylbenzo[b]thiophen-2-yl)-1H-pyrazole-4-carboxamide

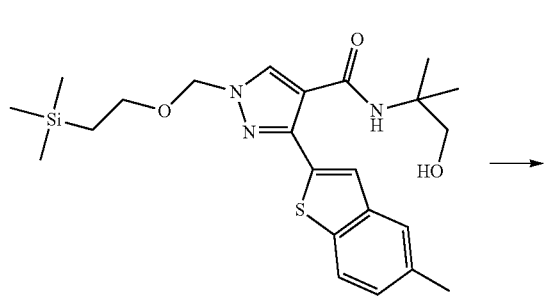

-continued

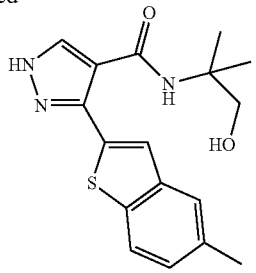

To a solution of N-(1-hydroxy-2-methylpropan-2-yl)-3-(5-methylbenzo[b]thiophen-2-yl)-1-((2-(trimethylsilyl)ethoxy)methyl)-1H-pyrazole-4-carboxamide (83 mg, 181 μmol) in dichloromethane (2.8 mL) was added trifluoroacetic acid (412 mg, 278 μL, 3.61 mmol). The mixture was stirred at r.t. for 16 h, then concentrated in vacuo. The residue obtained was redissolved in dichloromethane (2.8 mL), methanol (1.4 mL) and ammonium hydroxide (350 μL) and stirred at r.t. for 1 h. This mixture was concentrated in vacuo and the residue purified by chromatography (silica, 60-100% ethyl acetate in hexanes to give N-(1-hydroxy-2-methylpropan-2-yl)-3-(5-methylbenzo[b]thiophen-2-yl)-1H-pyrazole-4-carboxamide (17 mg, 51.6 μmol, 29%) as a white solid. $^1$H NMR (400 MHz, CHLOROFORM-d) δ ppm 7.98 (s, 1 H), 7.67 (d, J=8.0 Hz, 1 H), 7.59 (s, 1 H), 7.53 (s, 1 H), 7.16 (d, J=8.4 Hz, 1 H), 6.07 (s, 1 H), 3.58 (s, 2 H), 2.41 (s, 3 H), 1.18 (s, 6 H).; MS (EI/CI) m/z: 329.9 [M+H].

Example 9

N-tert-Butyl-3-(5-methylbenzo[b]thiophen-2-yl)-1H-pyrazole-4-carboxamide

Step 1

N-tert-Butyl-3-(5-methylbenzo[b]thiophen-2-yl)-1-((2-(trimethylsilyl)ethoxy)methyl)-1H-pyrazole-4-carboxamide

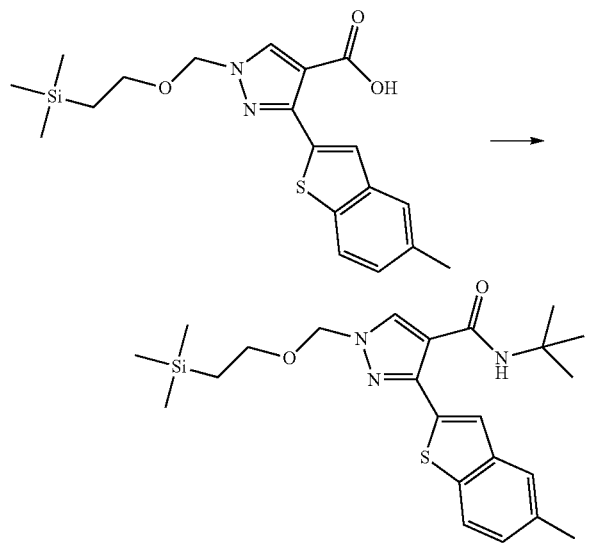

3-(5-Methylbenzo[b]thiophen-2-yl)-1-((2-(trimethylsilyl)ethoxy)methyl)-1H-pyrazole-4-carboxylic acid (90 mg, 232 μmol), 2-methylpropan-2-amine (67.8 mg, 97.4 μl, 927 μmol), N1-((ethylimino)methylene)-N3,N3-dimethylpropane-1,3-diamine hydrochloride (102 mg, 533 μmol) and HOBT (81.6 mg, 533 μmol) were dissolved in DMF (1 mL) and stirred at r.t. for 16 h. The reaction mixture was quenched with 10% citric acid and then diluted with ethyl acetate. The organic phase was separated and washed with sodium bicarbonate and brine. The organic layer was collected, concentrated in vacuo, and purified by chromatography (silica, 5-25% ethyl acetate in hexanes) to give N-tert-butyl-3-(5-methylbenzo[b]thiophen-2-yl)-1-((2-(trimethylsilyl)ethoxy)methyl)-1H-pyrazole-4-carboxamide (72 mg, 162 μmol, 70%) as a colorless oil. $^1$H NMR (400 MHz, CHLOROFORM-d) δ ppm 8.03 (s, 1 H), 7.73 (d, J=8.6 Hz, 1 H), 7.66 (s, 1 H), 7.59 (s, 1 H), 7.20 (d, J=8.1 Hz, 1 H), 5.91 (s, 1 H), 5.44 (s, 2 H), 3.64 (t, J=8.2 Hz, 2 H), 2.47 (s, 3 H), 1.35 (s, 9 H), 0.95 (t, J=8.6 Hz, 2 H), 0.01 (s, 9 H).

Step 2

N-text-Butyl-3-(5-methylbenzo[b]thiophen-2-yl)-1H-pyrazole-4-carboxamide

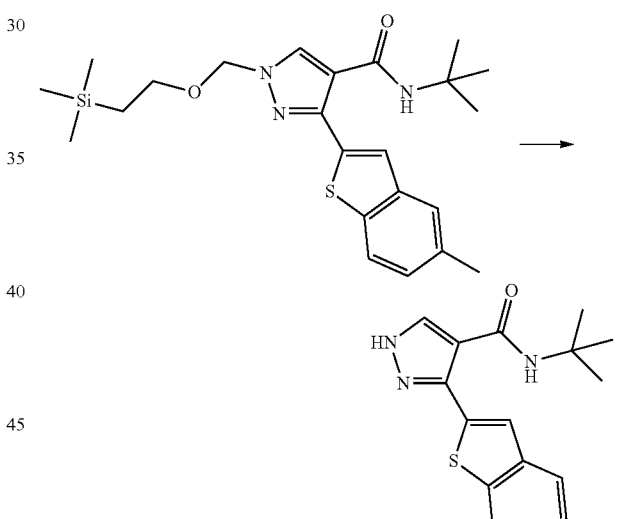

To a solution of N-tert-butyl-3-(5-methylbenzo[b]thiophen-2-yl)-1-((2-(trimethylsilyl)ethoxy)methyl)-1H-pyrazole-4-carboxamide (72 mg, 162 μmol) in dichloromethane (2.5 mL) was added trifluoroacetic acid (370 mg, 250 μL, 3.25 mmol). The mixture was stirred at r.t for 16 h and then concentrated in vacuo. The residue obtained was redissolved in dichloromethane (2.5 mL), methanol (1.3 mL) and ammonium hydroxide (350 μL) and stirred at r.t for 1 h. The mixture was then concentrated in vacuo and purified by chromatography (silica, 40-80% ethyl acetate in hexanes) to give N-tert-butyl-3-(5-methylbenzo[b]thiophen-2-yl)-1H-pyrazole-4-carboxamide (18 mg, 57.4 μmol, 35%) as a white solid. $^1$H NMR (400 MHz, CHLOROFORM-d) δ ppm 8.04 (s, 1 H), 7.76 (d, J=8.2 Hz, 1 H), 7.71 (s, 1 H), 7.63 (s, 1 H), 7.24 (d, J=8.5 Hz, 1 H), 5.92 (s, 1 H), 2.51 (s, 3 H), 1.39 (s, 9 H); MS (EI/CI) m/z: 313.9 [M+H].

Example 10

N-tert-Butyl-3-(6-methoxypyridin-2-yl)-1H-pyrazole-4-carboxamide

Step 1

Ethyl 3-(6-methoxypyridin-2-yl)-3-oxopropanoate

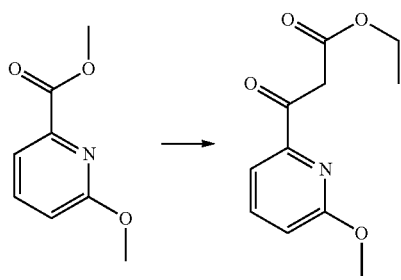 [SMILES: COC(=O)c1cccc(OC)n1 ; CCOC(=O)CC(=O)c1cccc(OC)n1]

To a mixture of methyl 6-methoxypicolinate (200 mg, 1.2 mmol) and ethyl acetate (0.70 mL, 7.18 mmol) in THF (2.4 mL) at −50° C. was quickly added lithium bis(trimethylsilyl)amide (1 M in toluene, 3.6 mL, 3.6 mmol). The mixture was stirred for 30 min, then quenched with acetic acid, and washed with sodium bicarbonate. The organic phase was concentrated in vacuo and purified by chromatography (silica, 10-40% ethyl acetate in hexanes) to give ethyl 3-(6-methoxypyridin-2-yl)-3-oxopropanoate (184 mg, 69%) as a clear oil. $^1$H NMR (400 MHz, CHLOROFORM-d) δ ppm 7.73 (m, 2 H), 6.99 (d, J=8.2 Hz, 1 H), 4.21 (q, J=7.2 Hz, 2 H), 4.11 (s, 2 H), 3.98 (s, 3 H), 1.24 (t, J=7.1 Hz, 3 H).

Step 2

(E)-Ethyl 3-ethoxy-2-(6-methoxypicolinoyl)acrylate

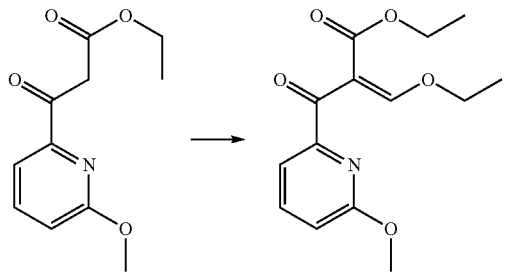 [SMILES: CCOC(=O)CC(=O)c1cccc(OC)n1 ; CCO/C=C(\C(=O)OCC)C(=O)c1cccc(OC)n1]

Ethyl 3-(6-methoxypyridin-2-yl)-3-oxopropanoate (184 mg, 824 μmol), acetic anhydride (337 mg, 3.3 mmol) and triethyl orthoformate (224 mg, 1.65 mmol) were heated to 110° C. for 6 hours. After which the mixture was cooled and concentrated to give crude (E)-ethyl 3-ethoxy-2-(6-methoxypicolinoyl)acrylate (230 mg) which was used directly in the next step without purification. MS (EI/CI) m/z: 279.8 [M+H].

Step 3

Ethyl 3-(6-methoxypyridin-2-yl)-1H-pyrazole-4-carboxylate

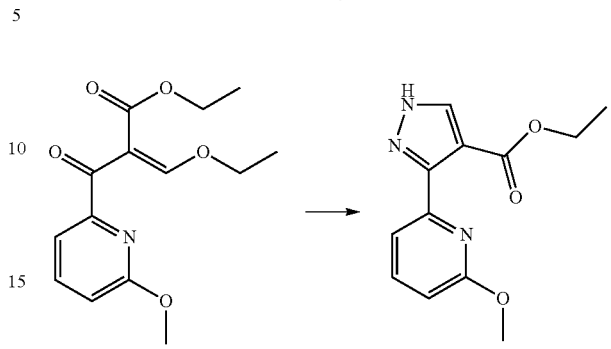

To a solution of crude (E)-ethyl 3-ethoxy-2-(6-methoxypicolinoyl)acrylate (230 mg, 824 μmol) in ethanol was added hydrazine hydrate (82.5 mg, 1.65 mmol). The mixture was stirred for 72 h, concentrated in vacuo, and then purified by chromatography (silica, 15-50% ethyl acetate in hexanes) to give ethyl 3-(6-methoxypyridin-2-yl)-1H-pyrazole-4-carboxylate (100 mg, 49% over two steps) as a white solid (over two steps). MS (EI/CI) m/z: 248.2 [M+H].

Step 4

3-(6-Methoxypyridin-2-yl)-1-((2-(trimethylsilyl)ethoxy)methyl)-1H-pyrazole-4-carboxylic acid

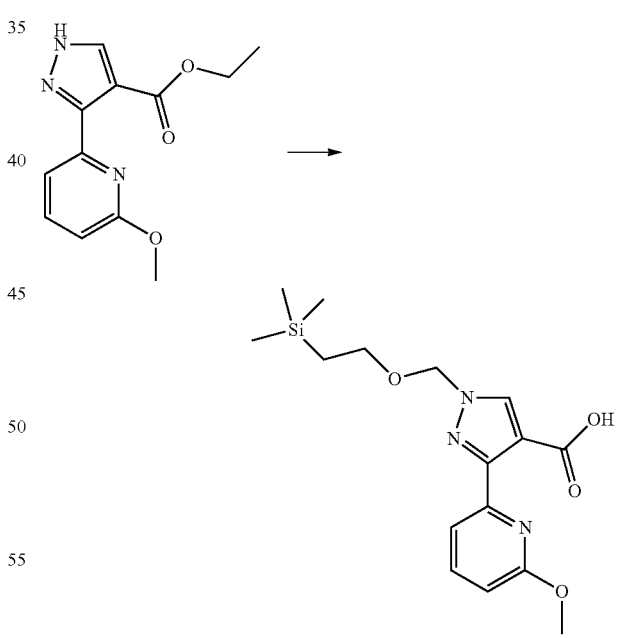

To a solution of ethyl 3-(6-methoxypyridin-2-yl)-1H-pyrazole-4-carboxylate (100 mg, 404 μmol) in THF (2 mL) cooled to 0° C. was added sodium hydride (32.4 mg, 809 μmol). The mixture was stirred for 15 min, at which point (2-(Chloromethoxy)ethyl)trimethylsilane (80.9 mg, 485 μmol) was added. After stirring at r.t. for 16 h the mixture was diluted with ethyl acetate and sodium bicarbonate, the phases separated, and the aqueous phase extracted with ethyl acetate. The combined organic layers were washed with water, separated, concentrated in vacuo, and purified by chromatography (silica, 0-50% ethyl acetate in hexanes) to give 3-(6-methoxypyridin-2-yl)-1-((2-(trimethylsilyl)ethoxy)methyl)-1H-pyrazole-4-carboxylic acid (54 mg, 155 μmol, 38%) as a white solid. MS (EI/CI) m/z: 349.9 [M+H].

Step 5

N-tert-Butyl-3-(6-methoxypyridin-2-yl)-1-((2-(trimethylsilyl)ethoxy)methyl)-1H-pyrazole-4-carboxamide 3-(6-Methoxypyridin-2-yl)-1-((2-(trimethylsilyl)ethoxy)methyl)-1H-pyrazole-4-carboxylic acid (54 mg, 155 μmol), 2-methylpropan-2-amine (45.2 mg, 618 μmol), N1-((ethylimino)methylene)-N3,N3-dimethylpropane-1,3-diamine hydrochloride (68.1 mg, 355 μmol) and 1H-benzo[d][1,2,3]triazol-1-ol hydrate (54.4 mg, 355 μmol) in DMF (1 mL) were stirred at r.t. for 16 h. The mixture was then quenched with 10% citric acid and diluted with ethyl acetate. The phases were separated and the organic layer washed with sodium bicarbonate and brine, then concentrated in vacuo and purified by chromatography (silica, 5-30% ethyl acetate in hexanes) to give N-tert-butyl-3-(6-methoxypyridin-2-yl)-1-((2-(trimethylsilyl)ethoxy)methyl)-1H-pyrazole-4-carboxamide (53 mg, 131 μmol, 85%) as a white solid. MS (EI/CI) m/z: 405.1 [M+H].

Step 6

N-tert-Butyl-3-(6-methoxypyridin-2-yl)-1H-pyrazole-4-carboxamide

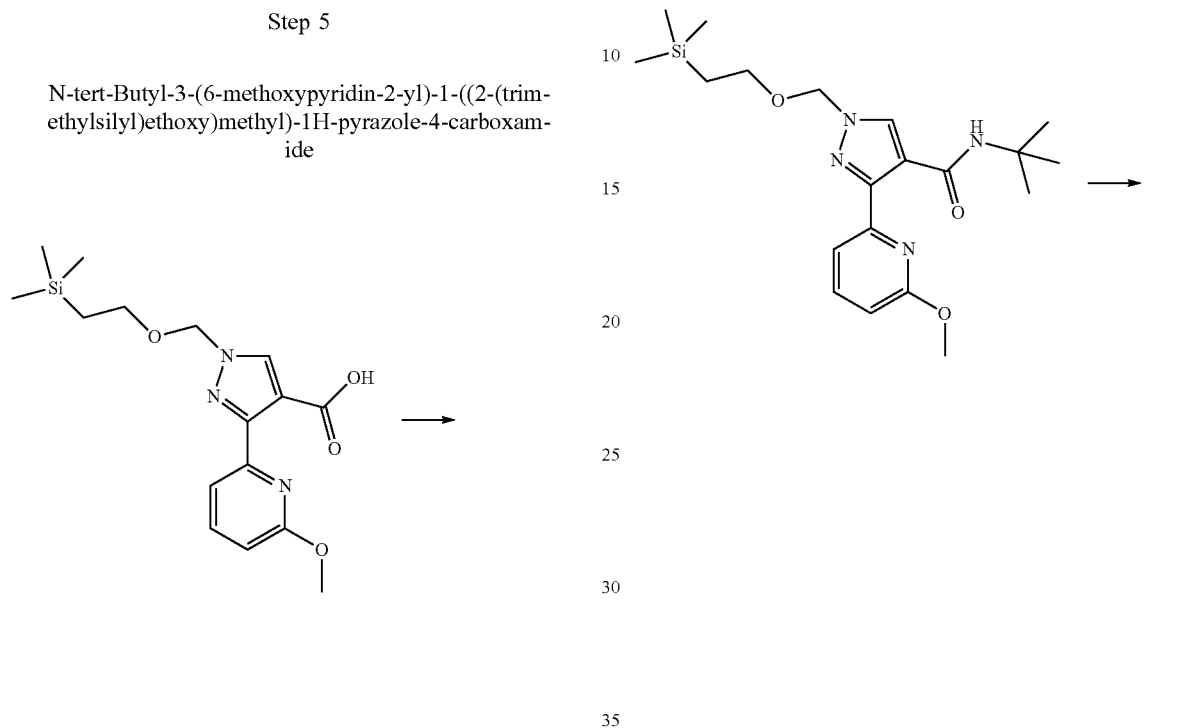

To a solution of N-tert-butyl-3-(6-methoxypyridin-2-yl)-1-((2-(trimethylsilyl)ethoxy)methyl)-1H-pyrazole-4-carboxamide (53 mg, 131 μmol) in dichloromethane (2 mL) was added trifluoroacetic acid (299 mg, 202 μL, 2.62 mmol). The mixture was stirred at r.t. for 16 h, then concentrated in vacuo. The residue obtained was redissolved in dichloromethane (2 mL), methanol (1 mL) and ammonium hydroxide (300 μL, and stirred at r.t. for 1 h. The mixture was concentrated in vacuo and purified by chromatography (silica, 40-80% ethyl acetate in hexanes) to give N-tert-butyl-3-(6-methoxypyridin-2-yl)-1H-pyrazole-4-carboxamide (27 mg, 98.4 μmol, 75%) as a white solid. $^1$H NMR (400 MHz, CHLOROFORM-d) δ ppm 13.35 (s, 1 H), 9.77 (s, 1 H), 8.19 (s, 1 H), 7.91 (t, J=7.8 Hz, 1 H), 7.63 (d, J=7.7 Hz, 1 H), 6.95 (d, J=8.0 Hz, 1 H), 3.90 (s, 3 H), 1.38 (s, 9 H); MS (EI/CI) m/z: 274.8 [M+H].

Example 11

(S)-3-(Benzo[d]thiazol-2-yl)-N-(1-hydroxypropan-2-yl)-1H-pyrazole-4-carboxamide

Step 1

(S)-3-(Benzo[d]thiazol-2-yl)-N-(1-hydroxypropan-2-yl)-1-((2-(trimethylsilyl)ethoxy)methyl)-1H-pyrazole-4-carboxamide

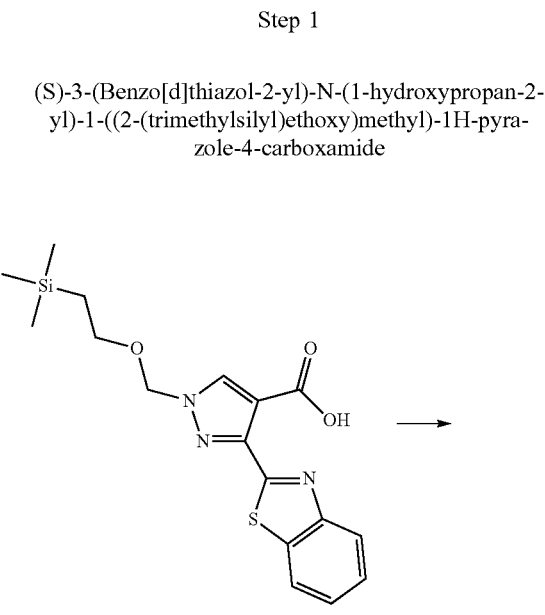

3-(Benzo[d]thiazol-2-yl)-1-((2-(trimethylsilyl)ethoxy)methyl)-1H-pyrazole-4-carboxylic acid (72 mg, 192 μmol), (S)-2-aminopropan-1-ol (57.6 mg, 767 μmol), 1-(3-dimethylaminopropyl)-3-ethylcarbodiimide hydrochloride (84.5 mg, 441 μmol) and HOBT (67.5 mg, 441 μmol) in DMF (1 mL) were stirred at r.t. for 16 h. The mixture was quenched with 10% citric acid and diluted with sodium bicarbonate and ethyl acetate. The phases were separated and the organic phase then washed with sodium bicarbonate and brine, concentrated in vacuo. Purification by chromatography (silica, 20-80% ethyl acetate in hexanes) gave (S)-3-(benzo[d]thiazol-2-yl)-N-(1-hydroxypropan-2-yl)-1-((2-(trimethylsilyl)ethoxy)methyl)-1H-pyrazole-4-carboxamide (48 mg, 111 μmol, 58%) as a colorless viscous oil. MS (EI/CI) m/z: 433.0 [M+H].

Step 2

(S)-3-(Benzo[d]thiazol-2-yl)-N-(1-hydroxypropan-2-yl)-1H-pyrazole-4-carboxamide

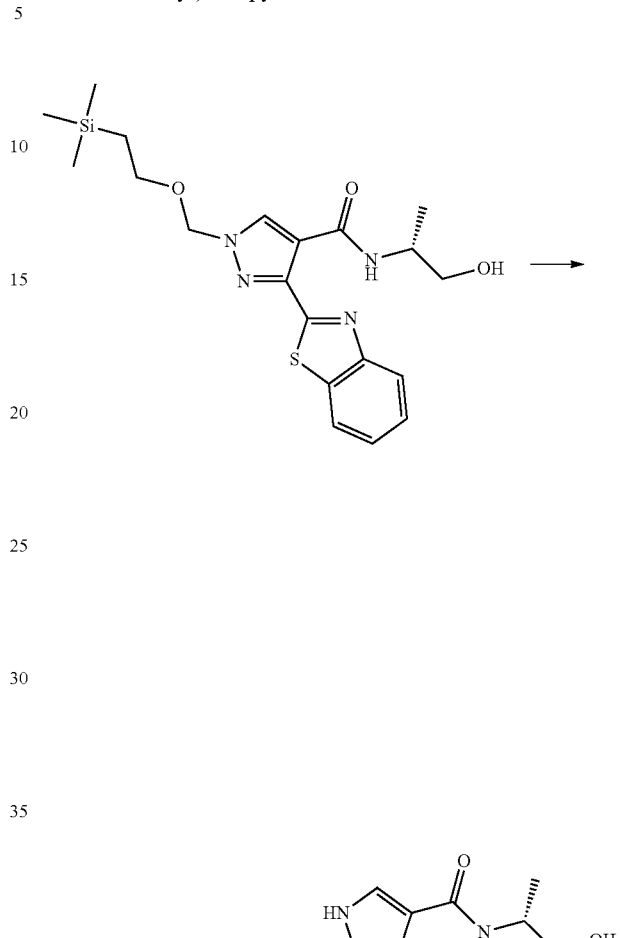

To a solution of (S)-3-(benzo[d]thiazol-2-yl)-N-(1-hydroxypropan-2-yl)-1-((2-(trimethylsilyl)ethoxy)methyl)-1H-pyrazole-4-carboxamide (48 mg, 111 μmol) in dichloromethane (1.7 mL) was added trifluoroacetic acid (253 mg, 171 μL, 2.22 mmol). The mixture was stirred at r.t. for 16 h, and then concentrated in vacuo. The residue obtained was redissolved in dichloromethane (1.7 mL), methanol (800 μL) and ammonium hydroxide (300 μL) and stirred at r.t. for 1 h. The mixture was then concentrated in vacuo, and the residue obtained triturated with water and filtered. The obtained solid was washed with water and then dried under vacuum to give (S)-3-(benzo[d]thiazol-2-yl)-N-(1-hydroxypropan-2-yl)-1H-pyrazole-4-carboxamide (28 mg, 92.6 μmol, 84%) as a white solid. $^1$H NMR (400 MHz, CHLOROFORM-d) δ ppm 13.87 (s, 1 H), 10.88 (s, 1 H), 8.44 (s, 1 H), 8.18 (d, J=8.1 Hz, 1 H), 8.10 (d, J=8.0 Hz, 1 H), 7.60 (t, J=7.5 Hz, 1 H), 7.53 (t, J=7.7 Hz, 1 H), 4.93 (t, J=6.0 Hz, 1 H), 4.07 (m, 1 H), 3.61 (m, 1 H), 3.52 (m, 1 H), 1.29 (d, J=6.7 Hz, 3 H); MS (EI/CI) m/z: 302.8 [M+H].

Example 12

Ethyl 3-(4-phenylthiazol-2-yl)-1H-pyrazole-4-carboxylate

Step 1

Ethyl 3-oxo-3-(4-phenylthiazol-2-yl)propanoate

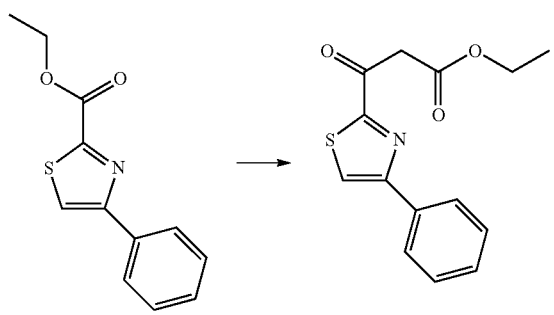 [SMILES: CCOC(=O)c1nc(-c2ccccc2)cs1 ; CCOC(=O)CC(=O)c1nc(-c2ccccc2)cs1]

To a solution of ethyl 4-phenylthiazole-2-carboxylate (900 mg, 3.86 mmol) and ethyl acetate (2.27 mL, 23.1 mmol) in THF (8 mL) cooled to −50° C. was quickly added lithium bis(trimethylsilyl)amide (1 M in toluene, 11.6 mL, 11.6 mmol). The mixture was stirred for 30 min, quenched with acetic acid, then diluted with water and sodium bicarbonate. The mixture was extracted with ethyl acetate and the combined organic extracts were concentrated in vacuo and purified by chromatography (silica, 10-50% ethyl acetate in hexanes) to give ethyl 3-oxo-3-(4-phenylthiazol-2-yl)propanoate (890 mmol, 3.23 mmol, 84%). MS (EI/CI) m/z: 276.1 [M+H].

Step 2

(Z)-Ethyl 3-(dimethylamino)-2-(4-phenylthiazole-2-carbonyl)acrylate

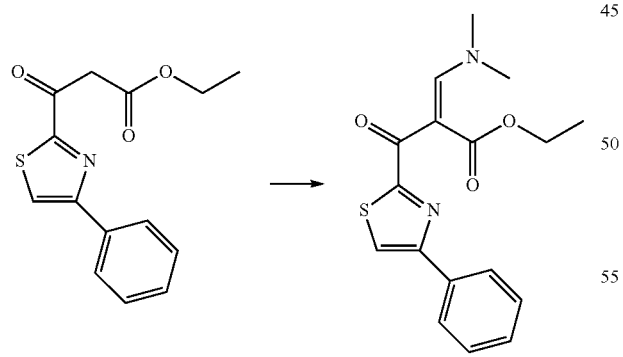

To a solution of ethyl 3-oxo-3-(4-phenylthiazol-2-yl)propanoate (890 mmol, 3.23 mmol) in ethanol (9 mL) was added dimethylformamide dimethyl acetal (385 mg, 3.23 mmol). The mixture was heated to 80° C. for 15 h and then concentrated in vacuo. Purification by chromatography (silica, 20-100% ethyl acetate in hexanes) gave (Z)-ethyl 3-(dimethylamino)-2-(4-phenylthiazole-2-carbonyl)acrylate (720 mg, 67%). $^1$H NMR (400 MHz, CHLOROFORM-d) δ ppm 7.95 (d, J=1.6 Hz, 2 H), 7.93 (s, 1 H), 7.45 (t, J=7.3 Hz, 2 H), 7.37 (t, J=7.4 Hz, 1 H), 4.13 (q, J=7.0 Hz, 2 H), 3.30 (br. s, 3 H), 3.01 (br. s, 3 H), 1.03 (t, J=7.1 Hz, 3 H).

Step 3

Ethyl 3-(4-phenylthiazol-2-yl)-1H-pyrazole-4-carboxylate

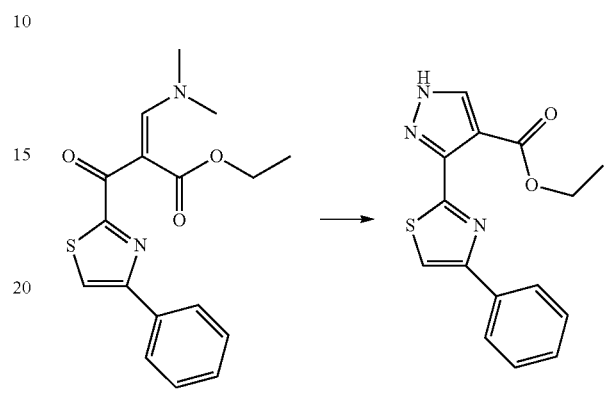

To a solution of (Z)-ethyl 3-(dimethylamino)-2-(4-phenylthiazole-2-carbonyl)acrylate (700 mg, 2.12 mmol) in ethanol (11 mL) was added hydrazine hydrate (117 mg, 2.33 mmol). Additional ethanol (5 mL) was added to the thick suspension after ~1 min and the mixture was stirred for a further 15 min. The mixture was diluted EtOH (5 mL), and then cooled to 0° C. The solid precipitate was collected by filtration and washed with cold EtOH, then diethyl ether, and finally dried to give a white solid. An additional amount of product was obtained by first concentrating the organic filtrate in vacuo, and then purifying the residue by chromatography (silica, 15-60% ethyl acetate in hexanes). This material was combined with the previously obtained solid to give ethyl 3-(4-phenylthiazol-2-yl)-1H-pyrazole-4-carboxylate (575 mg, 86%) as a white solid. $^1$H NMR (400 MHz, CHLOROFORM-d) δ ppm 8.11 (s, 1 H), 7.98 (d, J=7.9 Hz, 2 H), 7.73 (s, 1 H), 7.49 (t, J=7.6 Hz, 2 H), 7.41 (t, J=7.5 Hz, 1 H), 4.45 (q, J=7.3 Hz, 2 H), 1.46 (t, J=7.2 Hz, 3 H); MS (EI/CI) m/z: 299.8 [M+H].

Example 13

Ethyl 3-(4,5,6,7-tetrahydrobenzo[d]thiazol-2-yl)-1H-pyrazole-4-carboxylate

Step 1

Ethyl 4,5,6,7-tetrahydrobenzo[d]thiazole-2-carboxylate

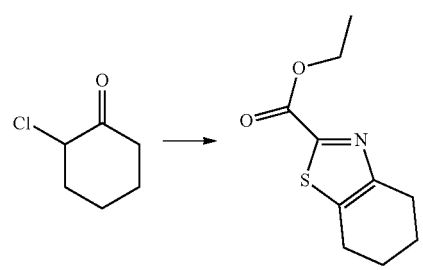

To a solution of 2-chlorocyclohexanone (2 g, 15.1 mmol) in ethanol (18 mL) was added ethyl 2-amino-2-thioxoacetate (2.11 g, 15.8 mmol). The mixture was sealed in two identical microwave vials and each one was irradiated at 150° C. for 1.5 h. Upon cooling the mixture was concentrated in vacuo and directly purified by chromatography (silica, 5-45% ethyl acetate in hexanes) to give ethyl 4,5,6,7-tetrahydrobenzo[d]thiazole-2-carboxylate (826 mg, 26%) as a yellow oil. MS (EI/CI) m/z: 212.3 [M+H].

Step 2

Ethyl 3-oxo-3-(4,5,6,7-tetrahydrobenzo[d]thiazol-2-yl)propanoate

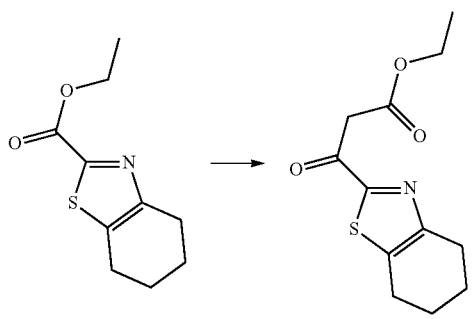 [SMILES: CCOC(=O)c1nc2c(s1)CCCC2 ; CCOC(=O)CC(=O)c1nc2c(s1)CCCC2]

To a solution of ethyl 4,5,6,7-tetrahydrobenzo[d]thiazole-2-carboxylate (240 mg, 1.14 mmol) in THF (2.3 mL) at −50° C. was added ethyl acetate (600 mg, 667 µL, 6.82 mmol) followed by lithium bis(trimethylsilyl)amide (1M in THF, 3.41 mL, 3.41 mmol). The mixture was stirred for 30 min and then quenched with acetic acid, diluted with water and saturated sodium bicarbonate solution and extracted with ethyl acetate. The combined extracts were concentrated in vacuo and the residue obtained was purified by chromatography (silica, 0-20% ethyl acetate in hexanes) to give ethyl 3-oxo-3-(4,5,6,7-tetrahydrobenzo[d]thiazol-2-yl)propanoate (110 mg, 434 µmol, 38%) as a yellow liquid. ¹H NMR (400 MHz, CHLOROFORM-d) δ ppm 4.24 (q, J=7.1 Hz, 2 H), 4.13 (s, 1 H), 2.89 (m, 4 H), 1.92 (m, 4 H), 1.29 (t, J=7.3 Hz, 3 H).

Step 3

(Z)-Ethyl 3-(dimethylamino)-2-(4,5,6,7-tetrahydrobenzo[d]thiazole-2-carbonyl)acrylate

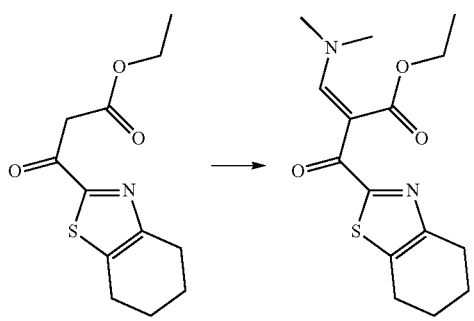 [SMILES: CCOC(=O)CC(=O)c1nc2c(s1)CCCC2 ; CCOC(=O)/C(=C\N(C)C)C(=O)c1nc2c(s1)CCCC2]

To a solution of ethyl 3-oxo-3-(4,5,6,7-tetrahydrobenzo[d]thiazol-2-yl)propanoate (680 mg, 2.68 mmol) in ethanol (7.7 mL) was added dimethylformamide dimethyl acetal (352 mg, 2.95 mmol). The mixture was heated to 80° C. for 3 h, cooled to r.t., concentrated in vacuo, and then purified by chromatography (silica, 20-100% ethyl acetate in hexanes) to give (Z)-ethyl 3-(dimethylamino)-2-(4,5,6,7-tetrahydrobenzo[d]thiazole-2-carbonyl)acrylate (464 mg, 56%). ¹H NMR (400 MHz, CHLOROFORM-d) δ ppm 7.82 (s, 1 H), 4.14 (m, 2 H), 3.19 (br. s, 3 H), 2.98 (br. s, 3 H), 2.85 (m, 4 H), 1.89 (m, 4 H), 1.12 (t, J=7.1 Hz, 3 H).

Step 4

Ethyl 3-(4,5,6,7-tetrahydrobenzo[d]thiazol-2-yl)-1H-pyrazole-4-carboxylate

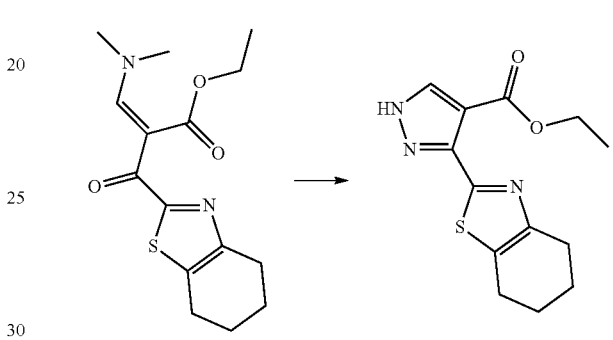

To a solution of (Z)-ethyl 3-(dimethylamino)-2-(4,5,6,7-tetrahydrobenzo[d]thiazole-2-carbonyl)acrylate (464 mg, 1.5 mmol) in ethanol (15 ml) was added a hydrazine monohydrate (82.9 mg, 1.66 mmol) in ethanol (1 mL) and the mixture stirred for 1 h. The thick suspension was diluted with cold diethyl ether (10 mL), filtered, and the solid obtained was washed with an additional portion of cold diethyl ether. The material was then dried in vacuo to give ethyl 3-(4,5,6,7-tetrahydrobenzo[d]thiazol-2-yl)-1H-pyrazole-4-carboxylate (370 mg, 88%). ¹H NMR (400 MHz, DMSO-d) δ ppm 8.15 (s, 1 H), 4.26 (q, J=7.0 Hz, 2 H), 2.80 (m, 4 H), 1.84 (m, 4 H), 1.23 (t, J=7.0 Hz, 3 H); MS (EI/CI) m/z: 277.8 [M+H].

Example 14

Ethyl 3-(5,6-dihydro-4H-cyclopenta[d]thiazol-2-yl)-1H-pyrazole-4-carboxylate

Step 1

Ethyl 5,6-dihydro-4H-cyclopenta[d]thiazole-2-carboxylate

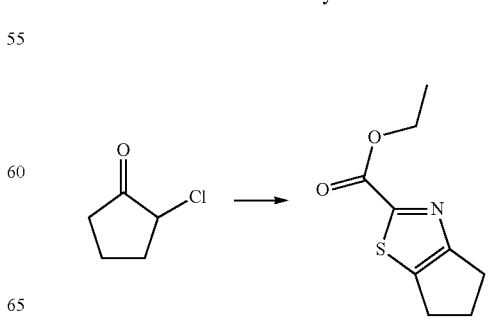

Ethyl 2-amino-2-thioxoacetate (1.4 g, 10.05 mmol) and 2-chlorocyclopentanone (1.18 g, 9.99 mmol) in ethanol (10 mL) were placed in a microwave vial and irradiated at 150° C. for 1.5 h. The mixture was cooled, concentrated in vacuo and then purified by chromatography (silica, 10-50% ethyl acetate in hexanes) to give ethyl 5,6-dihydro-4H-cyclopenta[d]thiazole-2-carboxylate (850 mg, 43%). $^1$H NMR (400 MHz, CHLOROFORM-d) δ ppm 4.48 (q, J=7.1 Hz, 2 H), 3.02 (t, J=7.3 Hz, 2 H), 2.95 (t, J=7.5 Hz, 2 H), 2.57 (m, 2 H), 1.46 (t, J=7.1 Hz, 3 H).

Step 2

Ethyl 3-(5,6-dihydro-4H-cyclopenta[d]thiazol-2-yl)-3-oxopropanoate

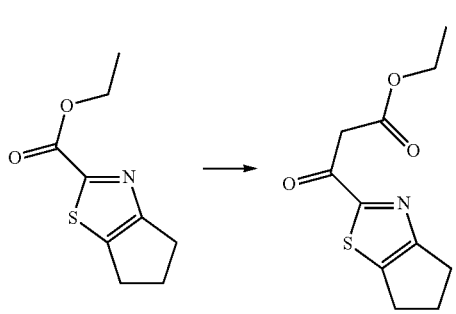 [SMILES: CCOC(=O)c1nc2c(s1)CCC2 ; CCOC(=O)CC(=O)c1nc2c(s1)CCC2]

To a solution of ethyl 5,6-dihydro-4H-cyclopenta[d]thiazole-2-carboxylate (850 mg, 4.31 mmol) and ethyl acetate (2.53 mL, 25.9 mmol) in THF (8.6 mL) at −50° C. was quickly added lithium bis(trimethylsilyl)amide (1M in toluene, 12.9 mL, 12.9 mmol). The mixture was stirred for 30 min before being quenched with acetic acid. After warming to room temperature it was diluted with water and saturated aqueous sodium bicarbonate solution, extracted with ethyl acetate, and concentrated in vacuo. The residue obtained was purified by chromatography (silica, 10-50% ethyl acetate in hexanes) to give ethyl 3-(5,6-dihydro-4H-cyclopenta[d]thiazol-2-yl)-3-oxopropanoate (900 mg, 87%) as an orange oil. MS (EI/CI) m/z: 239.7 [M+H].

Step 3

(Z)-Ethyl 2(5,6-dihydro-4H-cyclopenta[d]thiazole-2-carbonyl)-3-(dimethylamino)arcylate

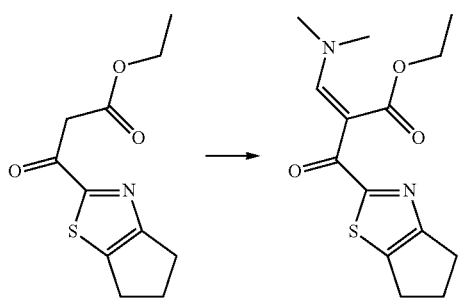 [SMILES: CCOC(=O)CC(=O)c1nc2c(s1)CCC2 ; CCOC(=O)/C(=C\N(C)C)C(=O)c1nc2c(s1)CCC2]

To a solution of ethyl 3-(5,6-dihydro-4H-cyclopenta[d]thiazol-2-yl)-3-oxopropanoate (750 mg, 3.13 mmol) in ethanol (9 mL) was added dimethylformamide dimethyl acetal (411 mg, 3.45 mmol). The mixture was heated to 80° C. for 3 h then cooled, concentrated in vacuo, and purified by chromatography (silica, 33-100% ethyl acetate in hexanes) to give (Z)-ethyl 2-(5,6-dihydro-4H-cyclopenta[d]thiazole-2-carbonyl)-3-(dimethylamino)acrylate (472 mg, 51%) as an oil. $^1$H NMR (400 MHz, CHLOROFORM-d) δ ppm 7.84 (s, 1 H), 4.15 (q, J=7.1 Hz, 2 H), 3.20 (br, s, 6 H), 2.99 (t, J=7.1 Hz, 2 H), 2.89 (t, J=7.4 Hz, 2 H), 2.53 (m, 2 H), 1.13 (t, J=7.4 Hz, 3 H).

Step 4

Ethyl 3-(5,6-dihydro-4H-cyclopenta[d]thiazol-2-yl)-1H-pyrazole-4-carboxylate

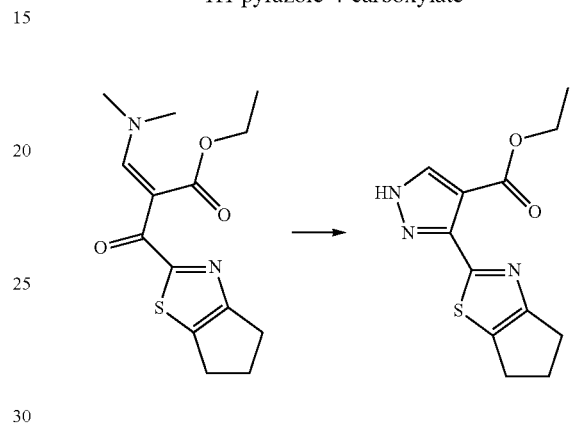

To a solution of (Z)-ethyl 2-(5,6-dihydro-4H-cyclopenta[d]thiazole-2-carbonyl)-3-(dimethylamino)acrylate (472 mg, 1.6 mmol) in ethanol (16 mL) was added hydrazine hydrate (88 mg, 1.76 mmol) in ethanol (1 mL). The thick suspension was stirred at r.t. for 1 h, diluted with diethyl ether, and collected by filtration, washed with ether, and then then dried to give ethyl 3-(5,6-dihydro-4H-cyclopenta[d]thiazol-2-yl)-1H-pyrazole-4-carboxylate (362 mg, 86%) as an off-white solid. $^1$H NMR (400 MHz, DMSO-d) δ ppm 8.15 (s, 1 H), 4.26 (q, J=7.4 Hz, 2 H), 2.97 (t, J=7.1 Hz, 2 H), 2.64 (t, J=7.7 Hz, 2 H), 2.52 (m, 2 H), 1.28 (t, J=7.1 Hz, 3 H); MS (EI/CI) m/z: 263.8 [M+H].

Example 15

N-tert-Butyl-3-(4-phenylthiazol-2-yl)-1H-pyrazole-4-carboxamide

Step 1

Ethyl 3-(4-phenylthiazol-2-yl)-1-((2-(trimethylsilyl)ethoxy)methyl)-1H-pyrazole-4-carboxylate

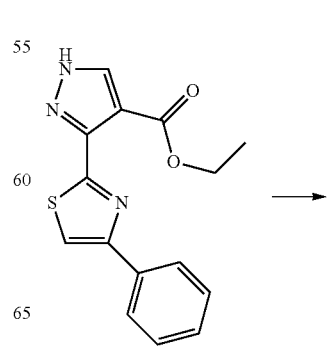

-continued

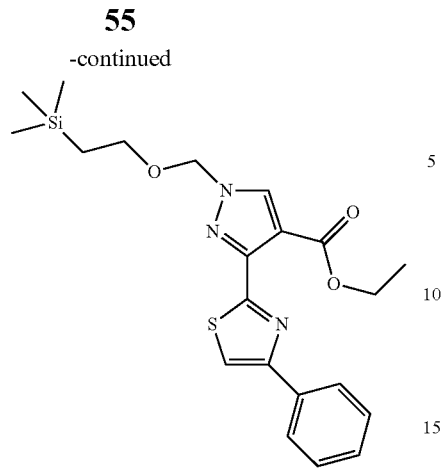

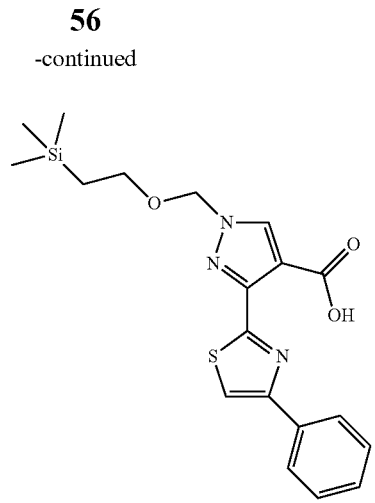

To a solution of ethyl 3-(4-phenylthiazol-2-yl)-1H-pyrazole-4-carboxylate (560 mg, 1.87 mmol) in THF (9.4 mL) cooled to 0° C., was added sodium hydride (150 mg, 3.74 mmol). The mixture was stirred for 15 min and then (2-(Chloromethoxy)ethyl)trimethylsilane (374 mg, 2.24 mmol) was added. After stirring at r.t. for 16 h the reaction mixture was quenched with saturated sodium bicarbonate solution and then extracted into ethyl acetate. The combined organic extracts were concentrated in vacuo and purified by chromatography (silica, 5-25% ethyl acetate in hexanes) to give ethyl 3-(4-phenylthiazol-2-yl)-1-((2-(trimethylsilyl)ethoxy)methyl)-1H-pyrazole-4-carboxylate (662 mg, 1.54 mmol, 82%) as a colorless oil. $^1$H NMR (400 MHz, CHLOROFORM-d) δ ppm 8.19 (s, 1 H), 7.99 (d, J=8.3 Hz, 2 H), 7.61 (s, 1 H), 7.42 (t, J=7.9 Hz, 2 H), 7.33 (t, J=7.4 Hz, 1 H), 5.52 (s, 2 H), 4.34 (q, J=7.18 Hz, 2 H), 3.67 (t, J=8.4 Hz, 2 H), 1.32 (t, J=7.3 Hz, 3 H), 0.96 (t, J=8.7 Hz, 2 H), 0.01 (s, 9 H).

To a solution of ethyl 3-(4-phenylthiazol-2-yl)-1-((2-(trimethylsilyl)ethoxy)methyl)-1H-pyrazole-4-carboxylate (790 mg, 1.84 mmol) in dioxane (26 mL) was added 1N sodium hydroxide (9.2 mL, 9.2 mmol). The mixture was stirred at r.t. for 16 h and then quenched with 10% HCl (~pH 6). The precipitate obtained by filtration, was washed with water and ether, and then dried to give 3-(4-phenylthiazol-2-yl)-1-((2-(trimethylsilyl)ethoxy)methyl)-1H-pyrazole-4-carboxylic acid (349 mg, 869 μmol, 47%) as a white solid. $^1$H NMR (400 MHz, CHLOROFORM-d) δ ppm 8.38 (s, 1 H), 7.84 (d, J=8.0 Hz, 2 H), 7.56 (s, 1 H), 7.48 (t, J=6.8 Hz, 2 H), 7.41 (t, J=7.3 Hz, 1 H), 5.49 (s, 2 H), 3.66 (t, J=8.4 Hz, 2 H), 0.96 (t, J=8.4 Hz, 2 H), 0.01 (s, 9 H).

Step 2

3-(4-Phenylthiazol-2-yl)-1-((2-(trimethylsilyl)ethoxy)methyl)-1H-pyrazole-4-carboxylic acid Step 3 N-tert-Butyl-3-(4-phenylthiazol-2-yl)-1-((2-(trimethylsilyl)ethoxy)methyl)-1H-pyrazole-4-carboxamide

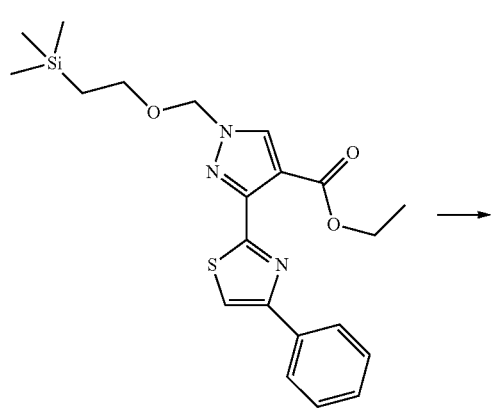

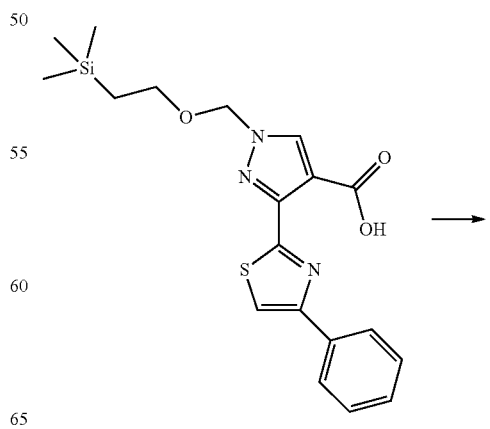

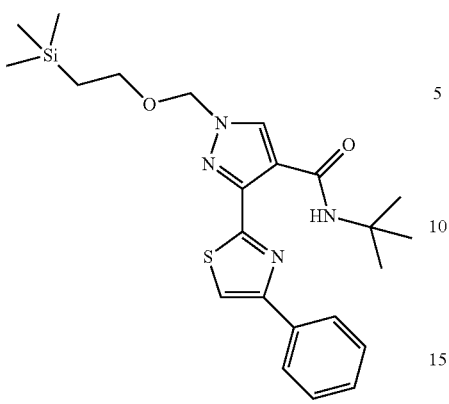

3-(4-Phenylthiazol-2-yl)-1-((2-(trimethylsilyl)ethoxy)methyl)-1H-pyrazole-4-carboxylic acid (115 mg, 286 μmol), 2-methylpropan-2-amine (83.8 mg, 1.15 mmol), 1-(3-dimethylaminopropyl)-3-ethylcarbodiimide hydrochloride (126 mg, 659 μmol) and HOBT (101 mg, 659 μmol) in DMF (1.2 mL) were stirred at r.t. for 16 h. After which the reaction mixture was quenched with 10% citric acid and then diluted with ethyl acetate and sodium bicarbonate. The phases were separated and the organic phase washed with additional sodium bicarbonate and brine, dried, filtered and concentrated in vacuo. Purification by chromatography (silica, 10-30% ethyl acetate in hexanes) gave N-tert-butyl-3-(4-phenylthiazol-2-yl)-1-((2-(trimethylsilyl)ethoxy)methyl)-1H-pyrazole-4-carboxamide (115 mg, 252 μmol, 88%) as a white solid. $^1$H NMR (400 MHz, CHLOROFORM-d) δ ppm 9.92 (s, 1 H), 8.31 (s, 1 H), 7.80 (d, J=7.7 Hz, 2 H), 7.42 (m, 3 H), 5.45 (s, 2 H), 3.53 (t, J=8.4 Hz, 2 H), 1.38 (s, 9 H), 0.95 (t, J=8.2 Hz, 2 H), 0.01 (s, 9 H).

Step 4

N-tert-Butyl-3-(4-phenylthiazol-2-yl)-1H-pyrazole-4-carboxamide

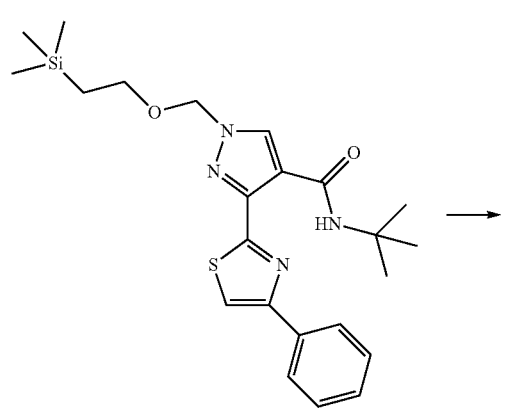

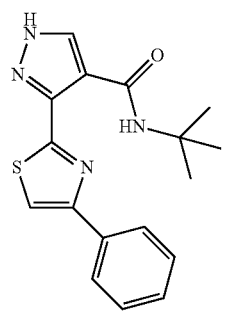

To a solution of N-tert-butyl-3-(4-phenylthiazol-2-yl)-1-((2-(trimethylsilyl)ethoxy)methyl)-1H-pyrazole-4-carboxamide (115 mg, 252 μmol) in dichloromethane (3.8 mL) was added trifluoroacetic acid (574 mg, 388 μL, 5.04 mmol). The mixture was stirred at r.t. for 16 h, then concentrated in vacuo. The residue obtained was redissolved in dichloromethane (3.8 mL), methanol (1.9 mL) and ammonium hydroxide (600 μL) and then stirred at r.t. for 1 h. This mixture was then concentrated in vacuo, triturated with water and filtered. The solid obtained was washed with water and ether. Further purification by chromatography (silica, 20-60% ethyl acetate in hexanes) gave N-tert-butyl-3-(4-phenylthiazol-2-yl)-1H-pyrazole-4-carboxamide (56 mg, 172 μmol, 68%) as an off-white solid. $^1$H NMR (400 MHz, DMSO-$d_6$) δ ppm 13.71 (s, 1 H), 9.55 (s, 1 H), 8.34 (s, 1 H), 8.10 (s, 1 H), 7.91 (d, J=7.6 Hz, 2 H), 7.50 (t, J=7.6 Hz, 2 H), 7.42 (t, J=7.4 Hz, 1 H), 1.33 (s, 9 H); MS (EI/CI) m/z: 326.9 [M+H].

Example 16

N-Isopropyl-3-(4-phenylthiazol-2-yl)-1H-pyrazole-4-carboxamide

Step 1

N-Isopropyl-3-(4-phenylthiazol-2-yl)-1-((2-(trimethylsilyl)ethoxy)methyl)-1H-pyrazole-4-carboxamide

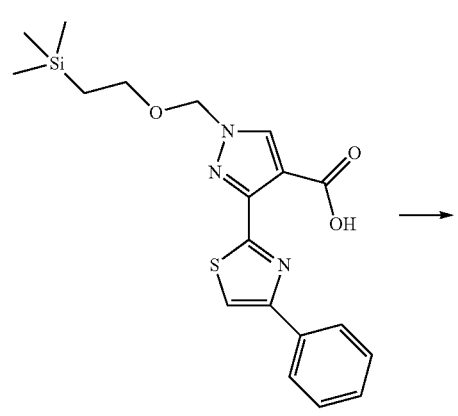

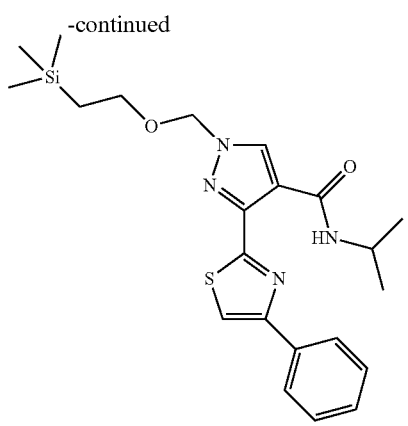

To a solution of 3-(4-phenylthiazol-2-yl)-1-((2-(trimethylsilyl)ethoxy)methyl)-1H-pyrazole-4-carboxylic acid (89 mg, 222 µmol) in DMF (1 mL) was added HATU (101 mg, 266 µmol), DIPEA (85.9 mg, 116 µL, 665 µmol) and propan-2-amine (39.3 mg, 665 µmol). The mixture was stirred at r.t. for 16 h, then quenched with 10% citric acid and diluted with sodium bicarbonate and ethyl acetate. The organic layer was collected, concentrated in vacuo, and then purified by chromatography (silica, 15-45% ethyl acetate in hexanes) to give N-isopropyl-3-(4-phenylthiazol-2-yl)-1-((2-(trimethylsilyl)ethoxy)methyl)-1H-pyrazole-4-carboxamide (92 mg, 208 µmol, 94%) as a white solid. MS (EI/CI) m/z: 443.2 [M+H].

Step 2

N-Isopropyl-3-(4-phenylthiazol-2-yl)-1H-pyrazole-4-carboxamide

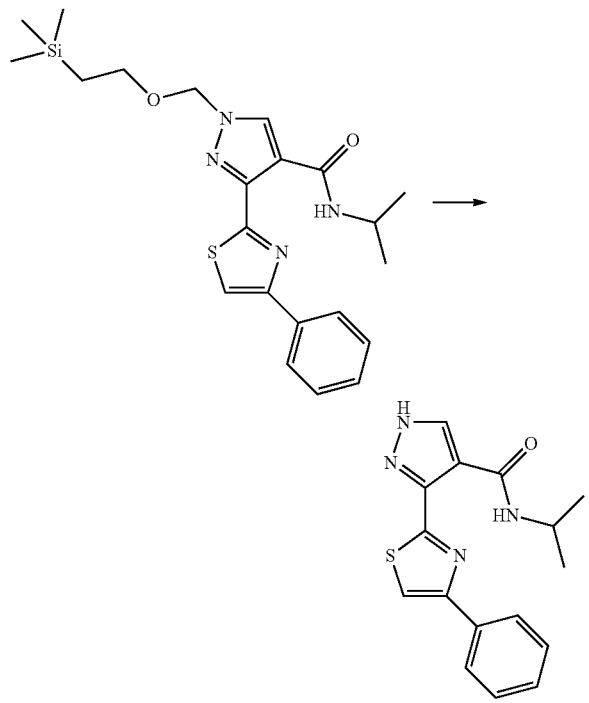

To a solution of N-isopropyl-3-(4-phenylthiazol-2-yl)-1-((2-(trimethylsilyl)ethoxy)methyl)-1H-pyrazole-4-carboxamide (92 mg, 208 µmol) in dichloromethane was added trifluoroacetic acid (474 mg, 320 µl, 4.16 mmol). The mixture was stirred at r.t. for 16 h and then concentrated in vacuo. The residue obtained was redissolved in dichloromethane (3.2 mL), methanol (1.8 mL) and ammonium hydroxide (500 µL) and stirred at r.t. for 1 h. The mixture was concentrated in vacuo and directly purified by chromatography (silica, 50-90% ethyl acetate in hexanes) to give N-isopropyl-3-(4-phenylthiazol-2-yl)-1H-pyrazole-4-carboxamide (40 mg, 128 µmol, 62%) as a white solid. $^1$H NMR (400 MHz, DMSO-$d_6$) δ ppm 13.86 (s, 1 H), 10.27 (d, J=8.3 Hz, 1 H), 8.50 (s, 1 H), 8.27 (s, 1 H), 8.05 (d, J=7.5 Hz, 2 H), 7.63 (t, J=7.5 Hz, 2 H), 7.54 (t, J=7.5 Hz, 1 H), 4.28 (m, 1 H), 1.28 (d, J=6.7 Hz, 6 H); MS (EI/CI) m/z: 312.8 [M+H].

Example 17

N-tert-Butyl-3-(5,6-dihydro-4H-cyclopenta[d]thiazol-2-yl)-1H-pyrazole-4-carboxamide Step 1

Ethyl 3-5,6-dihydro-4H-cyclopenta[d]thiazol-2-yl)-1-((2-trimethylsilyl)ethoxy)methyl)-1H-pyrazole-4-carboxylate

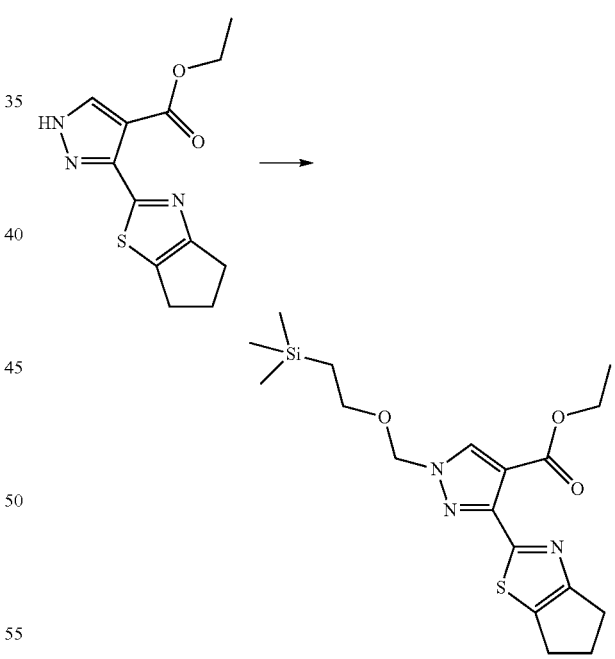

To a solution of ethyl 3-(5,6-dihydro-4H-cyclopenta[d]thiazol-2-yl)-1H-pyrazole-4-carboxylate (342 mg, 1.3 mmol) in THF (6.5 mL) cooled to 0° C. was added sodium hydride (104 mg, 2.6 mmol). After stirring for 15 min (2-(chloromethoxy)ethyl)trimethylsilane (260 mg, 1.56 mmol) was added, and the mixture was warmed to r.t. After 16 h, the mixture was quenched with sodium bicarbonate and diluted with ethyl acetate. The organic phase was separated and washed with sodium bicarbonate and brine, concentrated in vacuo, and purified by chromatography

61

(silica, 10-30% ethyl acetate in hexanes) to give ethyl 3-(5,6-dihydro-4H-cyclopenta[d]thiazol-2-yl)-1-((2-(trimethylsilyl)ethoxy)methyl)-1H-pyrazole-4-carboxylate (380 mg, 966 µmol, 74%) as an orange oil. MS (EI/CI) m/z: 394.0 [M+H].

Step 2

3-(5,6-Dihydro-4H-cyclopenta[d]trimethylsilyl)ethoxy)methyl)-1H-pyrazole-4-carboxylic acid

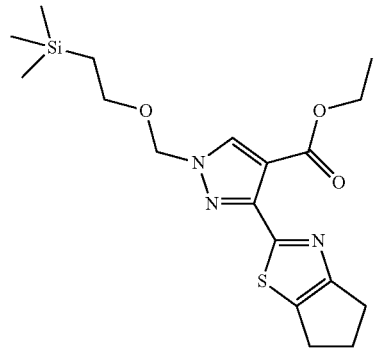

To a solution of ethyl 3-(5,6-dihydro-4H-cyclopenta[d]thiazol-2-yl)-1-((2-(trimethylsilyl)ethoxy)methyl)-1H-pyrazole-4-carboxylate (437 mg, 1.11 mmol) in dioxane (15.9 mL) was added 1M sodium hydroxide (5.55 mL, 5.55 mmol). The mixture was stirred at r.t. for 16 h, then acidified with 10% HCl (to ~pH 6). The mixture was diluted with water and ethyl acetate, and the phases separated. The organic phase was washed with water and brine, then concentrated in vacuo. Purification by chromatography (silica, 20-60% ethyl acetate in hexanes) gave 3-(5,6-dihydro-4H-cyclopenta[d]thiazol-2-yl)-1-((2-(trimethylsilyl)ethoxy)methyl)-1H-pyrazole-4-carboxylic acid (306 mg, 837 µmol, 75%) as a white solid. MS (EI/CI) m/z: 365.9 [M+H].

Step 3

N-tert-Butyl-3-(5,6-dihydro-4H-cyclopenta[d]thiazol-2-yl)-1-((2-(trimethylsilyl)ethoxy)methyl)-1H-pyrazole-4-carboxamide

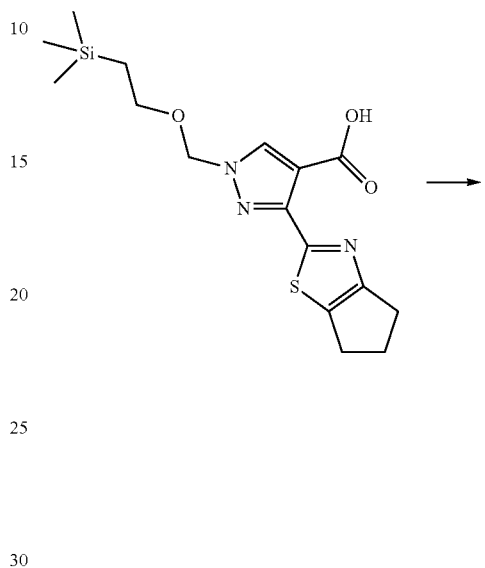

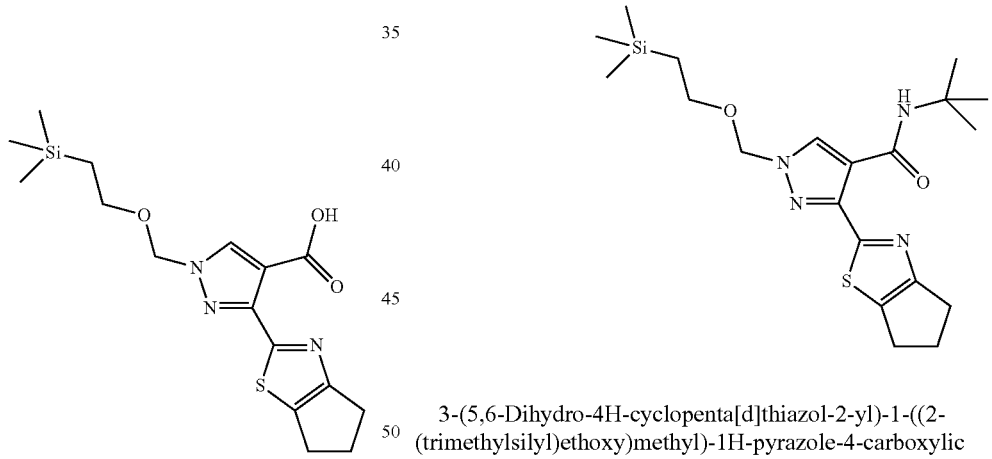

3-(5,6-Dihydro-4H-cyclopenta[d]thiazol-2-yl)-1-((2-(trimethylsilyl)ethoxy)methyl)-1H-pyrazole-4-carboxylic acid (100 mg, 274 µmol), 2-methylpropan-2-amine (80.0 mg, 1.09 mmol), 1-(3-dimethylaminopropyl)-3-ethylcarbodiimide hydrochloride (121 mg, 629 µmol) and HOBT (96.4 mg, 629 µmol) in DMF (1.5 mL) were stirred at r.t. for 16 h. The reaction mixture was quenched with 10% citric acid and then diluted with sodium bicarbonate and ethyl acetate. The organic phase was separated and then washed with sodium bicarbonate and water, concentrated in vacuo, and purified by chromatography (silica, 10-30% ethyl acetate in hexanes) to give N-tert-butyl-3-(5,6-dihydro-4H-cyclopenta[d]thiazol-2-yl)-1-((2-(trimethylsilyl)ethoxy)methyl)-1H-pyrazole-4-carboxamide (105 mg, 250 µmol, 91%) as a white solid. $^1$H NMR (400 MHz, CHLOROFORM-d) δ ppm 10.94 (s, 1 H), 8.32 (s, 1 H), 5.43 (s, 1 H), 3.61 (t, J=8.4 Hz, 2 H), 2.98 (t, J=7.2 Hz, 2 H), 2.89 (t, J=7.2 Hz, 2 H), 2.58 (m, 2 H), 1.51 (s, 9 H), 0.95 (t, J=8.4 Hz, 2 H), 0.01 (s, 9 H).

Step 4

N-tert-Butyl-3-(5,6-dihydro-4H-cyclopenta[d]thi-
azol-2-yl)-1H-pyrazole-4-carboxamide Example 18

N-tert-Butyl-3-(4,5,6,7-tetrahydrobenzo[d]thiazol-2-
yl)-1H-pyrazole-4-carboxamide Step 1

Ethyl 3-4,5,6,7-tetrahydrobenzo[d]thiazol-2-yl)-1-
((2-trimethylsilyl)ethoxy)methyl)-1H-pyrazole-4-
carboxylate

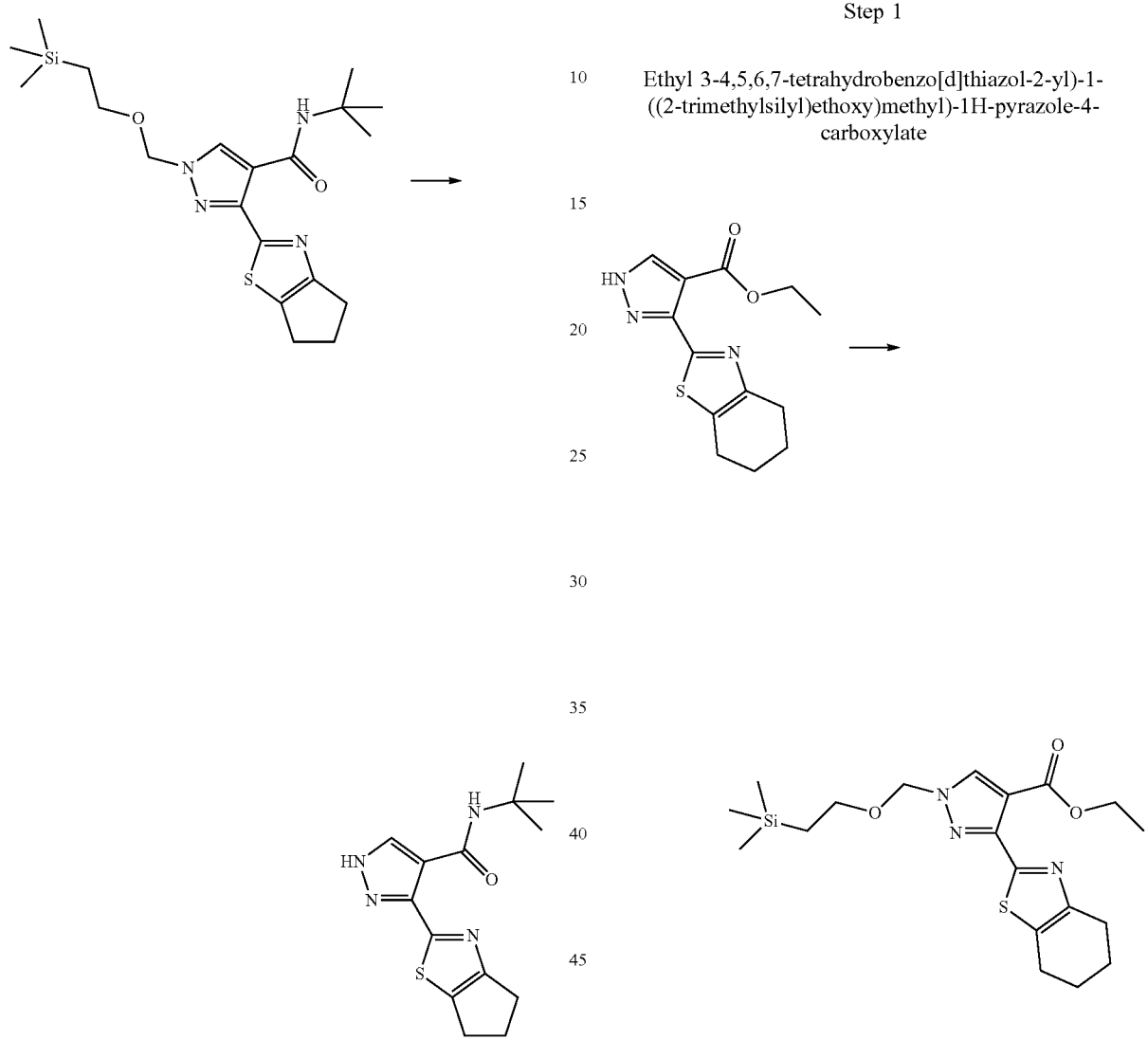

To a solution of N-tert-butyl-3-(5,6-dihydro-4H-cyclo-penta[d]thiazol-2-yl)-1-((2-(trimethylsilyl)ethoxy)methyl)-1H-pyrazole-4-carboxamide (105 mg, 250 μmol) in dichloromethane (3.9 mL) was added trifluoroacetic acid (569 mg, 385 μL, 4.99 mmol). The mixture was stirred at r.t for 16 h, then concentrated in vacuo. The residue was redissolved in dichloromethane (3.5 mL), methanol (1.7 mL) and ammonium hydroxide (600 μL) and stirred at r.t. for 1 h. The mixture was then concentrated in vacuo, the residue obtained was triturated with water and collected by filtration. The solid was washed with water and ether and then dried under vacuum to give N-tert-butyl-3-(5,6-dihydro-4H-cyclopenta[d]thiazol-2-yl)-1H-pyrazole-4-carboxamide (62 mg, 214 μmol, 86%) as a white solid. $^1$H NMR (400 MHz, DMSO-$d_6$) δ ppm 13.53 (s, 1 H), 10.70 (s, 1 H), 8.25 (s, 1 H), 2.94 (t, J=7.0 Hz, 2 H), 2.83 (t, J=7.2 Hz, 2 H), 2.50 (m, 2 H), 1.41 (s, 9 H); MS (EI/CI) m/z: 290.9 [M+H].

To a solution of ethyl 3-(4,5,6,7-tetrahydrobenzo[d]thi-azol-2-yl)-1H-pyrazole-4-carboxylate (359 mg, 1.29 mmol) in (2-(chloromethoxy)ethyl)trimethylsilane (259 mg, 1.55 mmol) cooled to 0° C. was added sodium hydride (104 mg, 2.59 mmol). The mixture was stirred for 15 min and (2-(Chloromethoxy)ethyl)trimethylsilane (259 mg, 1.55 mmol) was then added. After stirring at r.t. for 16 h, the reaction mixture was quenched with aqueous sodium bicarbonate and diluted with ethyl acetate. The organic phase was separated, washed with sodium bicarbonate and brine, concentrated in vacuo and purified by chromatography (silica, 10-30% ethyl acetate and hexanes) to give ethyl 3-(4,5,6,7-tetrahydrobenzo[d]thiazol-2-yl)-1-((2-(trimethylsilyl)ethoxy)methyl)-1H-pyrazole-4-carboxylate (300 mg, 736 μmol, 57%) as a colorless oil. $^1$H NMR (400 MHz, CHLOROFORM-d) δ ppm 8.07 (s, 1 H), 5.84 (s, 1 H), 4.35 (q, J=7.1 Hz, 2 H), 3.58 (t, J=8.4 Hz, 2 H), 2.94 (m, 4 H), 1.98 (m, 4 H), 1.38 (t, J=7.1 Hz, 3 H), 0.90 (t, J=8.4 Hz, 2 H), 0.01 (s, 9 H).

Step 2

3-4,5,6,7-Tetrahydrobenzo[d]thiazol-2-yl)-1-((2-trimethylsilyl)ethoxy)methyl)-1H-pyrazole-4-carboxylic acid

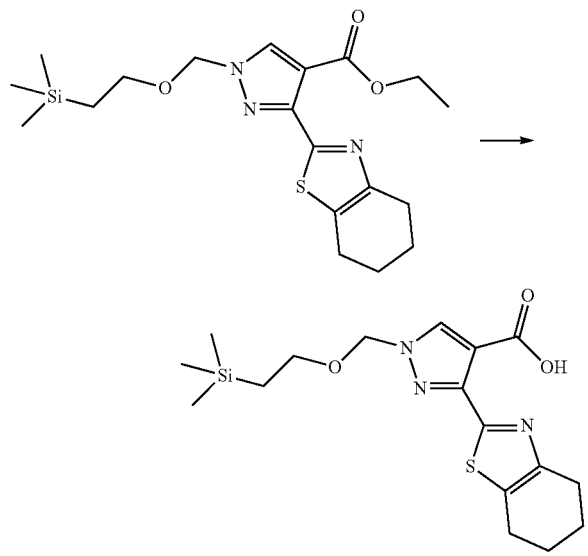

To a solution of ethyl 3-(4,5,6,7-tetrahydrobenzo[d]thiazol-2-yl)-1-((2-(trimethylsilyl)ethoxy)methyl)-1H-pyrazole-4-carboxylate (350 mg, 859 µmol) in dioxane (12.3 mL) was added 1N sodium hydroxide (4.29 mL, 4.29 mmol). The mixture was stirred at r.t. for 16 h then acidified with 10% HCl (to ~pH 6) and then diluted with water and ethyl acetate. The organic phase was separated washed with water and brine, and then concentrated in vacuo. Purification by chromatography (silica 20-60% ethyl acetate in hexanes) gave 3-(4,5,6,7-tetrahydrobenzo[d]thiazol-2-yl)-1-((2-(trimethylsilyl)ethoxy)methyl)-1H-pyrazole-4-carboxylic acid (273 mg, 719 µmol, 84%) as a white solid. MS (EI/CI) m/z: 379.9 [M+H].

Step 3

N-tert-Butyl-3-(4,5,6,7-tetrahydrobenzo[d]thiazol-2-yl)-1-((2-trimethylsilyl)ethoxy)methyl)-1H-pyrazole-4-carboxamide

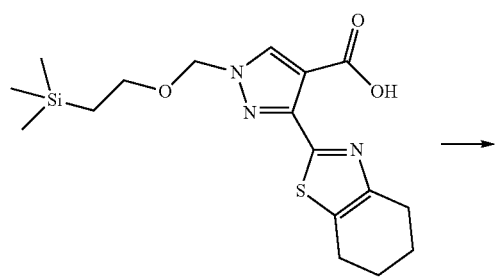

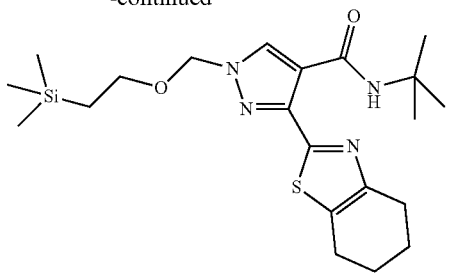

3-(4,5,6,7-Tetrahydrobenzo[d]thiazol-2-yl)-1((2-(trimethylsilyl)ethoxy)methyl)-1H-pyrazole-4-carboxylic acid (100 mg, 263 µmol), 2-methylpropan-2-amine (77.1 mg, 1.05 mmol), 1-(3-dimethylaminopropyl)-3-ethylcarbodiimide hydrochloride (116 mg, 606 µmol) and HOBT (92.8 mg, 606 µmol) in DMF (1.5 mL) were stirred at r.t. for 16 h. The reaction mixture was quenched with 10% citric acid and then diluted with sodium bicarbonate and ethyl acetate. The organic phase was separated, washed with sodium bicarbonate and water, then concentrated in vacuo. Purification by chromatography (silica, 10-30% ethyl acetate in hexanes) gave N-tert-butyl-3-(4,5,6,7-tetrahydrobenzo[d]thiazol-2-yl)-1((2-(trimethylsilyl)ethoxy)methyl)-1H-pyrazole-4-carboxamide (102 mg, 235 µmol, 89%) as a white solid. $^1$H NMR (400 MHz, CHLOROFORM-d) δ ppm 10.89 (s, 1 H), 8.28 (s, 1 H), 5.42 (s, 2 H), 3.61 (t, J=8.6 Hz, 2 H), 2.83 (m, 4 H), 1.92 (m, 2 H). 1.52 (s, 9 H), 0.95 (t, J=8.4 Hz, 2 H), 0.01 (s, 9 H).

Step 4

N-tert-Butyl-3-(4,5,6,7-tetrahydrobenzo[d]thiazol-2-yl)-1H-pyrazole-4-carboxamide

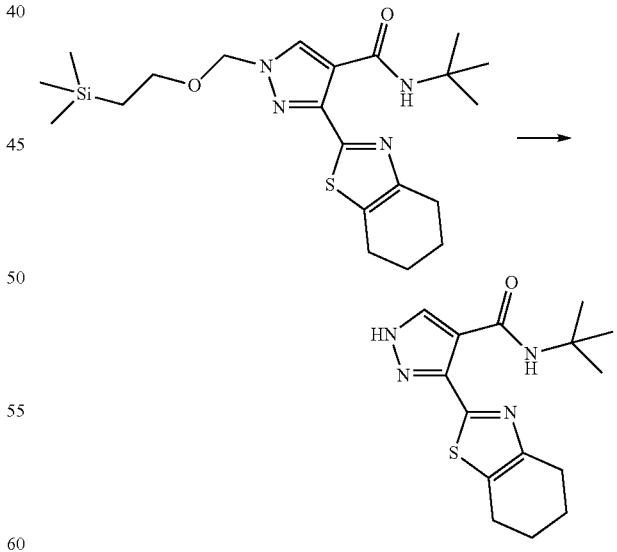

To a solution of N-tert-butyl-3-(4,5,6,7-tetrahydrobenzo[d]thiazol-2-yl)-1-((2-(trimethylsilyl)ethoxy)methyl)-1H-pyrazole-4-carboxamide (102 mg, 235 µmol) in dichloromethane (3.6 mL) was added trifluoroacetic acid (535 mg, 362 µL, 4.69 mmol). The mixture was stirred at r.t. for 16 h then concentrated in vacuo. The residue obtained was redissolved in dichloromethane (3.5 mL), methanol (1.7 mL) and ammonium hydroxide (550 µL). This mixture was stirred at r.t. for 1 h then concentrated in vacuo, and the residue obtained triturated with water. The solid was collected by filtration and washed with water and ether, then dried under vacuum to give N-butyl-3-(4,5,6,7-tetrahydrobenzo[d]thiazol-2-yl)-1H-pyrazole-4-carboxamide (43 mg, 141 µmol, 60%) as a white solid. $^1$H NMR (400 MHz, DMSO-$d_6$) δ ppm 13.54 (s, 1 H), 10.68 (s, 1 H), 8.26 (s, 1 H), 2.80 (m, 4 H), 1.84 (m, 4 H), 1.43 (s, 9 H); MS (EI/CI) m/z: 304.9 [M+H].

Example 19

N-Cyclopentyl-3-(4-phenylthiazol-2-yl)-1-((2-(trimethylsilyl)ethoxy)methyl)-1H-pyrazole-4-carboxamide Step 1

N-Cyclopentyl-3-(4-phenylthiazol-2-yl)-1-((2-(trimethylsilyl)ethoxy)methyl)-1H-pyrazole-4-carboxamide

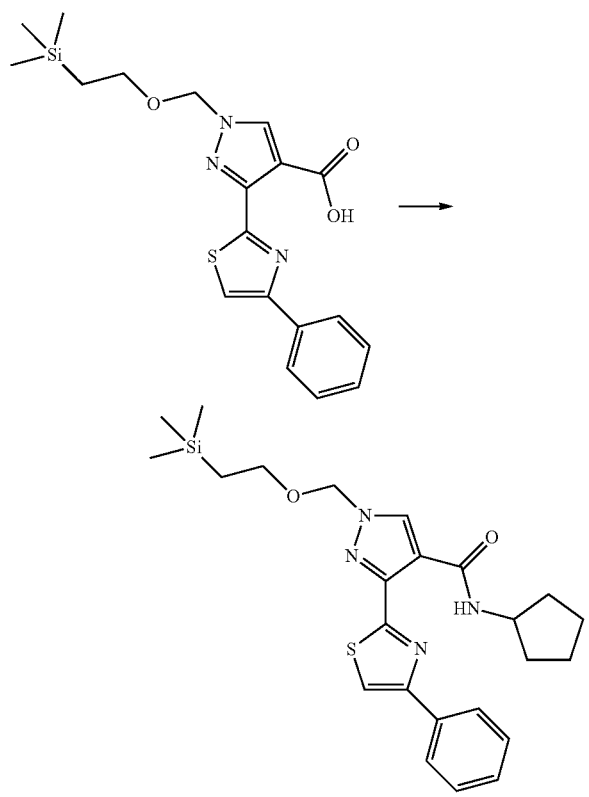

To a solution of 3-(4-phenylthiazol-2-yl)-1-((2-(trimethylsilyl)ethoxy)methyl)-1H-pyrazole-4-carboxylic acid (58 mg, 144 µmol) in DMF (1 mL) was added cyclopentanamine (36.9 mg, 433 µmol), HATU (65.9 mg, 173 µmol) and DIPEA (56.0 mg, 75.7 µL, 433 µmol). The mixture was stirred at r.t. for 16 h, then quenched with 10% citric acid and then diluted with ethyl acetate. The organic phase was separated, washed with sodium bicarbonate and brine, then concentrated in vacuo. Purification by chromatography (silica, 15-35% ethyl acetate in hexanes) to give N-cyclopentyl-3-(4-phenylthiazol-2-yl)-1-((2-(trimethylsilyl)ethoxy)methyl)-1H-pyrazole-4-carboxamide (58 mg, 124 µmol, 86%) as a white solid. MS (EI/CI) m/z: 469.1 [M+H].

Step 2

N-Cyclopentyl-3-(4-phenylthiazol-2-yl)-1-((2-(trimethylsilyl)ethoxy)methyl)-1H-pyrazole-4-carboxamide

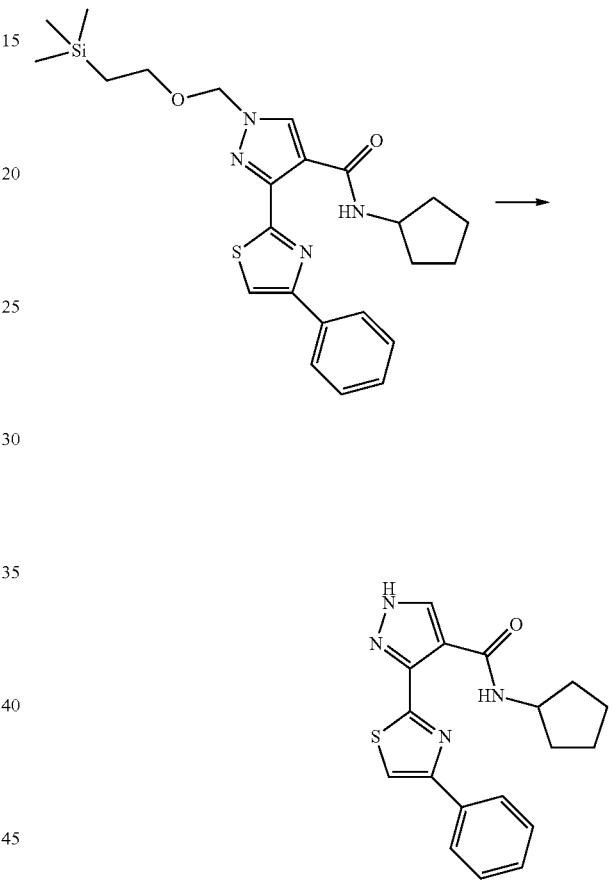

To a solution of N-cyclopentyl-3-(4-phenylthiazol-2-yl)-1-((2-(trimethylsilyl)ethoxy)methyl)-1H-pyrazole-4-carboxamide (58 mg, 124 µmol) in dichloromethane (1.9 mL) was added trifluoroacetic acid (282 mg, 191 µL, 2.47 mmol). The mixture was stirred at r.t for 16 h then concentrated in vacuo. The residue obtained was redissolved in dichloromethane (2 mL), methanol (1 mL) and ammonium hydroxide (300 µL) and stirred at r.t. for 1 h. The mixture was then concentrated in vacuo, and the residue obtained was triturated with water and collected by filtration. The solid was washed with water and ether then dried to give N-cyclopentyl-3-(4-phenylthiazol-2-yl)-1-((2-(trimethylsilyl)ethoxy)methyl)-1H-pyrazole-4-carboxamide (58 mg, 124 µmol, 100%) as a white solid. $^1$H NMR (400 MHz, DMSO-$d_6$) δ ppm 13.77 (s, 1 H), 10.22 (d, J=7.5 Hz, 1 H), 8.41 (s, 1 H), 8.18 (s, 1 H), 7.93 (d, J=7.5 Hz, 2 H), 7.54 (t, J=7.7 Hz, 2 H), 7.46 (t, J=7.3 Hz, 1 H), 4.31 (m, 1 H), 1.95 (m, 2 H), 1.61 (m, 2 H), 1.49 (m, 4 H); MS (EI/CI) m/z: 339.9 [M+H].

Example 20

3-(4-Phenylthiazol-2-yl)-N-(tetrahydro-2H-pyran-4-yl)-1H-pyrazole-4-carboxamide

Step 1

3-(4-Phenylthiazol-2-yl)-N-(tetrahydro-2H-pyran-4-yl)-1-((2-(trimethylsilyl)ethoxy)methyl)-1H-pyrazole-4-carboxamide

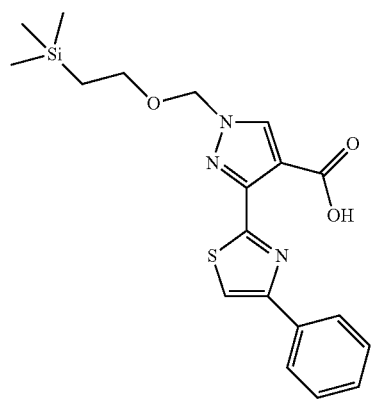

To a solution of 3-(4-phenylthiazol-2-yl)-1-((2-(trimethylsilyl)ethoxy)methyl)-1H-pyrazole-4-carboxylic acid (58 mg, 144 μmol) in DMF (1 mL) was added tetrahydro-2H-pyran-4-amine (43.8 mg, 433 μmol), HATU (65.9 mg, 173 μmol) and DIPEA (56.0 mg, 75.7 μL, 433 μmol). The mixture was stirred at r.t. for 16 h, then quenched with 10% citric acid and diluted with ethyl acetate. The organic phase was separated, washed with sodium bicarbonate and brine, then concentrated in vacuo. Purification by chromatography (silica, 15-100% ethyl acetate in hexanes) gave 3-(4-phenylthiazol-2-yl)-N-(tetrahydro-2H-pyran-4-yl)-1-((2-(trimethylsilyl)ethoxy)methyl)-1H-pyrazole-4-carboxamide (67 mg, 138 μmol, 96%) as a white solid. MS (EI/CI) m/z: 485.1 [M+H].

Step 2

3-(4-Phenylthiazol-2-yl)-N-(tetrahydro-2H-pyran-4-yl)-1H-pyrazole-4-carboxamide

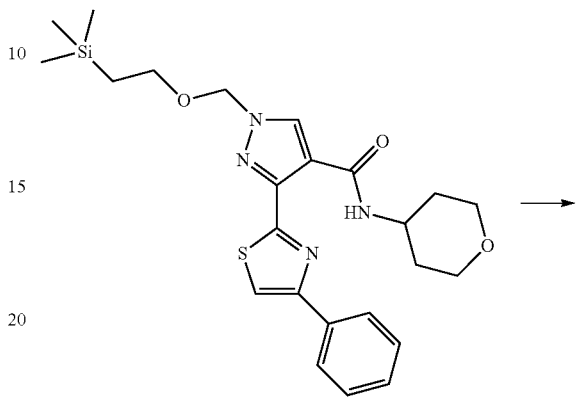

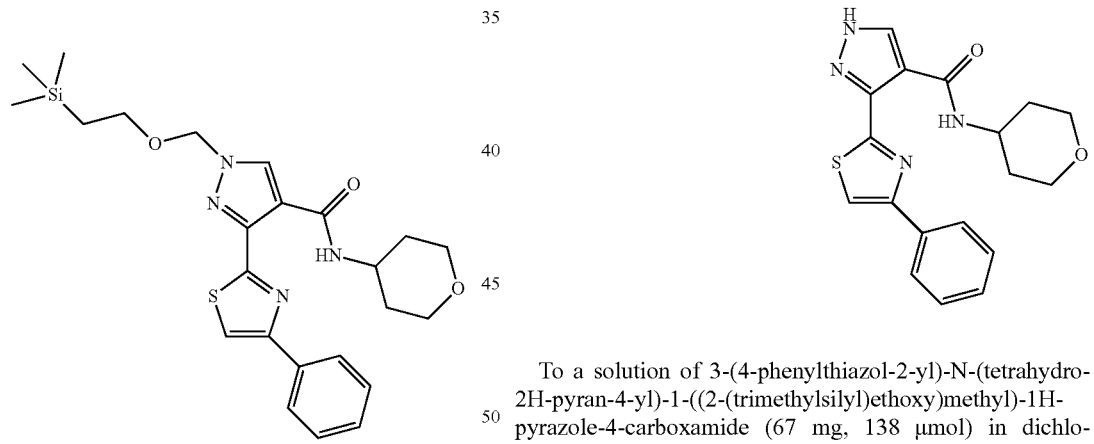

To a solution of 3-(4-phenylthiazol-2-yl)-N-(tetrahydro-2H-pyran-4-yl)-1-((2-(trimethylsilyl)ethoxy)methyl)-1H-pyrazole-4-carboxamide (67 mg, 138 μmol) in dichloromethane (2.1 mL) was added trifluoroacetic acid (315 mg, 213 μL, 2.76 mmol). The mixture was stirred at r.t. for 16 h, then concentrated in vacuo. The residue obtained was redissolved in dichloromethane (2 mL), methanol (1 mL) and ammonium hydroxide (300 μL) and stirred at r.t for 1 h. The mixture was then concentrated in vacuo, and the solid obtained triturated with water, filtered, washed with water and ether, then dried to give 3-(4-phenylthiazol-2-yl)-N-(tetrahydro-2H-pyran-4-yl)-1H-pyrazole-4-carboxamide (33.7 mg, 95.1 μmol, 69%) as a white solid. $^1$H NMR (400 MHz, DMSO-$d_6$) δ ppm 13.78 (s, 1 H), 10.24 (d, J=7.7 Hz, 1 H), 8.42 (s, 1 H), 8.18 (s, 1 H), 7.95 (d, J=7.7 Hz, 2 H), 7.52 (t, J=7.8 Hz, 2 H), 7.45 (t, J=7.3 Hz, 1 H), 4.10 (m, 1 H), 3.83 (d, J=12.1 Hz), 3.37 (q, J=11.8 Hz), 1.83 (d, J=12.2 Hz, 2 H), 1.52 (q, J=11.6 Hz, 2 H); MS (EI/CI) m/z: 355.0 [M+H].

Example 21

3-(5,6-Dihydro-4H-cyclopenta[d]thiazol-2-yl)-N-(tetrahydro-2H-pyran-4-yl)-1H-pyrazole-4-carboxamide

Step 1

3-(5,6-Dihydro-4H-cyclopenta[d]thiazol-2-yl)-N-(tetrahydro-2H-pyran-4-yl)-1-((2-(trimethylsilyl)ethoxy)methyl)-1H-pyrazole-4-carboxamide

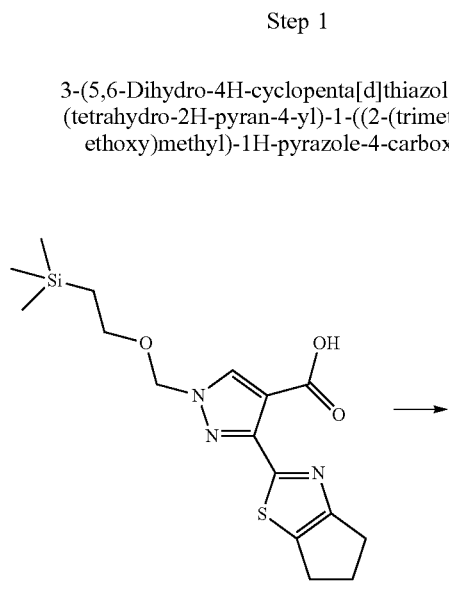

To a solution of 3-(5,6-dihydro-4H-cyclopenta[d]thiazol-2-yl)-1-((2-(trimethylsilyl)ethoxy)methyl)-1H-pyrazole-4-carboxylic acid (100 mg, 274 μmol) in DMF (2 mL) was added tetrahydro-2H-pyran-4-amine (83.0 mg, 821 μmol, HATU (156 mg, 410 μmol) and DIPEA (106 mg, 143 μL, 821 μmol). The mixture was stirred at r.t. for 16 h, quenched with 10% citric acid, and then diluted with ethyl acetate and sodium bicarbonate. The organic phase was separated, washed with sodium bicarbonate and brine, concentrated in vacuo and then purified by chromatography (silica, 40-80% ethyl acetate in hexanes) to give 3-(5,6-dihydro-4H-cyclopenta[d]thiazol-2-yl)-N-(tetrahydro-2H-pyran-4-yl)-1-((2-(trimethylsilyl)ethoxy)methyl)-1H-pyrazole-4-carboxamide (121 mg, 270 μmol, 99%) as an off-white solid. MS (EI/CI) m/z: 449.1 [M+H].

Step 2

3-(5,6-Dihydro-4H-cyclopenta[d]thiazol-2-yl)-N-(tetrahydro-2H-pyran-4-yl)-1H-pyrazole-4-carboxamide

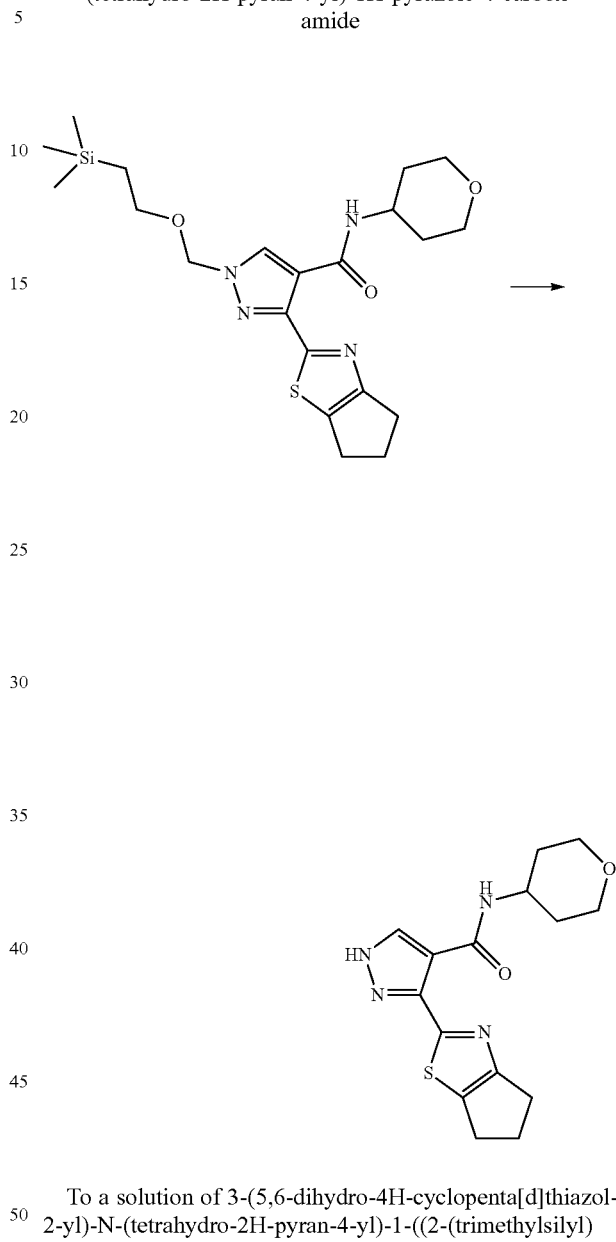

To a solution of 3-(5,6-dihydro-4H-cyclopenta[d]thiazol-2-yl)-N-(tetrahydro-2H-pyran-4-yl)-1-((2-(trimethylsilyl)ethoxy)methyl)-1H-pyrazole-4-carboxamide (121 mg, 270 μmol) in dichloromethane (4.2 mL) was added trifluoroacetic acid (615 mg, 416 μL, 5.39 mmol). The mixture was stirred at r.t. for 16 h then concentrated in vacuo. The residue obtained was redissolved in dichloromethane (4 mL), methanol (2 mL) and ammonium hydroxide (600 μL) and stirred at r.t for 1 h. The mixture was then concentrated in vacuo, triturated with water, filtered and washed with water and ether to give 3-(5,6-dihydro-4H-cyclopenta[d]thiazol-2-yl)-N-(tetrahydro-2H-pyran-4-yl)-1H-pyrazole-4-carboxamide (68 mg, 203 μmol, 75%) as a white solid. $^1$H NMR (400 MHz, DMSO-d) δ ppm 13.57 (s, 1 H), 10.90 (s, 1H), 8.37 (s, 1 H), 4.07 (m, 1 H), 3.89 (m, 2 H), 3.54 (t, J=10.2 Hz, 2 H), 2.99 (t, J=7.4 Hz, 2 H), 2.89 (t, J=6.7 Hz, 2 H), 1.95 (d, J=13.2 Hz, 2 H), 1.54 (m, 2 H); MS (EI/CI) m/z: 319.0 [M+H].

Example 22

N-(Tetrahydro-2H-pyran-4-yl)-3-(4,5,6,7-tetrahydrobenzo[d]thiazol-2-yl)-1H-pyrazole-4-carboxamide

Step 1

N-(Tetrahydro-2H-pyran-4-yl)-3-(4,5,6,7-tetrahydrobenzo[d]thiazol-2-yl)-1-((2-(trimethylsilyl)ethoxy)methyl)-1H-pyrazole-4-carboxamide

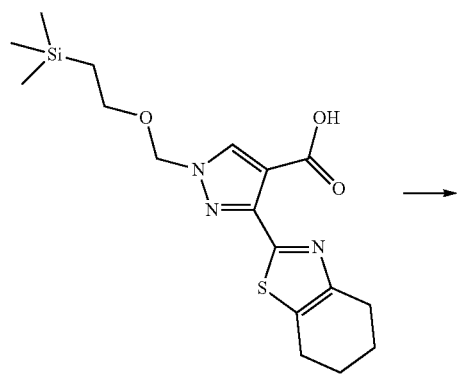

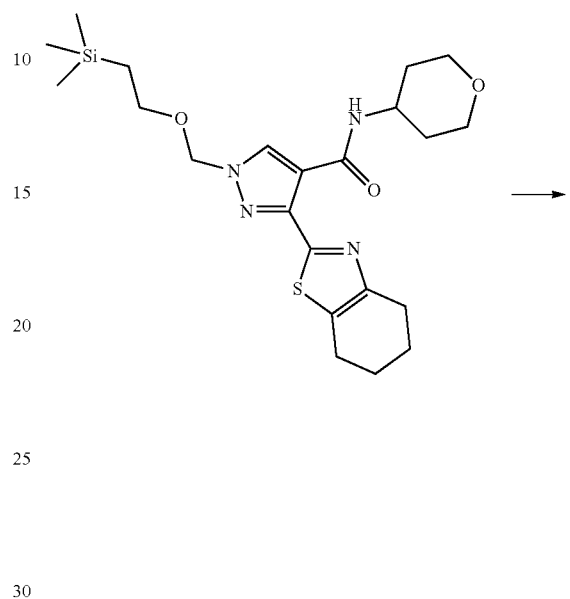

To a solution of 3-(4,5,6,7-tetrahydrobenzo[d]thiazol-2-yl)-1-((2-(trimethylsilyl)ethoxy)methyl)-1H-pyrazole-4-carboxylic acid (82 mg, 216 μmol) in DMF (2 mL) was added tetrahydro-2H-pyran-4-amine (65.6 mg, 648 μmol), HATU (123 mg, 324 μmol) and DIPEA (83.8 mg, 113 μL, 648 μmol). The mixture was stirred at r.t. for 16 h then quenched with 10% citric acid and diluted with ethyl acetate and sodium bicarbonate. The organic phase was separated and washed with sodium bicarbonate and brine, then concentrated in vacuo and purified by chromatography (silica, 50-90% ethyl acetate in hexanes) to give N-(tetrahydro-2H-pyran-4-yl)-3-(4,5,6,7-tetrahydrobenzo[d]thiazol-2-yl)-1-((2-(trimethylsilyl)ethoxy)methyl)-1H-pyrazole-4-carboxamide (79 mg, 171 μmol, 79%) as a white solid. $^1$H NMR (400 MHz, CHLOROFORM-d) δ ppm 11.25 (s, 1 H), 8.24 (s, 1 H), 5.44 (s, 2 H), 4.21 (m, 1 H), 4.03 (m, 2 H), 3.62 (t, J=8.5 Hz, 2 H), 3.58 (m, 2 H), 2.84 (m, 4 H), 2.06 (d, J=13.4 Hz, 2 H), 1.93 (m, 4 H), 1.71 (m, 2 H), 0.95 (t, J=8.3 Hz, 2 H), 0.01 (s, 9 H).

Step 2

N-(Tetrahydro-2H-pyran-4-yl)-3-(4,5,6,7-tetrahydrobenzo[d]thiazol-2-yl)-1H-pyrazole-4-carboxamide

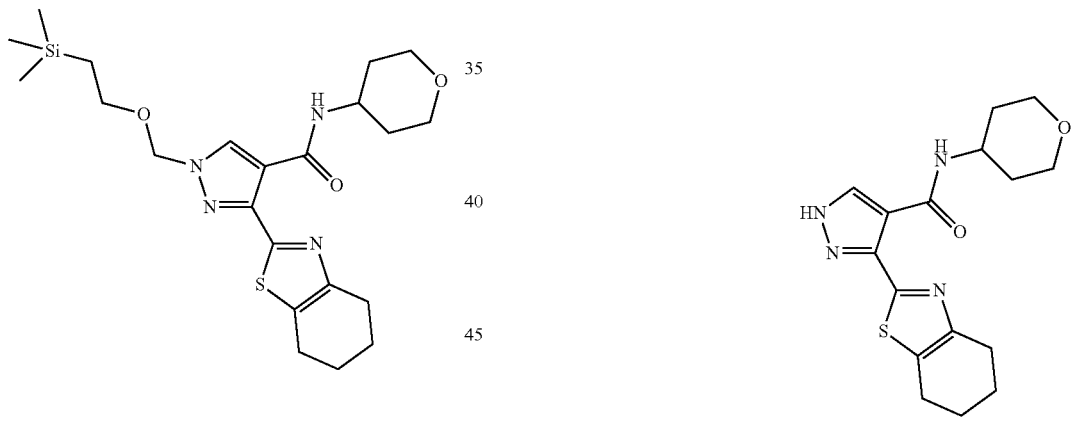

To a solution of N-(tetrahydro-2H-pyran-4-yl)-3-(4,5,6,7-tetrahydrobenzo[d]thiazol-2-yl)-1-((2-(trimethylsilyl)ethoxy)methyl)-1H-pyrazole-4-carboxamide (79 mg, 171 μmol) in dichloromethane (2.6 mL) was added trifluoroacetic acid (389 mg, 263 μL, 3.41 mmol). The mixture was stirred at r.t. for 16 h then concentrated in vacuo. The residue was redissolved with dichloromethane (3 mL), methanol (1.5 mL) and ammonium hydroxide (500 μL) and stirred at r.t for 1 h. The mixture was then concentrated in vacuo, triturated with water, filtered and washed with water and ether to give N-(tetrahydro-2H-pyran-4-yl)-3-(4,5,6,7-tetrahydrobenzo[d]thiazol-2-yl)-1H-pyrazole-4-carboxamide (40 mg, 120 μmol, 71%) as a white solid. $^1$H NMR (400 MHz, DMSO-d) δ ppm 13.43 (s, 1 H), 10.93 (s, 1 H), 8.33 (s, 1 H), 4.00 (m, 1 H), 3.89 (m, 2 H), 3.46 (t, J=11.7 Hz, 2 H), 2.80 (m 4 H), 1.88 (m, 6 H), 1.52 (m, 2 H); MS (EI/CI) m/z: 333.0 [M+H].

Example 23

N-(1-Methylpiperidin-4-yl)-3-(4,5,6,7-tetrahydrobenzo[d]thiazol-2-yl)-1H-pyrazole-4-carboxamide

Step 1

N-(1-Methylpiperidin-4-yl)-3-(4,5,6,7-tetrahydrobenzo[d]thiazol-2-yl)-1-((2-(trimethylsilyl)ethoxy)methyl)-1H-pyrazole-4-carboxamide

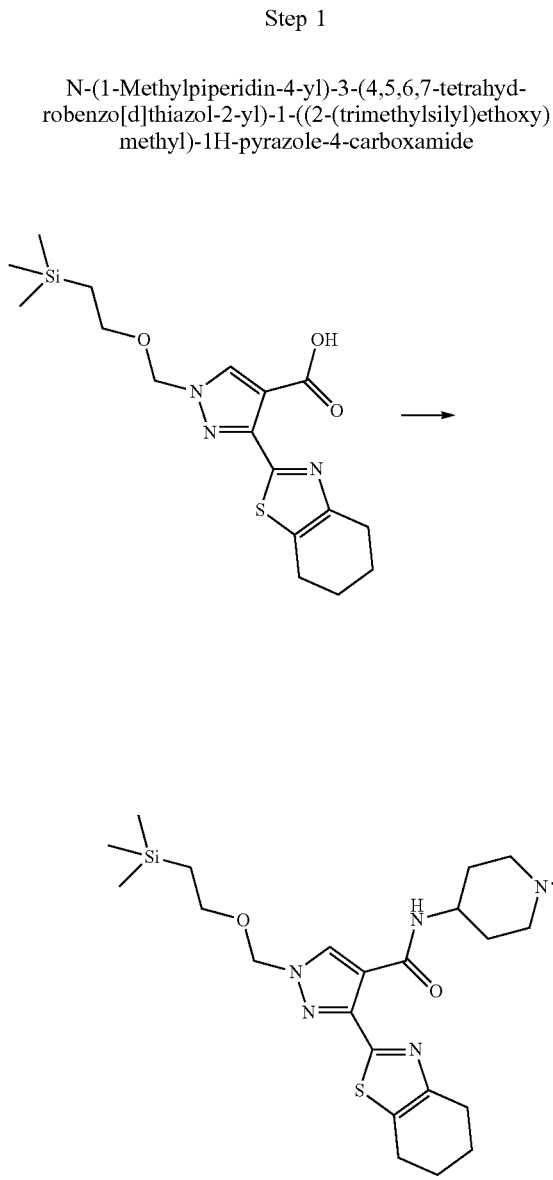

To a solution of 3-(4,5,6,7-tetrahydrobenzo[d]thiazol-2-yl)-1-((2-(trimethylsilyl)ethoxy)methyl)-1H-pyrazole-4-carboxylic acid (82 mg, 216 μmol) in DMF (2.00 mL) was added 1-methylpiperidin-4-amine (74.0 mg, 648 μmol), HATU (123 mg, 324 μmol) and DIPEA (83.8 mg, 113 μl, 648 μmol). The mixture was stirred at r.t. for 16 h, quenched with 10% citric acid, and diluted with ethyl acetate and sodium bicarbonate. The organic phase was separated, washed with sodium bicarbonate and brine, concentrated in vacuo, and purified by chromatography (silica, 5-10% methanol in dichloromethane to give N-(1-methylpiperidin-4-yl)-3-(4,5,6,7-tetrahydrobenzo[d]thiazol-2-yl)-1-((2-(trimethylsilyl)ethoxy)methyl)-1H-pyrazole-4-carboxamide (55 mg, 116 μmol, 54%) as a white solid. MS (EI/CI) m/z: 476.2 [M+H].

Step 2

N-(1-Methylpiperidin-4-yl)-3-(4,5,6,7-tetrahydrobenzo[d]thiazol-2-yl)-1H-pyrazole-4-carboxamide

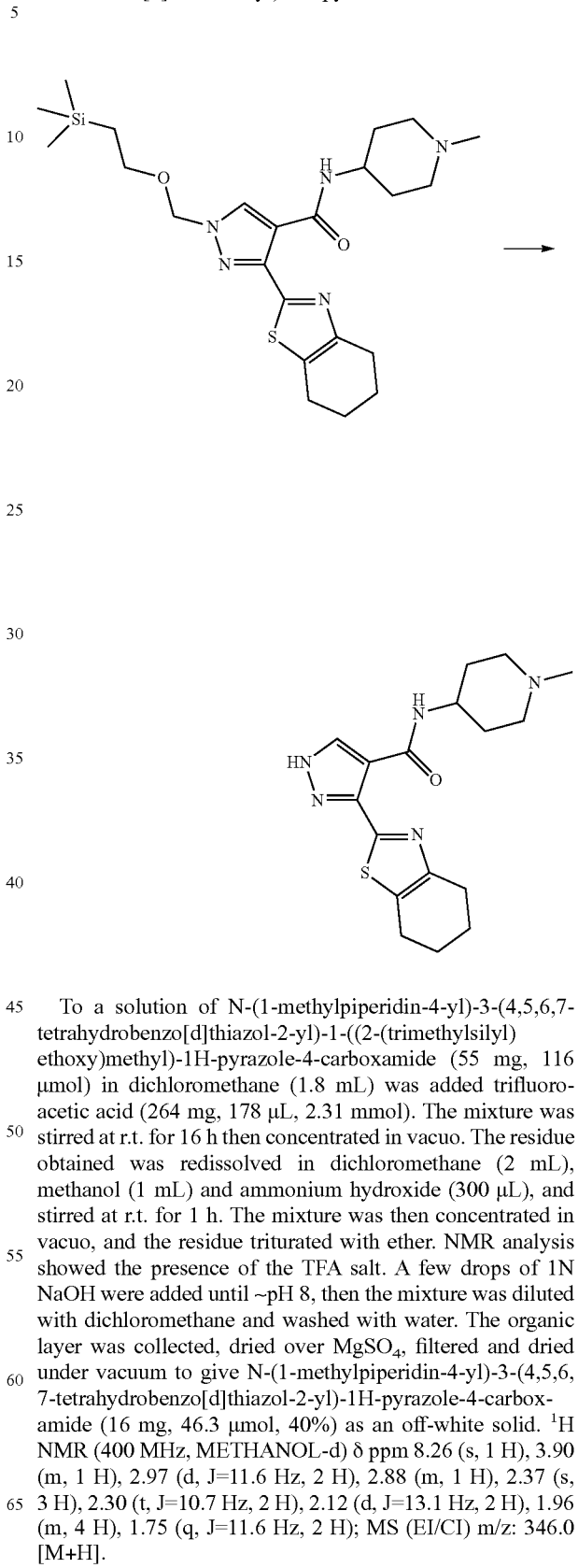

To a solution of N-(1-methylpiperidin-4-yl)-3-(4,5,6,7-tetrahydrobenzo[d]thiazol-2-yl)-1-((2-(trimethylsilyl)ethoxy)methyl)-1H-pyrazole-4-carboxamide (55 mg, 116 μmol) in dichloromethane (1.8 mL) was added trifluoroacetic acid (264 mg, 178 μL, 2.31 mmol). The mixture was stirred at r.t. for 16 h then concentrated in vacuo. The residue obtained was redissolved in dichloromethane (2 mL), methanol (1 mL) and ammonium hydroxide (300 μL), and stirred at r.t. for 1 h. The mixture was then concentrated in vacuo, and the residue triturated with ether. NMR analysis showed the presence of the TFA salt. A few drops of 1N NaOH were added until ~pH 8, then the mixture was diluted with dichloromethane and washed with water. The organic layer was collected, dried over MgSO$_4$, filtered and dried under vacuum to give N-(1-methylpiperidin-4-yl)-3-(4,5,6,7-tetrahydrobenzo[d]thiazol-2-yl)-1H-pyrazole-4-carboxamide (16 mg, 46.3 μmol, 40%) as an off-white solid. $^1$H NMR (400 MHz, METHANOL-d) δ ppm 8.26 (s, 1 H), 3.90 (m, 1 H), 2.97 (d, J=11.6 Hz, 2 H), 2.88 (m, 1 H), 2.37 (s, 3 H), 2.30 (t, J=10.7 Hz, 2 H), 2.12 (d, J=13.1 Hz, 2 H), 1.96 (m, 4 H), 1.75 (q, J=11.6 Hz, 2 H); MS (EI/CI) m/z: 346.0 [M+H].

Example 24

Tetrahydro-pyran-4-carboxylic acid (3-benzothiazol-2-yl-1H-pyrazol-4-yl)-amide

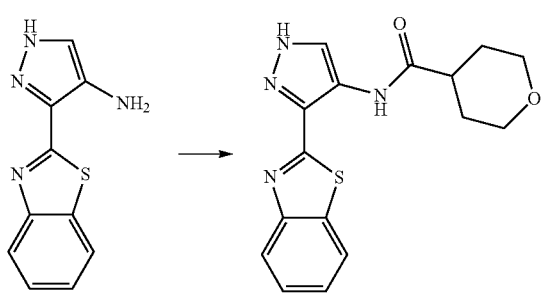 [SMILES: Nc1c[nH]nc1-c1nc2ccccc2s1 ; O=C(Nc1c[nH]nc1-c1nc2ccccc2s1)C1CCOCC1]

Tetrahydro-pyran-4-carboxylic acid (3-benzothiazol-2-yl-1H-pyrazol-4-yl)-amide (92 mg, 30%) was synthesized as white solid from 3-benzothiazol-2-yl-1H-pyrazol-4-ylamine (200 mg, 0.926 mmol) and tetrahydro-pyran-4-carbonyl chloride (0.35 mL, 3.06 mmol) following the procedure described for N-[3-(1H-benzoimidazol-2-yl)-1H-pyrazol-4-yl]-isobutyramide (Example 29). MS (EI/CI) m/z: 329.4 [M+H].

Example 25

Cyclobutanecarboxylic acid (3-benzothiazol-2-yl-1H-pyrazol-4-yl)-amide

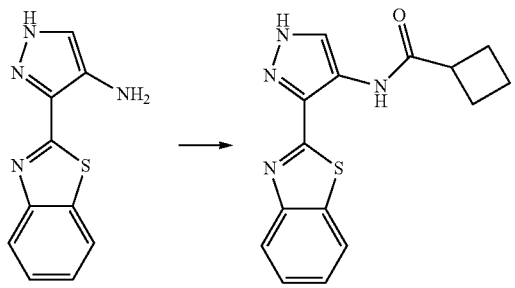 [SMILES: Nc1c[nH]nc1-c1nc2ccccc2s1 ; O=C(Nc1c[nH]nc1-c1nc2ccccc2s1)C1CCC1]

Cyclobutanecarboxylic acid (3-benzothiazol-2-yl-1H-pyrazol-4-yl)-amide (108 mg, 39%) was synthesized as white solid from 3-benzothiazol-2-yl-1H-pyrazol-4-ylamine (200 mg, 0.926 mmol) and cyclobutanecarbonyl chloride (0.35 mL, 3.06 mmol) following the procedure described for N-[3-(1H-benzoimidazol-2-yl)-1H-pyrazol-4-yl]-isobutyramide (Example 29). MS (EI/CI) m/z: 299.4 [M+H].

Example 26

Acetic acid 2-(3-benzothiazol-2-yl-1H-pyrazol-4-ylcarbamoyl)-2-methyl-propyl ester

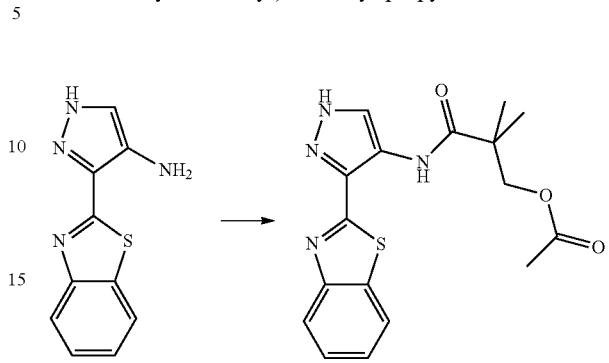

Acetic acid 2-(3-benzothiazol-2-yl-1H-pyrazol-4-ylcarbamoyl)-2-methyl-propyl ester (210 mg, 51%) was synthesized as off white solid from 3-benzothiazol-2-yl-1H-pyrazol-4-ylamine (250 mg, 1.157 mmol) and acetic acid 2-chlorocarbonyl-2-methyl-propyl ester (Prepared as described in Example 33) (680 mg, 3.82 mmol) following the procedure described for N-[3-(1H-benzoimidazol-2-yl)-1H-pyrazol-4-yl]-isobutyramide (Example 29). MS (EI/CI) m/z: 359.2 [M+H].

Example 27

N-(3-Benzothiazol-2-yl-1H-pyrazol-4-yl)-3-hydroxy-2,2-dimethyl-propionamide

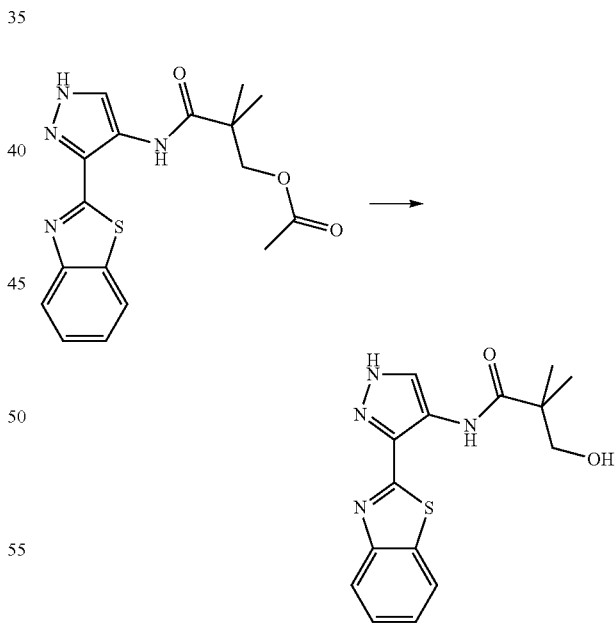

N-(3-Benzothiazol-2-yl-1H-pyrazol-4-yl)-3-hydroxy-2,2-dimethyl-propionamide (65.0 mg, 74%) was synthesized as white solid from acetic acid 2-(3-benzothiazol-2-yl-1H-pyrazol-4-ylcarbamoyl)-2-methyl-propyl ester (100 mg, 0.279 mmol) following the procedure described for N-[3-(1H-benzoimidazol-2-yl)-1H-pyrazol-4-yl]-3-hydroxy-2,2-dimethyl-propionamide (Example 34). MS (EI/CI) m/z: 317.2 [M+H].

Example 28

4-(5-Methyl-1H-benzoimidazol-2-yl)-thiazole-5-carboxylic acid tert-butylamide

Step 1

2-(5-Bromo-thiazol-4-yl)-5-methyl-1H-benzoimidazole

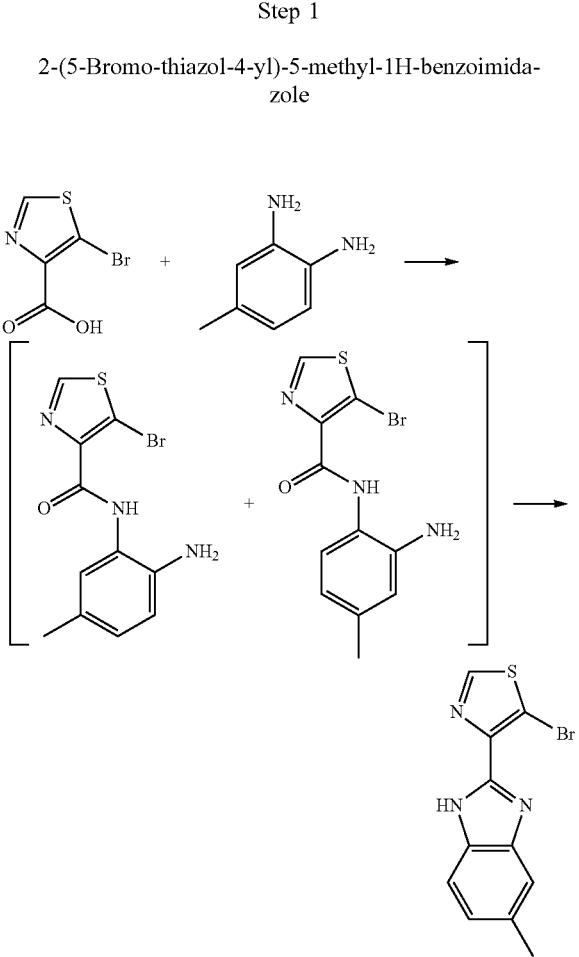

A solution of 5-bromo-thiazole-4-carboxylic acid (1.37 g, 6.59 mmol, commercially available from Combi-blocks), diisopropylethylamine (1.49 mL, 8.57 mmol), 4-methylbenzene-1,2-diamine (0.88 g, 7.25 mmol) in DMF (11 mL) at room temperature was treated with TBTU (2.75 g, 8.57 mmol) and the mixture stirred at room temperature for 18 h. The solvents were then evaporated under vacuum and the residue partitioned between ethyl acetate and saturated solution of sodium bicarbonate, the organics were collected and dried with magnesium sulfate and then concentrated under vacuum. The crude mixture was dissolved in acetic acid (12 mL), transferred to microwave vial and the mixture was heated at 150° C. in a microwave reactor for 1.5 h. After solvent evaporation, the residue was dissolved in dichloromethane, washed with saturated solution of sodium bicarbonate, dried with magnesium sulfate and concentrated under vacuum to yield 2-(5-bromo-thiazol-4-yl)-5-methyl-1H-benzoimidazole (1.93 g, crude, quantitative yield for two steps) as a beige solid that was used into the next step without further purification. $^1$H NMR (CHLOROFORM-d) δ: 8.82 (s, 1H), 7.64 (d, J=7.9 Hz, 1H), 7.47 (s, 1H), 7.15 (d, J=8.3 Hz, 1H), 2.50 (s, 3H); LCMS (EI/CI) m/z: 293.9, 295.9 [M+H]$^+$.

Step 2

4-(5-Methyl-1H-benzoimidazol-2-yl)-thiazole-5-carboxylic acid

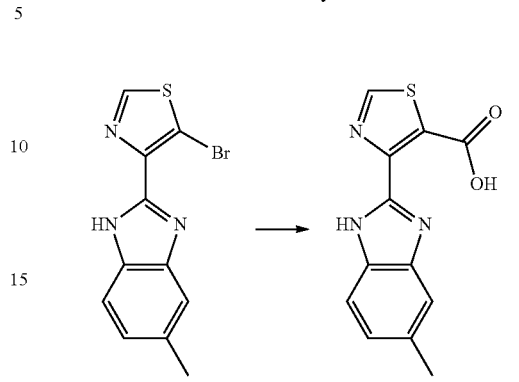

A solution of 2-(5-bromo-thiazol-4-yl)-5-methyl-1H-benzoimidazole (0.48 g, 1.65 mmol) in anhydrous THF (20 mL) under argon atmosphere was cooled in a dry-ice/acetone bath. A solution of n-butyillithium (1.6M in hexanes, 2.27 mL, 3.63 mmol) was added drop-wise and the reaction continued for 30 min in the ice-bath. Then, a few pieces of dry ice were added to the reaction mixture and the mixture warmed to room temperature with stirring. The reaction was quenched by adding a solution of 1N HCl (20 mL) and the product was extracted with dichloromethane (4×30 mL). The combined organic layers were dried over anhydrous MgSO$_4$ and concentrated under reduced pressure to give crude 4-(5-methyl-1H-benzoimidazol-2-yl)-thiazole-5-carboxylic acid (428 mg crude, ~40%), as dark green solid, which was used directly for the next step without further purification. $^1$H NMR (METHANOL-d$_4$) δ: 9.27-9.40 (m, 1H), 7.73-7.84 (m, 1H), 7.69 (s, 1H), 7.48 (d, J=8.3 Hz, 1H), 2.58 (d, J=2.3 Hz, 3H); LCMS (EI/CI) m/z: 257.9 [M−H]$^−$.

Step 3

4-(5-Methyl-1H-benzoimidazol-2-yl)-thiazole-5-carboxylic acid tert-butylamide

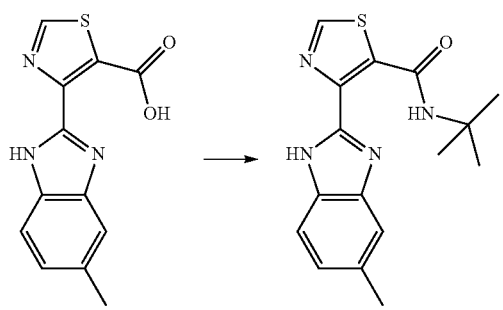 [SMILES: Cc1ccc2[nH]c(-c3ncsc3C(=O)O)nc2c1 ; Cc1ccc2[nH]c(-c3ncsc3C(=O)NC(C)(C)C)nc2c1]

To a solution of 4-(5-methyl-1H-benzoimidazol-2-yl)-thiazole-5-carboxylic acid (60 mg, 0.23 mmol) and HATU (149 mg, 0.39 mmol) in DMF (2 mL) was added tert-butylamine (0.1 mL, 0.92 mmol) and reaction stirred at room temperature for 8 h. The solvents were removed under high vacuum and the crude residue was purified by chromatography (silica, 0 to 5% of a 9:1 MeOH:ammonium hydroxide solution in dichloromethane, 20 min) to yield 4-(5-methyl- 1H-benzoimidazol-2-yl)-thiazole-5-carboxylic acid tert-butylamide (0.072 g, 59%) as a white solid. $^1$H NMR (DMSO-$d_6$) δ: 13.19 (br. s., 1H), 12.76 (s, 1H), 9.32 (s, 1H), 7.30-7.68 (m, 2H), 7.14 (br. s., 1H), 2.44 (s, 3H), 1.50 (s, 9H); LCMS (EI/CI) m/z: 315.0 [M+H]$^+$.

Example 29

N-[3-(1M-Benzoimidazol-2-yl)-1H-pyrazol-4-yl]-isobutyramide

Step 1

2-(4-Nitro-1H-pyrazol-3-yl)-1H-benzoimidazole

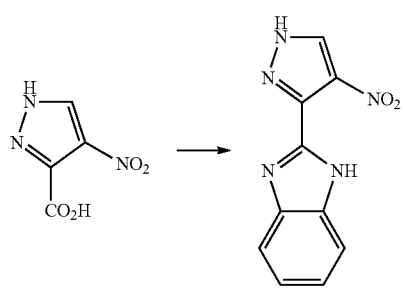 [SMILES: O=C(O)c1n[nH]cc1[N+](=O)[O-] ; O=[N+]([O-])c1c[nH]nc1-c1nc2ccccc2[nH]1]

A mixture of 4-nitro-1H-pyrazole-3-carboxylic acid (5.0 g, 31.8 mmol), 1,2-phenylenediamine (3.79 g, 35.0 mmol), EDC (7.30 g, 38.2 mmol) and HOBt (5.16 g, 38.2 mmol) in DMF (65 mL) was stirred at room temperature for 24 h. After which the solvent was reduced to a third of its original volume, and the remaining mixture was diluted with AcOH (60 mL) and refluxed for 3 h. Upon cooling, the solvents were removed under reduced pressure and water was added to the residue. The resultant precipitate was collected by filtration and washed thoroughly with water. The solid was dried through azeotroping with toluene to give 2-(4-nitro-1H-pyrazol-3-yl)-1H-benzoimidazole (5 g, 69%) as a yellow solid. LCMS (EI/CI) m/z: 228.0 [M+H]$^+$.

Step 2

3-(1H-Benzoimidazol-2-yl)-1H-pyrazol-4-ylamine

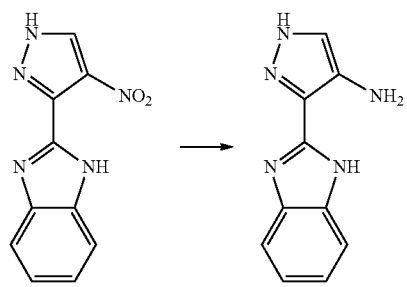 [SMILES: O=[N+]([O-])c1c[nH]nc1-c1nc2ccccc2[nH]1 ; Nc1c[nH]nc1-c1nc2ccccc2[nH]1]

A mixture of 2-(4-nitro-1H-pyrazol-3-yl)-1H-benzoimidazole (3.5 g, 15.3 mmol) and 10% Pd—C (0.3 g) in DMF (40 mL) was subjected to an atmosphere of hydrogen (balloon pressure) at room temperature for 20 h. The mixture was then filtered through celite and the filtrate concentrated under reduced pressure. The residue was partitioned between ethyl acetate and water, the organic layer was separated, dried over anhydrous Na$_2$SO$_4$, and concentrated under reduced pressure to give crude 3-(1H-benzoimidazol-2-yl)-1H-pyrazol-4-ylamine (2.5 g crude, ~82%) as a brown solid, which was used directly in the next step without further purification. LCMS (EI/CI) m/z: 200.2 [M+H]$^+$.

Step 3

N-[3-(1H-Benzoimidazol-2-yl)-1H-pyrazol-4-yl]-isobutyramide

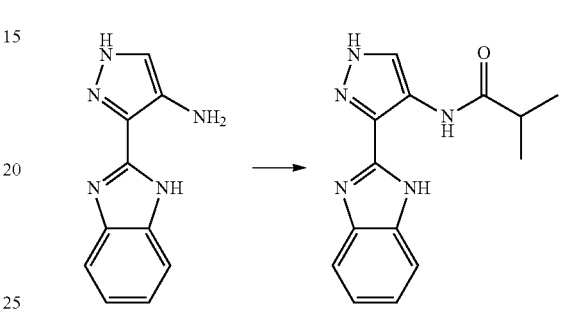

To a solution of 3-(1H-benzoimidazol-2-yl)-1H-pyrazol-4-ylamine (300 mg, 1.51 mmol) in pyridine (8 mL), was added isobutyryl chloride (0.52 mL, 4.98 mmol) in dichloromethane (8 mL) at 0° C. The mixture was stirred at room temperature for 20 h, after which water was added and the mixture extracted with ethyl acetate (3×15 mL). The combined organic phases were washed with water, dried over anhydrous Na$_2$SO$_4$, and then concentrated under reduced pressure. The crude mass was redissolved in acetonitrile (5 mL) and methanol (10 mL) then 25% aqueous ammonium hydroxide solution (10 mL) was added to it. This mixture was stirred at r.t. for 3 h, then partitioned between EtOAc and water. The organic phase was collected and washed with 1N HCl. The organic phase was then poured over solid sodium bicarbonate, subsequently dried with anhydrous Na$_2$SO$_4$, and concentrated under reduced pressure. The crude mass was purified by chromatography (silica, EtOAc in hexanes) to give N-[3-(1H-benzoimidazol-2-yl)-1H-pyrazol-4-yl]-isobutyramide as off white solid (85 mg, 21%). LCMS (EI/CI) m/z: 269.8 [M+H]$^+$.

Example 30

N-[3-(1H-Benzoimidazol-2-yl)-1H-pyrazol-4-yl]-2,2-dimethyl-propionamide

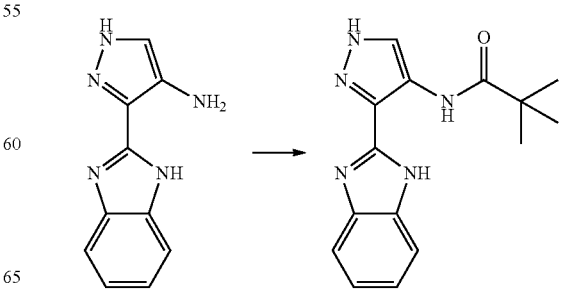

N-[3-(1H-Benzoimidazol-2-yl)-1H-pyrazol-4-yl]-2,2-dimethyl-propionamide (180 mg, 42%) was synthesized as off white solid from 3-(1H-benzoimidazol-2-yl)-1H-pyrazol-4-ylamine (300 mg, 1.51 mmol) and pivaloyl chloride (0.61 mL, 4.98 mmol) following the procedure described for N-[3-(1H-benzoimidazol-2-yl)-1H-pyrazol-4-yl]-isobutyramide (Example 29). LCMS (EI/CI) m/z: 284.0 [M+H]+.

Example 31

Cyclopentanecarboxylic acid [3-(1H-benzoimidazol-2-yl)-1H-pyrazol-4-yl]-amide

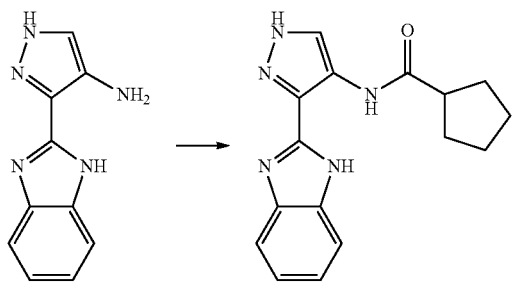 [SMILES: Nc1c[nH]nc1-c1nc2ccccc2[nH]1 ; O=C(Nc1c[nH]nc1-c1nc2ccccc2[nH]1)C1CCCC1]

Cyclopentanecarboxylic acid [3-(1H-benzoimidazol-2-yl)-1H-pyrazol-4-yl]-amide (255 mg, 57%) was synthesized as white solid from 3-(1H-benzoimidazol-2-yl)-1H-pyrazol-4-ylamine (300 mg, 1.51 mmol) and cyclopentanecarbonyl chloride (0.63 mL, 4.98 mmol) following the procedure described for N-[3-(1H-benzoimidazol-2-yl)-1H-pyrazol-4-yl]-isobutyramide (Example 29). LCMS (EI/CI) m/z: 296.2 [M+H]+.

Example 32

Tetrahydro-pyran-4-carboxylic acid [3-(1H-benzoimidazol-2-yl)-1H-pyrazol-4-yl]-amide

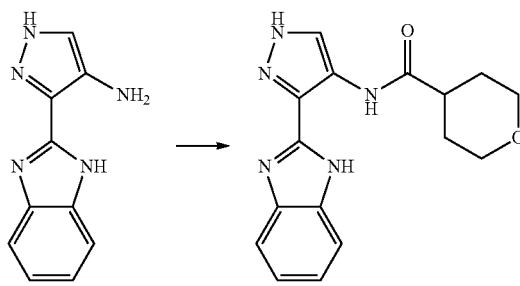

Tetrahydro-pyran-4-carboxylic acid [3-(1H-benzoimidazol-2-yl)-1H-pyrazol-4-yl]-amide (100.0 mg, 32%) was synthesized as light brown solid from 3-(1H-benzoimidazol-2-yl)-1H-pyrazol-4-ylamine (200 mg, 1.01 mmol) and tetrahydro-pyran-4-carbonyl chloride (494 mg, 4.98 mmol) following the procedure described for N-[3-(1H-benzoimidazol-2-yl)-1H-pyrazol-4-yl]-isobutyramide (Example 29). LCMS (EI/CI) m/z: 312.3 [M+H]+.

Example 33

N-[3-(1H-Benzoimidazol-2-yl)-1H-pyrazol-4-yl]-3-hydroxy-2,2-dimethyl-propionamide Step 1

2-Acetoxymethyl-2-methyl-propionic acid

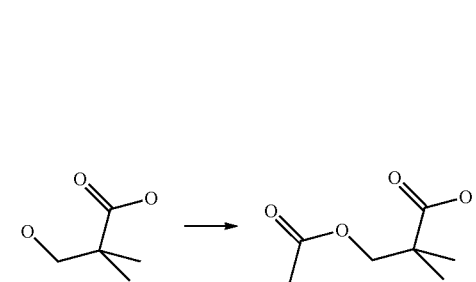

2,2-Dimethyl-3-hydroxypropionic acid (1.0 g, 8.48 mmol) was dissolved in pyridine (6 mL) at 0° C. and acetyl chloride (0.91 mL, 12.7 mmol) was added dropwise at this temperature. The mixture was warmed to room temperature and stirred for 4 h. After which a solution of 1NHCl was added to adjust the pH (to ~3-4). The mixture was extracted with EtOAc (3×30 mL) and the combined organic layer dried over anhydrous Na2SO4. Concentration under reduced pressure then gave 2-acetoxymethyl-2-methyl-propionic acid (1.1 g, 81%) as an off-white crystalline solid which was used directly in the next reaction without further purification.

Step 2

Acetic acid 2-chlorocarbonyl-2-methyl-propyl ester

A solution of 2-acetoxymethyl-2-methyl-propionic acid (2 g, 12.5 mmol) in benzene (20 mL) was cooled to 0° C. and oxalyl chloride (1.61 mL, 18.7 mmol) was added dropwise. The mixture was warmed to room temperature and stirred for 3 h. After which the mixture was concentrated under reduced pressure to give acetic acid 2-chlorocarbonyl-2-methyl-propyl ester as a yellow liquid (2.1 g crude, ~94%). This material was used directly without further purification.

Step 3

Acetic acid 2-[3-(1H-benzoimidazol-2-yl)-1H-pyrazol-4-ylcarbamoyl]-2-methyl-propyl ester

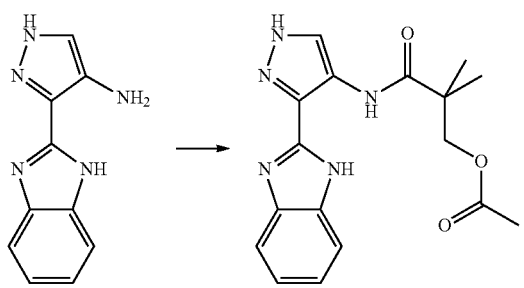 [SMILES: Nc1c[nH]nc1-c1nc2ccccc2[nH]1 ; CC(=O)OCC(C)(C)C(=O)Nc1c[nH]nc1-c1nc2ccccc2[nH]1]

Acetic acid 2-[3-(1H-benzoimidazol-2-yl)-1H-pyrazol-4-ylcarbamoyl]-2-methyl-propyl ester (330 mg, 48%) was synthesized as light yellow solid from 3-(1H-benzoimidazol-2-yl)-1H-pyrazol-4-ylamine (400 mg, 2.1 mmol) and acetic acid 2-chlorocarbonyl-2-methyl-propyl ester (1.18 g, 6.63 mmol) following the procedure described for N-[3-(1H-benzoimidazol-2-yl)-1H-pyrazol-4-yl]-isobutyramide (Example 29). LCMS (EI/CI) m/z: 342.1 [M+H]$^+$.

Example 34

N-[3-(1H-Benzoimidazol-2-yl)-1H-pyrazol-4-yl]-3-hydroxy-2,2-dimethyl-propionamide

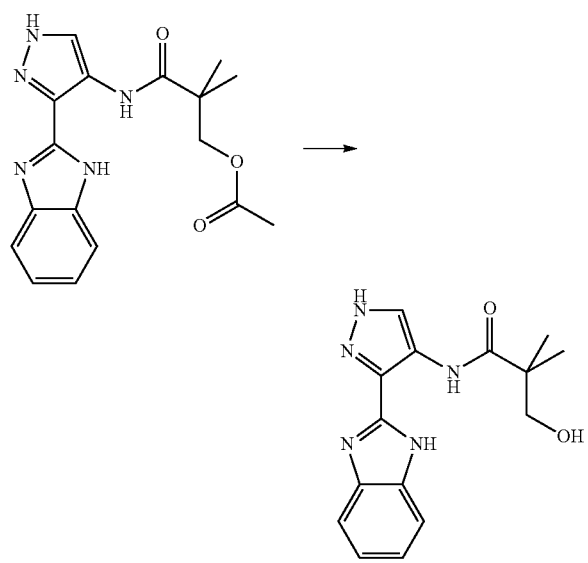

To a solution of acetic acid 2-[3-(1H-benzoimidazol-2-yl)-1H-pyrazol-4-ylcarbamoyl]-2-methyl-propyl ester (95 mg, 0.279 mmol) in MeOH (8 mL) was added K$_2$CO$_3$ (231 mg, 1.67 mmol). The mixture was stirred at room temperature for 2 h, then concentrated under reduced pressure. The residue obtained was diluted with ethyl acetate (25 mL), was washed with water (2×10 mL), dried over anhydrous Na$_2$SO$_4$, and concentrated under reduced pressure. The crude mass was then purified by chromatography (silica, EtOAc in hexanes) to give N-[3-(1H-benzoimidazol-2-yl)-1H-pyrazol-4-yl]-3-hydroxy-2,2-dimethyl-propionamide (72 mg, 86%) as a light yellow solid. LCMS (EI/CI) m/z: 300.2 [M+H]$^+$.

Example 35

3-(1H-Benzoimidazol-2-yl)-1H-pyrazole-4-carboxylic acid isopropylamide

Step 1

4-tert-Butoxy-3-oxo-butyric acid ethyl ester

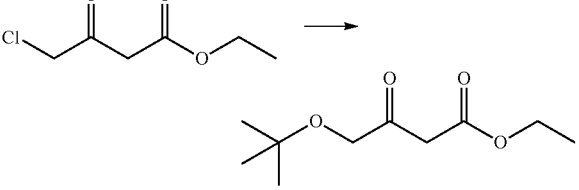

To a solution of 2-methyl-propan-2-ol (25 g, 336 mmol) in DMF (250 mL) at 0° C. was added NaH (60%) (33.6 g, 841 mmol) in five portions. To this was slowly added 4-chloro-3-oxo-butyric acid ethyl ester (23.1 mL, 168 mmol) and the reaction mixture was stirred at 0° C. for 1 h and then warmed to room temperature and stirred for an additional 2 h. The mixture was then poured into ice water (200 mL) and extracted with EtOAc (3×100 mL). The organic extracts were combined and dried over anhydrous Na$_2$SO$_4$, concentrated under reduced pressure, and purified by chromatography (silica, EtOAc in hexanes) to give 4-tert-butoxy-3-oxo-butyric acid ethyl ester (14 g, 21%) as a sticky brown solid.

Step 2

3-tert-Butoxymethyl-1H-pyrazole-4-carboxylic acid ethyl ester

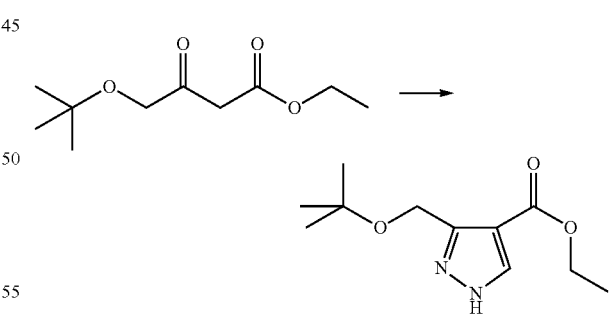

To a solution of 4-tert-butoxy-3-oxo-butyric acid ethyl ester (14 g, 69 mmol) in toluene (100 mL) was added dimethylformamide dimethyl acetal (14 mL). The mixture heated at 65° C. for 3 h. Upon cooling, the volatiles were removed under reduced pressure and the residue was then redissolved in acetic acid (20 mL), and hydrazine hydrate (5.06 mL, 104 mmol) was added. After stirring at room temperature for 3 h, the reaction mixture was poured into water (100 mL) and extracted with EtOAc (3×75 mL). The combined organic phases were dried over anhydrous Na$_2$SO$_4$, concentrated under reduced pressure and the crude mass was purified by chromatography (silica, EtOAc/hexanes) to give 3-tert-butoxymethyl-1H-pyrazole-4-carboxylic acid ethyl ester (6.5 g, 41%) as a brown liquid. LCMS (EI/CI) m/z: 227.2 [M+H]$^+$.

Step 3

3-Hydroxymethyl-1H-pyrazole-4-carboxylic acid ethyl ester

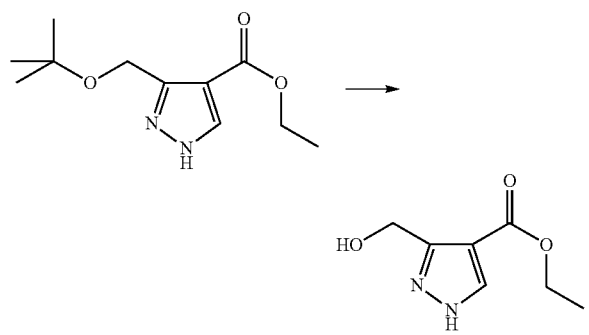

To a solution of 3-tert-butoxymethyl-1H-pyrazole-4-carboxylic acid ethyl ester (6.5 g, 28.8 mmol) in dichloromethane (100 mL) was added trifluoroactetic acid (50 mL). The mixture was then stirred at room temperature for 2 h and then concentrated in vacuo. The crude residue was poured into water (50 mL), neutralized with saturated aqueous sodium bicarbonate, and then extracted with EtOAc (3×50 mL). The combined organic extracts were dried over anhydrous Na$_2$SO$_4$ and concentrated under reduced pressure to give 3-hydroxymethyl-1H-pyrazole-4-carboxylic acid ethyl ester (5.3 g) as light brown liquid which was used directly in next step without further purification. LCMS (EI/CI) m/z: 171.2 [M+H]$^+$.

Step 4

3-Formyl-1H-pyrazole-4-carboxylic acid ethyl ester

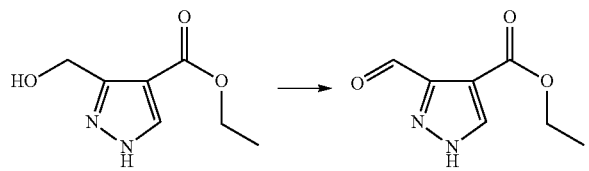

To a stirred solution of 3-hydroxymethyl-1H-pyrazole-4-carboxylic acid ethyl ester (4.5 g, 26.5 mmol) in EtOAc (50 mL) was added IBX (22.2 g, 79.4 mmol). The reaction mixture was heated to 60° C. for 6 h. Upon cooling, the mixture was filtered through a bed of celite and the filtrate was then concentrated under reduced pressure. The crude mass was purified by chromatography (silica, EtOAc in hexanes) to give 3-formyl-1H-pyrazole-4-carboxylic acid ethyl ester (2.0 g, 45%) as a gum. This semi-pure material was used directly in the next step without further purification.

Step 5

3-(1H-Benzoimidazol-2-yl)-1H-pyrazole-4-carboxylic acid ethyl ester

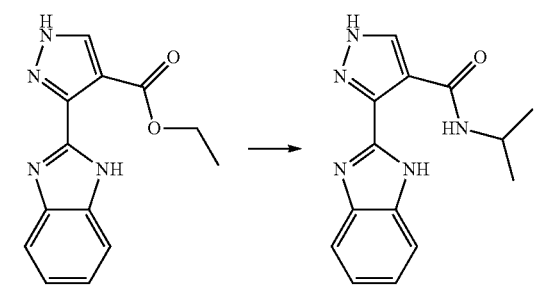 [SMILES: CCOC(=O)c1c[nH]nc1-c1nc2ccccc2[nH]1 ; CC(C)NC(=O)c1c[nH]nc1-c1nc2ccccc2[nH]1]

To a solution of 3-formyl-1H-pyrazole-4-carboxylic acid ethyl ester (2.0 g, 11.9 mmol) and benzene-1,2-diamine (2.3 g, 21.4 mmol) in DMF (20 mL) was added NaHSO$_3$ (4.2 g, 40.4 mmol). The reaction mixture was heated at 120° C. for 3 h. Upon cooling the mixture was poured onto crushed ice and the precipitate was collected by filtration. This solid was washed with saturated sodium bicarbonate followed by water, then dried under reduced pressure to give 3-(1H-benzoimidazol-2-yl)-1H-pyrazole-4-carboxylic acid ethyl ester (1.0 g, 33%) as a brown solid. LCMS (EI/CI) m/z: 257.2 [M+H]$^+$.

Step 6

3-(1H-Benzoimidazol-2-yl)-1H-pyrazole-4-carboxylic acid isopropylamide

To a mixture of (3-(1H-benzoimidazol-2-yl)-1H-pyrazole-4-carboxylic acid ethyl ester (200 mg, 0.391 mmol) and isopropyl amine (0.09 mL, 1.95 mmol) was added Me$_3$Al (2 M in THF, 0.19 mL, 0.391 mmol) under and argon atmosphere. The mixture was heated at 60° C. for 16 h, after which, the mixture was cooled, diluted with water (10 mL) and extracted with EtOAc (3×15 mL). The combined organic extracts were dried over anhydrous Na$_2$SO$_4$ and concentrated under reduced pressure. The crude residue was purified by preparative HPLC (NH$_4$OAc-CH$_3$CN solvent mixture) to give 3-(1H-benzoimidazol-2-yl)-1H-pyrazole-4-carboxylic acid isopropylamide (45 mg, 43%) as an off-white solid. LCMS (EI/CI) m/z: 270.4 [M+H]$^+$.

Example 36

3-(1H-Benzoimidazol-2-yl)-1H-pyrazole-4-carboxylic acid tert-butylamide

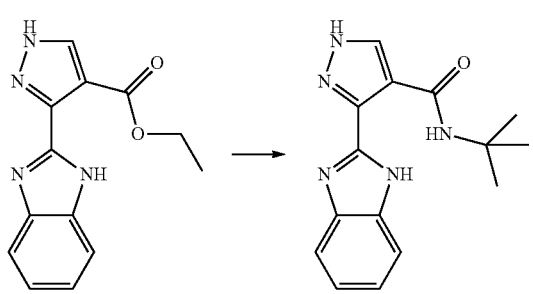 [SMILES: CCOC(=O)c1c[nH]nc1-c1nc2ccccc2[nH]1 ; CC(C)(C)NC(=O)c1c[nH]nc1-c1nc2ccccc2[nH]1]

3-(1H-Benzoimidazol-2-yl)-1H-pyrazole-4-carboxylic acid tert-butylamide (42 mg, 19%) was synthesized as an off-white solid from 3-(1H-benzoimidazol-2-yl)-1H-pyrazole-4-carboxylic acid ethyl ester (200 mg, 0.781 mmol) and tert-butyl amine (0.41 mL, 3.91 mmol) following the procedure described for 3-(1H-benzoimidazol-2-yl)-1H-pyrazole-4-carboxylic acid isopropylamide (Example 35). LCMS (EI/CI) m/z: 284.0 [M+H]$^+$.

Example 37

3-(1H-Benzoimidazol-2-yl)-1H-pyrazole-4-carboxylic acid (tetrahydro-pyran-4-yl)-amide

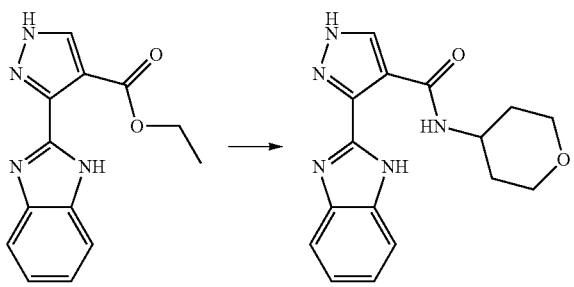 [SMILES: CCOC(=O)c1c[nH]nc1-c1nc2ccccc2[nH]1 ; O=C(NC1CCOCC1)c1c[nH]nc1-c1nc2ccccc2[nH]1]

3-(1H-Benzoimidazol-2-yl)-1H-pyrazole-4-carboxylic acid (tetrahydro-pyran-4-yl)-amide (30 mg, 16%) was synthesized as an off white solid from 3-(1H-benzoimidazol-2-yl)-1H-pyrazole-4-carboxylic acid ethyl ester (150 mg, 0.586 mmol) and tetrahydro-pyran-4-ylamine (118 mg, 1.17 mmol) following the procedure described for 3-(1H-benzoimidazol-2-yl)-1H-pyrazole-4-carboxylic acid isopropylamide (Example 35). LCMS (EI/CI) m/z: 312.2 [M+H]$^+$.

Example 38

3-(1H-Benzoimidazol-2-yl)-1H-pyrazole-4-carboxylic acid (2-hydroxy-1,1-dimethyl-ethyl)-amide

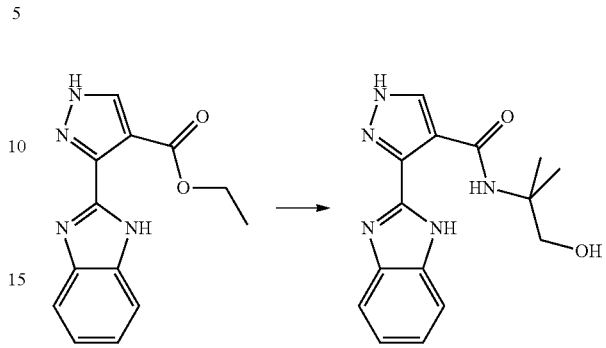

3-(1H-Benzoimidazol-2-yl)-1H-pyrazole-4-carboxylic acid (2-hydroxy-1,1-dimethyl-ethyl)-amide (60 mg, 26%) was synthesized as a white solid from 3-(1H-benzoimidazol-2-yl)-1H-pyrazole-4-carboxylic acid ethyl ester (200 mg, 0.781 mmol) and 2-amino-2-methyl-propan-1-ol (344 mg, 3.91 mmol) following the procedure described for 3-(1H-benzoimidazol-2-yl)-1H-pyrazole-4-carboxylic acid isopropylamide (Example 35). LCMS (EI/CI) m/z: 300.2 [M+H]$^+$.

Example 39

[4-(4-Methyl-1H-benzoimidazol-2-yl)-thiazol-5-yl]-pyridin-3-yl-amine

Step 1

5-(Pyridin-3-ylamino)-thiazole-4-carboxylic acid ethyl ester

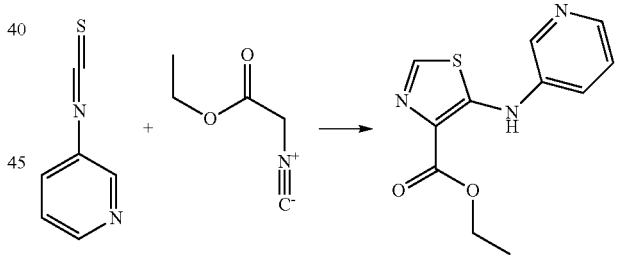

A solution of t-BuOK (5.45 g, 48.6 mmol) in THF (25 mL) was cooled to −40° C. To this mixture was added drop-wise, keeping the temperature below −35° C., a solution of isocyano-acetic acid ethyl ester (5 g, 44.2 mmol) and 3-isothiocyanato-pyridine (6.02 g, 44.2 mmol) in THF (50 mL). After the addition was complete, the reaction was warmed to −9° C. over 1 h. The reaction was then quenched by the addition of 2.5 mL of acetic acid. The reaction mixture was diluted with THF and ethyl acetate, filtered through a pad of celite and the filtrates evaporated. The residue was purified by chromatography (silica, 50% to 100% ethyl acetate in heptane, 30 min) to give 5-(pyridin-3-ylamino)-thiazole-4-carboxylic acid ethyl ester (4.85 g, 44%). 1H NMR (CHLOROFORM-d) δ: 9.86 (br. s., 1H), 8.62 (d, J=3.0 Hz, 1H), 8.37 (dd, J=4.7, 1.2 Hz, 1H), 8.05 (d, J=1.1 Hz, 1H), 7.60 (ddd, J=8.2, 2.8, 1.3 Hz, 1H), 7.33 (dd, J=8.3, 4.6 Hz, 1H), 4.47 (q, J=7.0 Hz, 2H), 1.47 (t, J=7.1 Hz, 3H); MS (EI/CI) m/z: 250.2 [M+H]$^+$.

Step 2

5-(Pyridin-3-ylamino)-thiazole-4-carboxylic acid

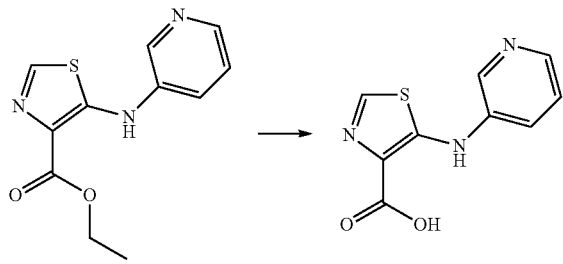 [SMILES: CCOC(=O)c1ncsc1Nc1cccnc1 ; O=C(O)c1ncsc1Nc1cccnc1]

A solution of 5-(pyridin-3-ylamino)-thiazole-4-carboxylic acid ethyl ester (1.56 g, 6.25 mmol) in methanol (12 mL) was treated with a solution of KOH (1.05 g, 18.7 mmol) in water (9 mL). The mixture was heated to 65° C. with stirring for 3 h. The methanol was evaporated, and the residual aqueous solution was then acidified to pH 4 with 1 N HCl. The gel that formed was treated with some methanol and the suspension sonicated until a loose off-white suspension was formed. The suspension was separated by filtration, washed with water, ethyl ether and then dried under high vacuum to give 5-(pyridin-3-ylamino)-thiazole-4-carboxylic acid (1.24 g, 90%) as an off-white solid. $^1$H NMR (DMSO-$d_6$) δ: 12.79 (br. s., 1H), 9.73 (s, 1H), 8.63 (d, J=2.7 Hz, 1H), 8.26-8.35 (m, 2H), 7.79 (ddd, J=8.3, 2.8, 1.3 Hz, 1H), 7.42 (dd, J=8.3, 4.6 Hz, 1H); MS (EI/CI) m/z: 220.2 [M−H]$^-$.

Step 3

[4-(4-Methyl-1H-benzoimidazol-2-yl)-thiazol-5-yl]-pyridin-3-yl-amine

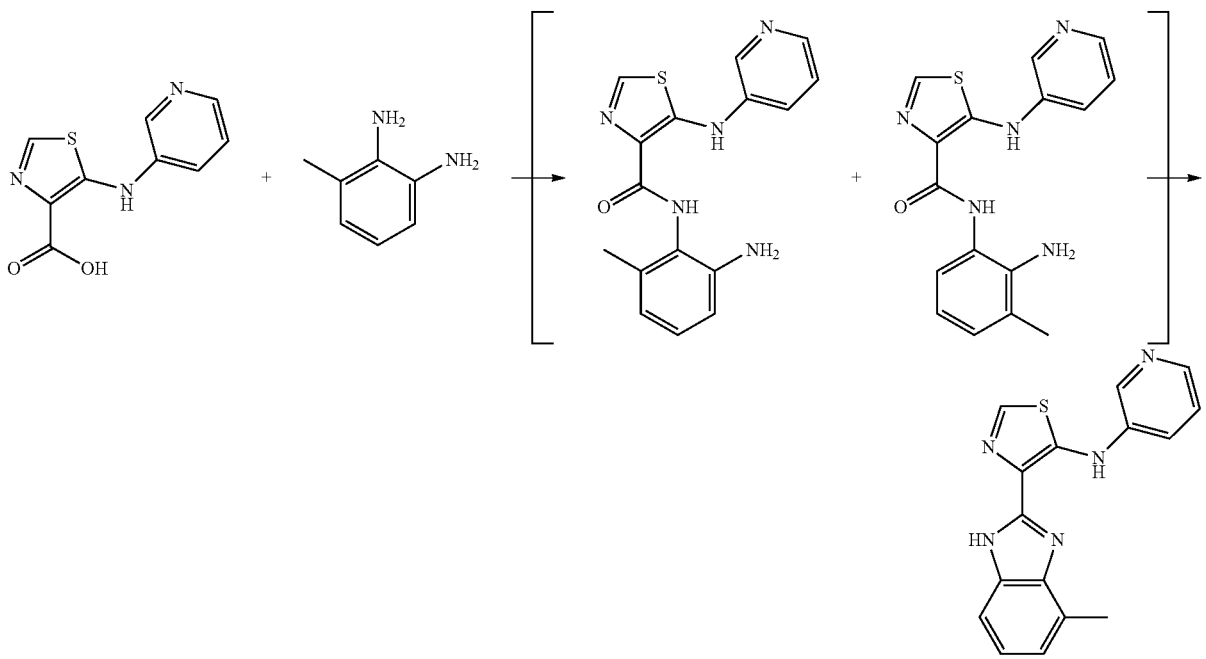

A solution of 5-(pyridin-3-ylamino)-thiazole-4-carboxylic acid (0.2 g, 0.90 mmol), diisopropylethylamine (0.24 mL, 1.17 mmol) and 3-methyl-benzene-1,2-diamine (0.122 g, 0.99 mmol) in DMF (3 mL) at room temperature was treated with TBTU (0.38 g, 1.17 mmol) and the mixture stirred for 18 h at room temperature. The solvents were evaporated under vacuum and residue obtained was then partitioned between ethyl acetate and a saturated solution of sodium bicarbonate. The organic phase was dried with magnesium sulfate and concentrated under vacuum. The crude mixture was dissolved in acetic acid (3 mL), transferred to microwave vial and the mixture was heated at 120° C. in a microwave reactor for 2 h. The mixture was cooled, concentrated in vacuo, and the residue then dissolved in dichloromethane, washed with saturated solution of sodium bicarbonate, dried with magnesium sulfate and concentrated under vacuum. The residue was purified by chromatography (silica, 0 to 5% methanol in dichloromethane) to yield [4-(4-methyl-1H-benzoimidazol-2-yl)-thiazol-5-yl]-pyridin-3-yl-amine (0.038 g, 14% over two steps) as a beige solid. $^1$H NMR (CHLOROFORM-d) δ: 8.73 (d, J=2.6 Hz, 1H), 8.32 (dd, J=4.5, 1.1 Hz, 1H), 8.20 (s, 1H), 7.69 (d, J=7.6 Hz, 1H), 7.47 (br. s., 1H), 7.36 (m, 2H), 7.22 (m, 2H), 7.11 (d, J=7.2 Hz, 1H), 2.68 (s, 3H); MS (EI/CI) m/z: 308.0 [M+H]$^+$.

Example 40

[4-(1H-Imidazo[4,5-c]pyridin-2-yl)-thiazol-5-yl]-pyridin-3-yl-amine

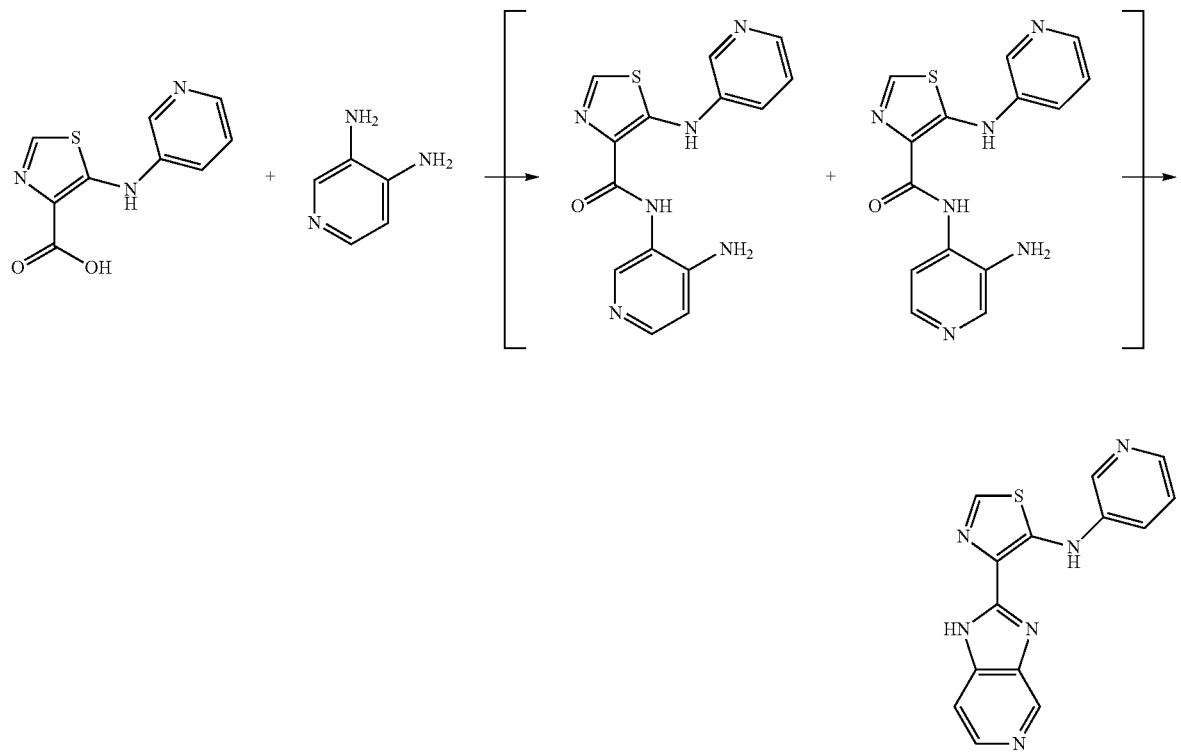

A solution of 5-(pyridin-3-ylamino)-thiazole-4-carboxylic acid (0.2 g, 0.90 mmol), diisopropylethylamine (0.24 mL, 1.17 mmol) and pyridine-3,4-diamine (0.108 g, 0.99 mmol) in DMF (3 mL) at room temperature was treated with TBTU (0.38 g, 1.17 mmol) and the mixture stirred for 18 h at room temperature. The mixture was concentrated under vacuum and the residue dissolved in ethyl acetate, washed with a saturated solution of sodium bicarbonate, and then dried with magnesium sulfate and concentrated under vacuum. The crude mixture was dissolved in acetic acid (3 mL), transferred to microwave vial and mixture was heated in a microwave reactor at 120° C. for 4.5 h, then at 150° C. for 1.5 h. The mixture was cooled, concentrated, and the residue obtained was then dissolved in dichloromethane, washed with saturated solution of sodium bicarbonate, dried with magnesium sulfate and concentrated under vacuum. The residue was purified by chromatography (silica, 0 to 10% methanol in dichloromethane, 20 min) to give [4-(1H-imidazo[4,5-c]pyridin-2-yl)-thiazol-5-yl]-pyridin-3-yl-amine (0.016 g, 6% over two steps) as an off-white solid. $^1$H NMR (DMSO-$d_6$) δ: 8.98 (s, 1H), 8.79 (s, 1H), 8.63-8.74 (m, 2H), 8.23-8.38 (m, 2H), 7.81 (dd, J=7.7, 2.5 Hz, 1H), 7.70 (br. s., 1H), 7.40-7.52 (m, 2H); MS (EI/CI) m/z: 295.0 [M+H]$^+$.

Example 41

(1,1-Dimethyl-propyl)-[4-(5-methyl-1H-benzoimidazol-2-yl)-thiazol-5-yl]-amine

Step 1

5-(1,1-Dimethyl-propylamino)-thiazole-4-carboxylic acid ethyl ester

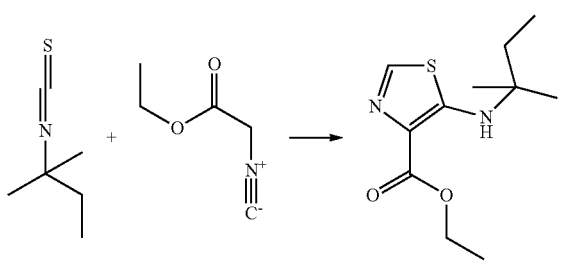

Prepared in a parallel fashion using the procedure described for example 39; MS (EI/CI) m/z: 243.6 [M+H]$^+$.

Step 2

5-(1,1-Dimethyl-propylamino)-thiazole-4-carboxylic acid

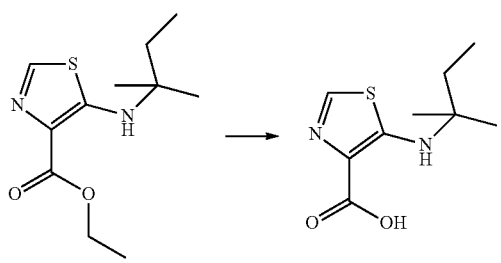 [SMILES: CCOC(=O)c1ncsc1NC(C)(C)CC ; CCC(C)(C)Nc1scnc1C(=O)O]

Prepared in a parallel fashion using the procedure described for example 39; MS (EI/CI) m/z: 213.0 [M−H]⁻.

Step 3

(1,1-Dimethyl-propyl)-[4-(5-methyl-1H-benzoimidazol-2-yl)-thiazol-5-yl]-amine

A solution of 5-(1,1-dimethyl-propylamino)-thiazole-4-carboxylic acid (0.153 g, 0.71 mmol), diisopropylethylamine (0.16 mL, 0.93 mmol) and 4-methyl-benzene-1,2-diamine (0.096 g, 0.78 mmol) in DMF (2 mL) at room temperature was treated with TBTU (0.3 g, 0.93 mmol) and the mixture stirred for 18 h at room temperature. The mixture was then concentrated under vacuum and the residue dissolved ethyl acetate, washed with a saturated solution of sodium bicarbonate, dried with magnesium sulfate and then concentrated under vacuum. The crude mixture was dissolved in acetic acid (3 mL), transferred to microwave vial and heated in a microwave reactor at 120° C. for 2 h. The mixture was cooled, concentrated in vacuo, then the residue was dissolved in dichloromethane, washed with a saturated solution of sodium bicarbonate, dried with magnesium sulfate and concentrated under vacuum. The residue was purified by chromatography (silica, 0 to 5% of a 9:1 methanol:ammonium hydroxide solution in dichloromethane, 20 min) to yield (1,1-dimethyl-propyl)-[4-(5-methyl-1H-benzoimidazol-2-yl)-thiazol-5-yl]-amine (0.044 g, 21%) as an dark green oil. ¹H NMR (CHLOROFORM-d) δ: 10.48-10.81 (m, 1H), 8.73 (d, J=17.4 Hz, 1H), 7.99 (s, 1H), 7.46-7.67 (m, 1H), 7.20-7.35 (m, 1H), 6.94-7.11 (m, 1H), 2.48 (d, J=4.5 Hz, 3H), 1.82 (q, J=7.3 Hz, 2H), 1.46 (s, 6H), 1.00 (t, J=7.4 Hz, 3H); MS (EI/CI) m/z: 301.0 [M+H]⁺.

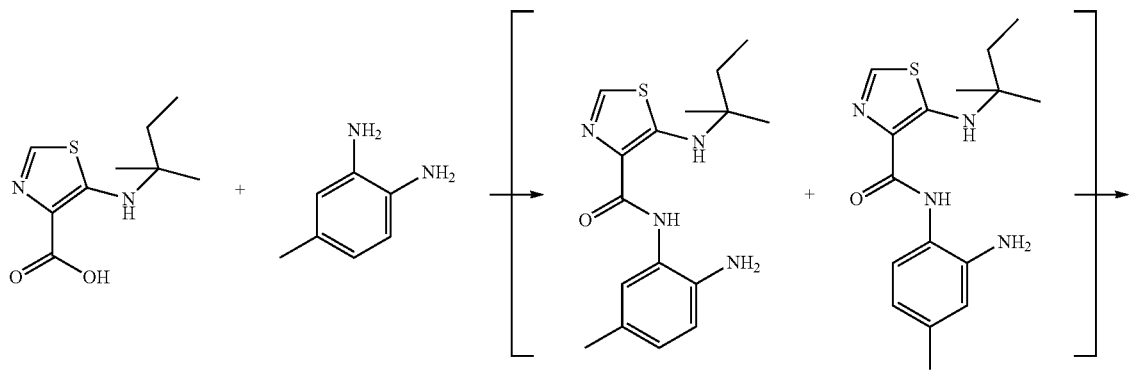

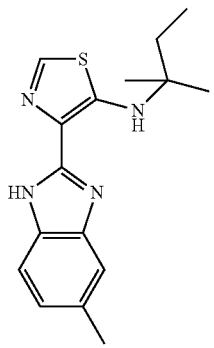

Example 42

Cyclopentyl-[4-(5-methyl-1H-benzoimidazol-2-yl)-thiazol-5-yl]-amine

Step 1

5-Cyclopentylamino-thiazole-4-carboxylic acid ethyl ester

Prepared in a parallel fashion using the procedure described for example 39; MS (EI/CI) m/z: 241.7 [M+H]⁺.

Step 2

5-Cyclopentylamino-thiazole-4-carboxylic acid

Prepared in a parallel fashion using the procedure described for example 39; MS (EI/CI) m/z: 213.4 [M+H]⁺.

Step 3

Cyclopentyl-[4-(5-methyl-1H-benzoimidazol-2-yl)-thiazol-5-yl]-amine

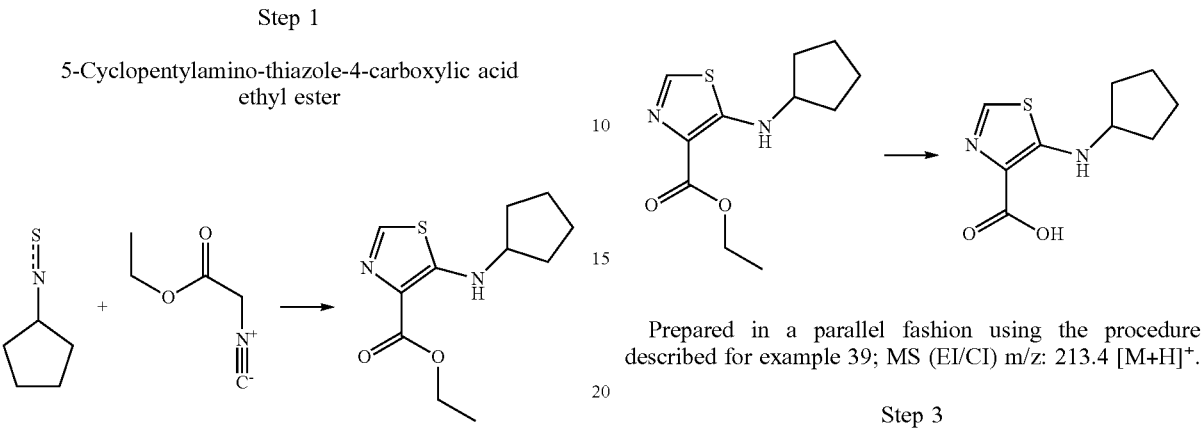

A solution of 5-cyclopentylamino-thiazole-4-carboxylic acid (0.124 g, 0.58 mmol), diisopropylethylamine (0.13 mL, 0.76 mmol) and 4-methyl-benzene-1,2-diamine (0.078 g, 0.64 mmol) in DMF (2 mL) at room temperature was treated with TBTU (0.244 g, 0.76 mmol) and the mixture stirred for 18 h at room temperature. The solvents were removed under vacuum and the residue then dissolved in ethyl acetate, washed with a saturated solution of sodium bicarbonate, dried over magnesium sulfate and finally concentrated under vacuum. The crude mixture was dissolved in acetic acid (3 mL), transferred to microwave vial and heated at 120° C. in a microwave reactor for 2 h. The mixture was cooled, concentrated in vacuo, and then dissolved in dichloromethane. The organic phase was washed with a saturated solution of sodium bicarbonate, dried with magnesium sulfate and concentrated under vacuum. The residue was purified by chromatography (silica, dichloromethane) to yield cyclopentyl-[4-(5-methyl-1H-benzoimidazol-2-yl)-thiazol-5-yl]-amine (0.035 g, 20%) as a beige solid. $^1$H NMR (CHLOROFORM-d) δ: 10.35-10.58 (m, 1H), 8.16 (dd, J=17.6, 6.6 Hz, 1H), 7.98 (s, 1H), 7.47-7.63 (m, 1H), 7.19-7.33 (m, 1H), 6.95-7.09 (m, 1H), 3.65-3.86 (m, 1H), 2.48 (d, J=4.2 Hz, 3H), 2.00-2.24 (m, 2H), 1.59-1.96 (m, 6H); MS (EI/CI) in/z: 299.1 [M+H]$^+$.

Example 43

Isobutyl-[4-(5-methyl-1H-benzoimidazol-2-yl)-thiazol-5-yl]-amine

Step 1

5-Isobutylamino-thiazole-4-carboxylic acid ethyl ester

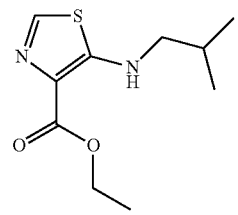

Prepared in a parallel fashion using the procedure described for example 39; MS (EI/CI) m/z: 229.7 [M+H]$^+$.

Step 2

5-Isobutylamino-thiazole-4-carboxylic acid

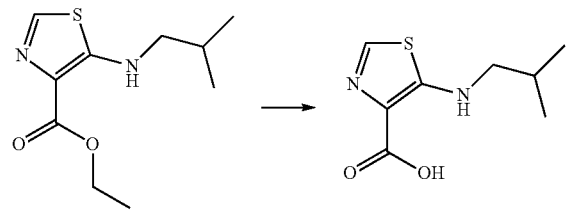

Prepared in a parallel fashion using the procedure described for example 39; MS (EI/CI) m/z: 201.7 [M+H]$^+$.

Step 3

Isobutyl-[4-(5-methyl-1H-benzoimidazol-2-yl)-thiazol-5-yl]-amine

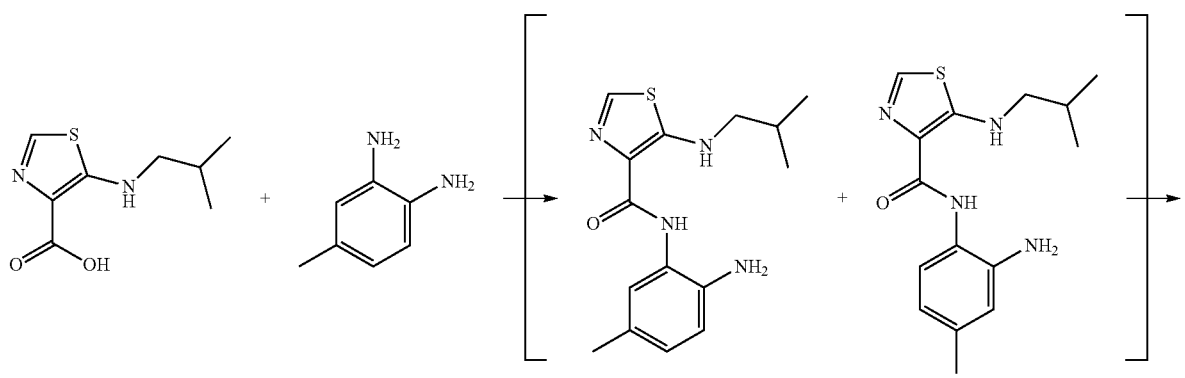

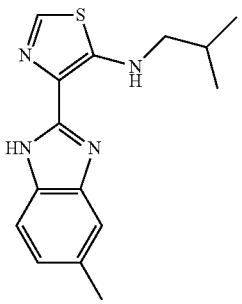

A solution of 5-isobutylamino-thiazole-4-carboxylic acid (0.160 g, 0.80 mmol), diisopropylethylamine (0.18 mL, 1.04 mmol) and 4-methyl-benzene-1,2-diamine (0.107 g, 0.88 mmol) in DMF (2 mL) at room temperature was treated with TBTU (0.333 g, 1.04 mmol) and mixture stirred for 18 h at room temperature. The mixture was concentrated in vacuo and the residue obtained dissolved in ethyl acetate. The organic solution was washed with a saturated solution of sodium bicarbonate, dried with magnesium sulfate and then concentrated under vacuum. The crude mixture was dissolved in acetic acid (3 mL), transferred to microwave vial and heated in a microwave reactor at 120° C. for 2 h. The mixture was cooled, concentrated in vacuo, and then the residue was dissolved in dichloromethane. This solution was washed with a saturated solution of sodium bicarbonate, dried with magnesium sulfate and concentrated under vacuum. The residue was purified by chromatography (silica, dichloromethane) to give isobutyl-[4-(5-methyl-1H-benzoimidazol-2-yl)-thiazol-5-yl]-amine (0.066 g, 29%) as a dark red oil. $^1$H NMR (CHLOROFORM-d) δ: 10.43-10.62 (m, 1H), 8.30 (dt, J=16.1, 5.8 Hz, 1H), 7.97 (s, 1H), 7.51 (s, 1H), 7.18-7.34 (m, 1H), 6.94-7.09 (m, 1H), 3.19 (t, J=6.2 Hz, 2H), 2.48 (d, J=4.5 Hz, 3H), 2.10 (dquin, J=13.5, 6.6 Hz, 1H), 1.08 (d, J=6.8 Hz, 6H); MS (EI/CI) in/z: 287.1 [M+H]$^+$.

Biological Examples

SYK Assay Information
Determination of IC$_{50}$ of Spleen Tyrosine Kinase (SYK) Inhibition:

SYK kinase assay is a standard kinase assay adapted to a 96 well plate format. This assay is performed in 96-well format for IC$_{50}$ determination with 8 samples which represented 10 half log dilutions and a 40 µL reaction volume. The assay measures the incorporation of radiolabeled $^{33}$P ATP into an N-terminally biotinylated peptide substrate, derived from naturally occurring phosphoacceptor consensus sequence (Biotin-11aa DY*E). Phosphorylated products were detected upon termination of reactions with EDTA and the addition of Streptavidin coated beads. Representative results are in Table II above.

Assay plates: 96-well MultiScreen 0.65 um filter plates (Millipore Cat. No.: MADVNOB10) Streptavidin coated beads: Streptavidin Sepharose™, suspension 5.0 mL, in 50 mM EDTA/PBS diluted (1:100), (Amersham, Cat. No.: 17-5113-01)

Compounds: 10 mM in 100% dimethylsulfoxide (DMSO), final conc.: compound 0.003-100 uM in 10% DMSO Enzyme: SYK RPA purified, truncated construct of Spleen Tyrosine Kinase aa 360-635, stock solution 1 mg/mL, MW: 31.2 KDa, final conc.:0.0005 µM.

Peptide 1: biotinylated peptide is derived from a naturally occurring phosphor-acceptor consensus sequence (Biotin-EPEGDYEEVLE), special order from QCB, stock solution 20 mM, final conc.: 5.0 µM.

ATP: Adenosine-5'-triphosphate 20 mM, (ROCHE Cat. No.: 93202720), final concentration: 20 µM Buffer: HEPES: 2-Hydroxyethyl piperazine-2-ethanesulfonic acid (Sigma, Cat. No.: H-3375) final concentration: 50 mM HEPES pH7.5

BSA: Bovine Serum Albumin Fraction V, fatty acid free (Roche Diagnostics GmbH, Cat. No. 9100221) diluted to a final concentration of 0.1%

EDTA: EDTA stock solution 500 mM, (GIBCO, Cat. No.: 15575-038) final concentration: 0.1 mM DTT: 1,4-Dithiothreitol (Roche Diagnostics GmbH, Cat. No.: 197777), final conc.: 1 mM MgCl$_2$×6H$_2$O: MERCK, Cat. No.: 105833.1000, final concentration: 10 mM Assay Dilution Buffer (ADB): 50 mM HEPES, 0.1 mM EGTA, 0.1 mM Na Vanadate, 0.1 mM β-glycerophosphate, 10 mM MgCl$_2$, 1 mM DTT, 0.1% BSA, pH 7.5

Bead wash buffer: 10 g/L PBS (Phosphate buffered saline) with 2M NaCl+1% phosphoric acid.

Experimental Method:

In 40 µL volume, 26 µL of ADB diluted, purified recombinant human SYK360-635 [0.5 nM] was mixed with 4 µL of 10× concentrations of the test compounds, [usually 100 µM-0.003 µM] in [10%] DMSO and the mixture was incubated for 10 min at RT.

The kinase reaction was initiated by the addition of 10 µL 4× substrate cocktail containing the DYE peptide substrate [0 or 5 µM], ATP [20 µM] and $^{33}$PγATP [2 µCi/rxn]. After incubation at 30° C. for 15 min, the reaction was terminated by the transfer of 25 µL pf the reaction sample to a 96 well 0.65 µm Millipore MADVNOB membrane/plate containing 200 µL 5 mM EDTA and 20% Streptavidine coated beads in PBS.

The unbound radionucleotides were washed under vacuum with 3×250 µL 2M NaCl; 2×250 µL 2M NaCl+1% phosphoric acid; 1×250 µL H$_2$O. After the last wash membrane/plates were transferred to an adaptor plate, heat dried for 15 min at 60° C., and 50 µL scintillation cocktail was added to each well and 4 h later the amount of radioactivity was counted in a top counter.

The percent inhibition was calculated based on the uninhibited enzyme rate:

$$\% \text{ Inhibition} = 100/(1+(\text{IC}_{50}/\text{Inhibitor conc})^n)$$

The IC$_{50}$ was calculated using a non-linear curve fit with XLfit software (ID Business Solution Ltd., Guilford, Surrey, UK).

| Compound | ENZYME_FILTRATION_IC50 | RAMOS_V2_IC50 | IC50: human whole blood |
|---|---|---|---|
| I-1 | 35.1892 | | |
| I-2 | 0.1126 | >34.09 | |
| I-3 | 2.0773 | 5.40966 | |
| I-4 | 0.6209 | 3.831025 | |
| I-5 | 1.27905 | 4.645375 | |
| I-6 | 2.75945 | 11.98022 | |
| I-7 | 0.5619 | 0.551606 | 20.3658 |
| I-8 | 0.067 | 0.145682 | 46.6636 |
| I-9 | >10 | | >50 |
| I-10 | >10 | | >50 |
| I-11 | 7.94955 | >34.09 | |
| I-12 | 1.687 | 4.07351 | 13.1175 |
| I-13 | >10 | >34.09 | >50 |
| I-14 | >10 | >34.09 | |
| I-15 | >10 | >34.09 | |
| I-16 | 2.40935 | 12.160015 | >50 |
| I-17 | 0.7608 | 3.5410475 | >50 |
| I-18 | 6.1238 | >34.09 | >50 |
| I-19 | | >34.09 | >50 |
| I-20 | 0.2154 | | >50 |
| I-21 | 0.20895 | 19.067255 | >50 |
| I-22 | 1.99345 | >34.09 | |
| I-23 | 7.87075 | >34.09 | |
| I-24 | | | >50 |
| I-25 | 4.60585 | 5.20907 | |
| I-26 | 1.22925 | | |
| I-27 | 4.64035 | 15.507915 | |
| I-28 | 1.12665 | 6.412955 | |
| I-29 | 0.0466 | 1.520248 | 10.3825 |
| I-30 | 0.06005 | 1.016505 | 2.2871 |
| I-31 | 0.02145 | 0.349586667 | 2.6025 |
| I-32 | 0.0389 | 0.61519 | 5.2724 |
| I-33 | 0.1048 | 3.08306 | 2.5008 |
| I-34 | 0.27845 | 6.568568 | 4.1701 |
| I-35 | 0.05495 | 0.92046 | 1.9186 |
| I-36 | | 0.292265 | 2.5424 |
| I-37 | | 0.140125 | 2.8606 |
| I-38 | | 0.483085 | 0.87 |
| I-39 | | 0.9864 | 2.8688 |
| I-40 | 0.4872 | 0.7637985 | |
| I-41 | 5.43715 | >31.25 | |
| I-42 | 1.6235 | | >50 |
| I-43 | 0.69885 | >34.09 | |
| I-44 | 0.62125 | 7.984055 | |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:
1. A compound, selected from the group consisting of:
 N-[3-(1H-Benzoimidazol-2-yl)-1H-pyrazol-4-yl]-isobutyramide;
 N-[3-(1H-Benzoimidazol-2-yl)-1H-pyrazol-4-yl]-2,2-dimetyl-propionamide;
 Cyclopentanecarboxylic acid [3-(1H-benzoimidazol-2-yl)-1H-pyrazol-4-yl]-amide;
 Acetic acid 2-[3-(1H-benzoimidazol-2-yl)-1H-pyrazol-4-ylcarhamoyl]-2-methyl-propyl ester;
 N-[3-(1H-Benzoimidazol-2-yl)-1H-pyrazol-4-yl]-3-hydroxy-2,2-dimethyl-propionamide;
 3-(1H-Benzoimidazol-2-yl)-1H-pyrazole-4-carboxylic acid isopropylamide;
 3-(1H-Benzoimidazol-2-yl)-1H-pyrazole-4-carboxylic acid tert-butylamide; and
 3-(1H-Benzoimidazol-2-yl)-1H-pyrazole-4-carboxylic acid (2-hydroxy-1,1-dimethyl-ethyl) amide
 or a pharmaceutically acceptable salt thereof.

* * * * *

UNITED STATES PATENT AND TRADEMARK OFFICE
CERTIFICATE OF CORRECTION

PATENT NO.         : 9,988,378 B2
APPLICATION NO.    : 14/437307
DATED              : June 5, 2018
INVENTOR(S)        : Bhagirath et al.

It is certified that error appears in the above-identified patent and that said Letters Patent is hereby corrected as shown below:

In the Claims

At Column 104, Lines 46-47, "2-dimetyl..." should be replaced with "2-dimethyl..."

At Column 104, Line 51, "ylcarhamoyl..." should be replaced "ylcarbamoyl..."

Signed and Sealed this
Fourteenth Day of August, 2018

Andrei Iancu
*Director of the United States Patent and Trademark Office*